US010450352B2

(12) United States Patent
Maynard et al.

(10) Patent No.: US 10,450,352 B2
(45) Date of Patent: Oct. 22, 2019

(54) ENGINEERED POLYPEPTIDES FOR ANTIGEN DELIVERY

(71) Applicant: BOARD OF REGENTS, THE UNIVERSITY OF TEXAS SYSTEM, Austin, TX (US)

(72) Inventors: Jennifer Maynard, Austin, TX (US); Xianzhe Wang, Brookline, MA (US); Tarik Ali Khan, Basel (CH)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/087,215

(22) PCT Filed: Mar. 23, 2017

(86) PCT No.: PCT/US2017/023796
§ 371 (c)(1),
(2) Date: Sep. 21, 2018

(87) PCT Pub. No.: WO2017/165636
PCT Pub. Date: Sep. 28, 2017

(65) Prior Publication Data

US 2019/0106463 A1 Apr. 11, 2019

Related U.S. Application Data

(60) Provisional application No. 62/312,021, filed on Mar. 23, 2016.

(51) Int. Cl.

| | |
|---|---|
| *C07K 1/00* | (2006.01) |
| *C07K 14/24* | (2006.01) |
| *A61K 35/66* | (2015.01) |
| *A61K 35/12* | (2015.01) |
| *C07K 14/00* | (2006.01) |
| *C07K 14/47* | (2006.01) |
| *A61K 39/00* | (2006.01) |
| *A61K 47/66* | (2017.01) |
| *C12N 15/85* | (2006.01) |

(52) U.S. Cl.
CPC .............. *C07K 14/24* (2013.01); *A61K 35/12* (2013.01); *A61K 35/66* (2013.01); *A61K 39/00* (2013.01); *A61K 47/66* (2017.08); *C07K 14/00* (2013.01); *C07K 14/47* (2013.01); *C12N 15/85* (2013.01); *A61K 2039/6068* (2013.01); *C12N 2015/8518* (2013.01); *Y02A 50/471* (2018.01); *Y02A 50/475* (2018.01)

(58) Field of Classification Search
CPC ...................................................... C07K 14/24
See application file for complete search history.

(56) References Cited

U.S. PATENT DOCUMENTS 7,871,815 B2 * 1/2011 Sabbadini .............. C12N 15/00 435/320.1

* cited by examiner

*Primary Examiner* — Albert M Navarro
(74) *Attorney, Agent, or Firm* — Parker Highlander PLLC

(57) ABSTRACT

Recombinant high affinity Invasin polypeptide are provided herein. Further provided are methods of delivering therapeutics such as vaccines by conjugation to the engineered recombinant Invasin polypeptides.

20 Claims, 28 Drawing Sheets

Specification includes a Sequence Listing.

imaged immediately imaged after 18 hrs

ENGINEERED POLYPEPTIDES FOR ANTIGEN DELIVERY

The present application is a national phase application under 35 U.S.C. § 371 of International Application No. PCT/US2017/023796, filed Mar. 23, 2017, which claims the priority benefit of U.S. Provisional Application Ser. No. 62/312,021, filed Mar. 23, 2016, the entire contents of each of which is hereby incorporated by reference.

INCORPORATION OF SEQUENCE LISTING

The sequence listing that is contained in the file named "UTFBP1109WO_ST25.txt", which is 28 KB (as measured in Microsoft Windows®) and was created on Mar. 23, 2017, is filed herewith by electronic submission and is incorporated by reference herein.

BACKGROUND OF THE INVENTION

1. Field of the Invention

The present invention relates generally to the field of molecular biology. More particularly, it concerns methods and compositions of modified invasion polypeptides.

2. Description of Related Art

*Yersinia enterocolitica* and *Y. pseudotuberculosis* are human enteropathogens that have evolved a specialized mechanism to invade the host: the bacteria target antigen sampling cells in the small intestine. These microfold (M) cells normally sample gut contents for delivery to underlying mucosal-associated lymphoid tissue, able to detect and respond to infections (Brayden et al., 2005). M cells are sparsely distributed and chemically unique, being the only cells in the small intestine to display $\beta_1$ integrins on their apical surface (Clark et al., 2002). *Yersinia* have exploited this normally protective mechanism by targeting the $\beta_1$ integrins with an outer-membrane adhesin, Invason (Isberg and Leong, 1990; Schulte et al., 2000). Interaction of Invasin-decorated bacteria and other particles with the $\alpha_5\beta_1$ integrin triggers integrin clustering, followed by rapid uptake into M cells as well as non-phagocytic cells (Isberg et al., 1987; Dersch and Isberg, 1999). This ability has stimulated interest in understanding Invasin's mechanism as well as its potential to mediate delivery of oral vaccines (Leibiger et al., 2008; Palumbo and Wang, 2006; Panthani et al., 2013).

Invasin is a large, 986 residue outer-membrane protein that is expressed during the early stages of infection by enteropathogenic *Yersinia*. It is secreted from the gram-negative bacteria by a Type Ve Sec-dependent inverse autotransporter mechanism and anchored in the outer membrane by its N-terminal beta-barrel transmembrane domain (Fairman et al., 2012). The extracellular region comprises five domains (D1 through D5), which together form an 18 nm rod-like extension. Domains D1 through D4 adopt bacterial immunoglobulin-like structures while D5 assumes a C-type lectin-like domain structure, forming a superdomain with D4 by virtue of a large shared interface (Hamburger et al., 1999). Multiple factors are thought to control internalization efficiency of Invasin, including ligand-integrin affinity and ligand dimerization, as well as ligand and integrin receptor surface densities. However, to date it remained unknown what changes could be made to invasion polypeptides to enhance internalization efficiency of the molecules.

SUMMARY OF THE INVENTION

Embodiments of the present disclosure provide methods and compositions of Invasin variants. In one embodiment, there is provided a recombinant polypeptide comprising an Invasin D5 domain coding sequence at least 80% identical to amino acid residues 887-986 of SEQ ID NO: 1, wherein the Invasin D5 domain coding sequence comprises an amino acid substitution at the position corresponding to Gly 909 and/or an amino acid substitution at the position corresponding to Ser 910. In some aspects, the polypeptide comprises an amino acid substitution at the position corresponding to Gly 909 and an amino acid substitution at the position corresponding to Ser 910. In certain aspects, the polypeptide comprises an amino acid substitution for a residue having a positively charged side chain at the position corresponding to Gly 909. For example, the polypeptide comprises an Arg substitution at the position corresponding to Gly 909. In some aspects, the polypeptide comprises an amino acid substitution for an aliphatic residue at the position corresponding to Ser 910. For example, the polypeptide comprises a Gly substitution at the position corresponding to Ser 910. In particular aspects, the polypeptide comprises an Arg substitution at the position corresponding to Gly 909 and a Gly substitution at the position corresponding to Ser 910.

In certain aspects, the polypeptide comprises a $^{909}$RGD$^{911}$ motif. In some aspects, the $^{909}$RGD$^{911}$ motif increases integrin binding affinity by at least 10 fold as compared to wild-type Invasin. In certain aspects, the $^{909}$RGD$^{911}$ motif increases integrin binding affinity by at least 50 fold as compared to wild-type Invasin. In some aspects, the $^{909}$RGD$^{911}$ motif increases integrin binding affinity by at least 1000 fold as compared to wild-type Invasin. For example, the integrin is $\alpha_5\beta_1$, $\alpha_\nu\beta_1$ integrin or $\alpha_\nu\beta_3$ integrin. In some aspects, the $^{909}$RGD$^{911}$ motif increases affinity for $\alpha_5\beta_1$ integrin by at least 10-fold, such as at least 50-fold, particularly at least 100-fold. In further aspects, the $^{909}$RGD$^{911}$ motif increases uptake of cells (e.g., M cells).

In certain aspects, the polypeptide further comprises an Invasin D4 coding sequence at least 80% identical to amino acid residues 795-886 of SEQ ID NO: 1. In some aspects, the Invasin D4 coding sequence comprises one or more of the following features: (a) an amino acid substitution at the position corresponding to Phe 844; (b) an amino acid substitution at the position corresponding to Tyr 878; or (c) an amino acid substitution at the position corresponding to Tyr 885. In some aspects, the Invasin D4 domain coding sequence comprises two or three of said features.

In some aspects, the polypeptide comprises an amino acid substitution for a residue having a hydrophobic side chain at the position corresponding to Phe 844. For example, the polypeptide comprises a Tyr substitution at the position corresponding to Phe 844. In some aspects, the polypeptide comprises an amino acid substitution for a residue having a hydrophobic side chain at the position corresponding to Tyr 878. For example, the polypeptide comprises an Ala substitution at the position corresponding to Tyr 878. In some aspects, the polypeptide comprises an amino acid substitution for a residue having a hydrophobic side chain at the position corresponding to Tyr 885. For example, the polypeptide comprises an Ala substitution at the position corresponding to Tyr 885.

In certain aspects, the polypeptide further comprises a mutation of an Invasin protease site. In particular aspects, the mutation comprises an amino acid substitution or deletion at the position corresponding to Lys 873 and/or an amino acid substitution or deletion at the position corresponding to Lys 874. In some aspects, the polypeptide is further conjugated to an imaging agent.

A further embodiment provides a composition comprising an Invasin polypeptide of the embodiments in a pharmaceutically acceptable carrier. In some aspects, the composition further comprises a therapeutic moiety. In certain aspects, the polypeptide and therapeutic moiety are linked by a degradable peptide sequence. In other aspects, the polypeptide and the therapeutic moiety are not linked. For example, the therapeutic moiety can be an immunogenic composition comprising at least one antigen. Accordingly, in some aspects, the $^{909}RGD^{911}$ motif of the Invasin polypeptide can induce superior immune responses against the antigen. Thus, in some aspects, composition of the embodiments comprises an Invasin polypeptide comprising the $^{909}RGD^{911}$ motif linked to an immunogenic composition comprising at least a first antigen.

Another embodiment provides a polynucleotide molecule comprising a nucleic acid sequence encoding an Invasin polypeptide of the embodiments.

In still a further embodiment, a host cell is provided comprising an expressible polynucleotide sequence encoding an Invasin polypeptide of the embodiments. In some aspects, the host cell further comprises a therapeutic moiety. For example, a host cell of the embodiments can be a mammalian cell (e.g., a cultured human cell), a yeast cell, a bacterial cell, a ciliate cell or an insect cell. Thus, in a further embodiment there is provided a method of manufacturing a polypeptide comprising: (a) expressing a polynucleotide molecule encoding an Invasin polypeptide of the embodiments in a cell under conditions to produce the encoded polypeptide; and (b) purifying the polypeptide from the cell.

In yet another embodiment, there is provided a method for the delivery of a therapeutic agent comprising a therapeutic agent and an Invasin polypeptide of the embodiments. In some aspects, the polypeptide transports the therapeutic agent across the gastrointestinal membrane. In certain aspects, the delivery method further comprises a pharmaceutically acceptable carrier. In some aspects, the pharmaceutically acceptable carrier is a liposome or polymer-based particle (e.g., biodegradable polymer). In particular aspects, the polymer-based particle (e.g., PLGA) is conjugated to the Invasin polypeptide and therapeutic agent (e.g., an antigen). In some aspects, compositions comprising an Invasin polypeptide and a therapeutic agent (e.g., an antigen) further comprise a further active agent, such as an adjuvant.

In a further embodiment, there is provided a method of eliciting an immune response in a subject comprising administering at least one antigen and an Invasin polypeptide of the embodiments. In some aspects, the at least one antigen is conjugated to the Invasin polypeptide, thereby forming a fusion protein. In certain aspects, the immune response treats a disease. For example, the disease is an infectious diseases, autoimmune disease, allergy, or cancer. In some aspects, the infectious disease is viral, bacterial or protozoological. In certain aspects, the antigen is selected from a group consisting of gastro-intestinal antigens, peptide antigens, tumor antigens, self-antigens, auto-immune self-antigens, pathogenic antigens, viral antigens, bacterial antigens, fungal antigens, protozoological antigens, animal antigens, and allergy antigens. For example, the gastro-intestinal antigens can be an antigen from norovirus, salmonella, E. coli, shigella (e.g., Shiga toxin 1 and Shiga toxin 2), or cholera. In some aspects, the method further comprises administering an antacid or protease inhibitor. In certain aspects, the method further comprises administering at least one additional adjuvant or immune system stimulant.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figure 14:
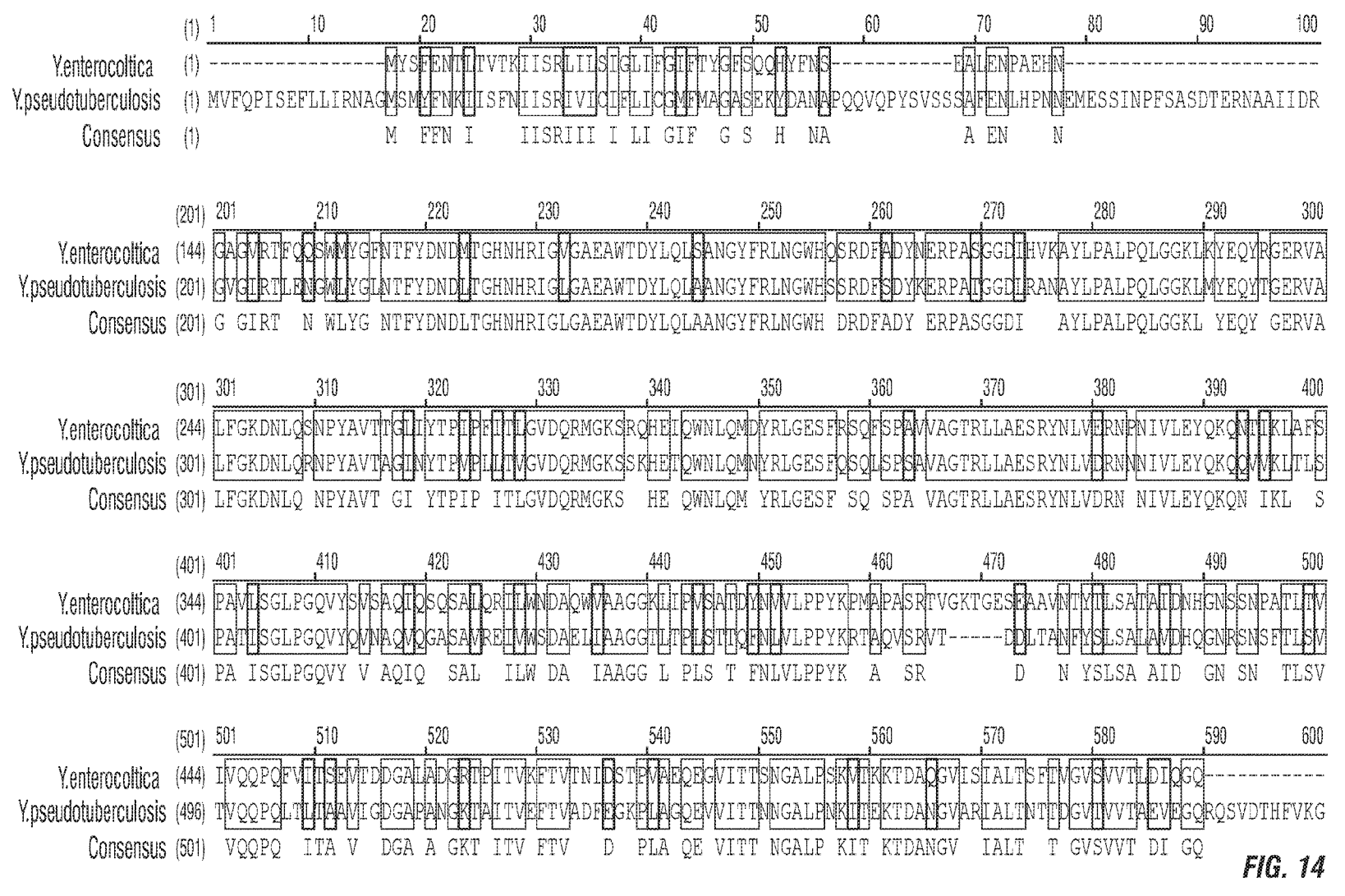
Figure 14:
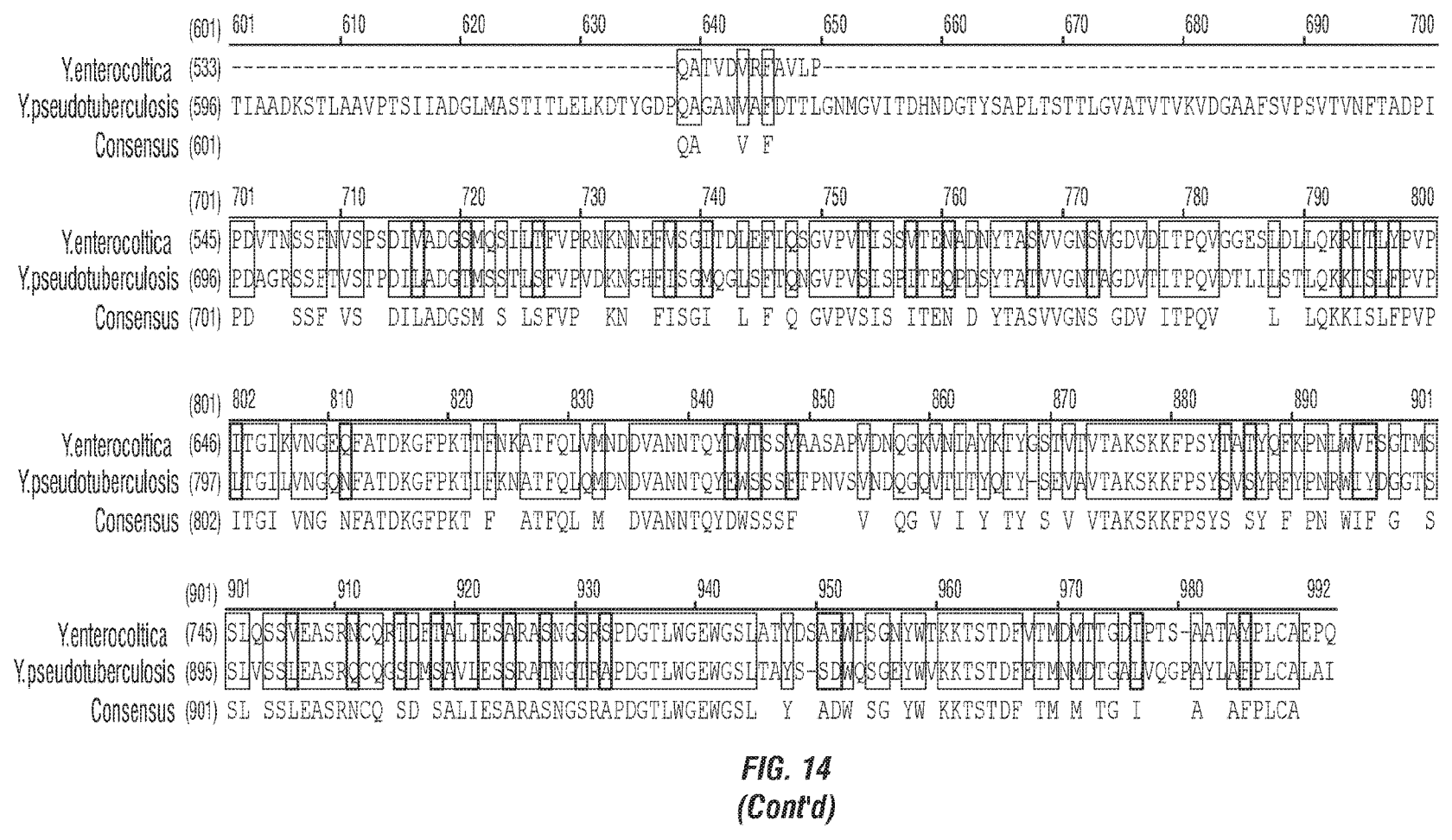

FIG. 14: Sequence alignment of Invasion homologs *Y. pseudotuberculosis* (SEQ ID NO: 10) and *Y. enterocolitica* (SEQ ID NO: 9). The *Y. enterocolitica* Invasin does not contain the D2 domain. (consensus=SEQ ID NO: 11)

FIGS. 15A-15B: (15A) Single major protease site in Invasin between Lys873 and Lys874. (15B) Caco-2 cell invasion by bacteria displaying Invasin variants (top). Confocal microscopy to confirm the internalization of beads (bottom).

FIG. 16: SDS page of invasion-MBP digested with trypsin. Invasin (compete D1-D5 region) was expressed as maltose binding protein (MBP) fusion protein. Purified invasin-MBP was digested with 250 ng/ml trypsin at 37° C. for 1 h, 2 h or 3 h. The first lane labeled with 0 means Invasin-MBP itself without trypsin stored at 37° C. for 3 h as control. Mass spectrometry has demonstrated that the digested product at 52 kD was invasin, and the digested product at 41 kD was MBP.

FIG. 17: SDS page of invasion (D1-D5)-MBP digested with simulated intestinal fluid. Simulated intestinal fluid with different concentrations of the enzyme pancreatin was used to digest invasin-MBP at 37° C. for 2 h. With the increase of pancreatin concentration, more invasion-MBP was cut into invasin and MBP, but invasin itself was not cut into small pieces.

FIG. 18: Integrin binding on digested invasin display *E. coli*. Invasin display *E. coli* expressing a high level of GFP were digested with simulated intestinal fluid. Proteolytic resistant invasin was labeled by fluorescent $\alpha5\beta1$ integrins. FACS was used to record the percentage of $\alpha5\beta1$ integrins positive in the digested *E. coli*. As the simulated intestinal fluid could not digest invasin displayed on *E. coli*, the digested *E. coli* could still be labeled with fluorescent $\alpha5\beta1$ integrins indicating they retain the ability to bind M cells under realistic intestinal conditions.

DESCRIPTION OF ILLUSTRATIVE EMBODIMENTS

Oral delivery of proteins for therapy and to induce immune responses, is a growing area of interest among pharmaceutical and biotechnology companies. However, one key barrier is delivery from the gut lumen, across the epithelial cell layer and into target tissues. Invasin polypeptides hold promise in providing delivery of agents across the gut epithelium. However, wild-type molecules display limited transit efficiency that is not ideal for clinical development.

Studies detailed herein show the results of alanine scanning mutagenesis, which identified residues modulating integrin binding. Four libraries with targeted mutations were constructed, followed by selection for variants able to infect Caco-2 cells and bind soluble $\alpha_5\beta_1$ integrin. These variants were characterized for integrin binding and specificity as well the ability to mediate particle internalization. The new recombinant Invasin polypeptides that were identified were demonstrated to significantly enhance transit efficiently and alter cell type specificity. Accordingly, methods are provided for the use of these Invasin variants to bind and delivery cargo such as to intestinal M cells and the underlying local intestinal lymph tissue. Further, the Invasin variants can be coated on cargo molecules for internalization into these normally non-phagocytic cells. In some aspects, the Invasin variants are used to more efficiently deliver antigenic cargo to intestinal immune cells, result in significantly improved responses to the antigen. Importantly, local mucosal responses can be mediated by the Invasin molecules, which can provide protection against gastro-intestinal diseases such as norovirus and shigellosis. In particular, the Invasin variants provided herein can be used for targeting vaccine antigens to M cells, such as in the context of an in vivo intestinal environment, as they were shown to be resistant to proteolysis by intestinal enzymes. In addition, the Invasin variants may be used for increasing drug transport through other non-invasive routes where the appropriate receptors are expressed (e.g., for nasal, ocular, rectal, vaginal, pulmonary and transdermal administration).

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

"Treatment" and "treating" refer to administration or application of a therapeutic agent to a subject or performance of a procedure or modality on a subject for the purpose of obtaining a therapeutic benefit of a disease or health-related condition.

"Subject" and "patient" refer to either a human or non-human, such as primates, mammals, and vertebrates. In particular embodiments, the subject is a human.

An "Invasin" polypeptide or protein as referred to herein is a protein originating from an enteroinvasive bacteria which is necessary for that organism to induce phagocytosis in an epithelial cell. In preferred aspects, the Invasin polypeptides provided herein comprise at least an Invasin D5 and, optionally D4, domain.

Figure 1A:
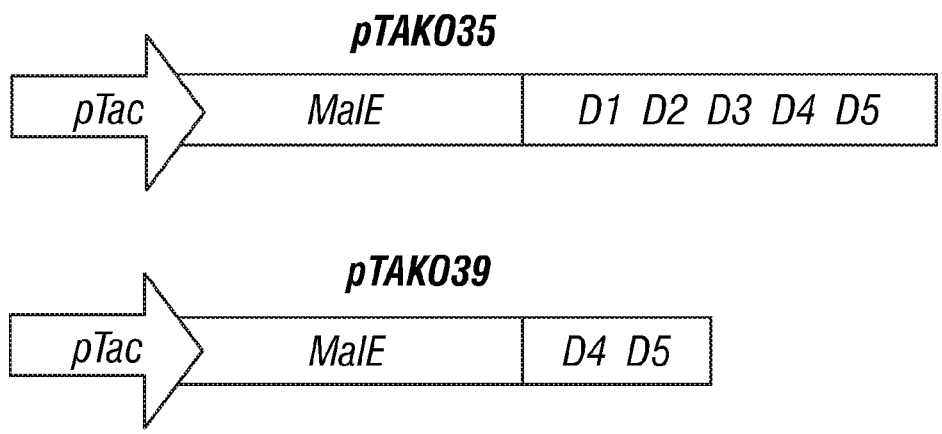
FIGS. 1A-1D—Soluble expression of active Invasin from E. coli. 1A, Plasmid pTAK035 encodes Invasin domains D1D5 (residues 503-986) while plasmid pTAK039 encodes the minimal integrin binding domain D4D5 (residues 795-986). Both were cloned as C-terminal fusions to the malE gene encoding maltose binding protein in the pMAL-c5x (NEB) plasmid. 1B, Purification of the wild-type (WT) and D911A Invasin variants as MBP-D1D5 constructs resulted in a single peak, with an observed molecular weight of 145 kDa (indicated by an arrow). The expected size of the MBP-D1D5 monomer is 94 kDa; the larger observed size may reflect delayed elution due to the protein's rod-like shape. The size exclusion chromatography trace (S200 column, Åkta FPLC) after an initial amylose affinity purification step is shown. Inset, SDS-PAGE gel of purified MBP-D1D5, with molecular weight markers indicated. 1C, Purification of WT Invasin as an MBP-D4D5 construct, with an observed molecular weight of 62 kDa (indicated by arrow). The size exclusion chromatography trace (S75 column, Åkta FPLC) collected after an initial amylose affinity purification step is shown. Inset, SDS-PAGE gel of purified MBP-D4D5, with molecular weight markers indicated. 1D, ELISA to assess binding activity of purified Invasin variants for the $\alpha_5\beta_1$ integrin. The MBP-Invasin fusion proteins were titrated on recombinant $\alpha_5\beta_1$ integrin-coated ELISA plate in the presence of 2 mM $MnCl_2$, followed by detection with anti-MBP-horse-radish peroxidase conjugate. No binding was observed for Invasin variants containing the D911A amino acid substitution or for any variant on uncoated wells.

The term "vector" is intended to include any physical or biochemical vehicle containing nucleic acid polymers of interest, by which those nucleic acid polymers are transferred into a host cell, thereby transforming that cell with the introduced nucleic acid polymers. Vectors provided herein include, but are not limited to, expression vectors comprising a coding sequence for an Invasin variant disclosed herein.

The term "host cell" is intended to mean the target cell for vector transformation, in which the transferred nucleic acid polymer will be replicated and/or expressed. For example, in some aspects, Invasin polypeptides are produced in bacterial host cells.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

II. INVASIN POLYPEPTIDES

Certain embodiments of the present disclosure concern recombinant Invasin polypeptides. For example, the Invasin is the *Yersinia pseudotuberculosis* Invasin of SEQ ID NO:1 (GenBank Accession No: M17448.1) or a polypeptide at least about 80%, 85%, 90%, 91%, 92%, 93%, 94%, 95%, 96%, 97%, 98%, 99% or 100% identical to SEQ ID NO: 1. In some embodiments, the recombinant Invasin polypeptides comprise the D5 domain (amino acids 887-986) of SEQ ID NO:1. In some aspects, the recombinant Invasin polypeptide is at least about 80%, 85%, 90%, 91%, 92%, 93%, 94%, 95%, 96%, 97%, 98%, 99% or 100% identical to residues 887-986 of SEQ ID NO:1. In certain embodiments, the mutated Invasin polypeptides comprise the D4/D5 domains (amino acids 795-986) of SEQ ID NO:1, comprising the receptor binding domain. In some aspects, the recombinant Invasin polypeptide is at least about 80%, 85%, 90%, 91%, 92%, 93%, 94%, 95%, 96%, 97%, 98%, 99% or 100% identical to residues 887-986 of SEQ ID NO:1. Additionally, in some aspects, the recombinant Invasin polypeptides can comprise the D1 domain (amino acids 503-594), D2 domain (amino acids 595-693) or the D3 domain (amino acids 694-794). In still further aspects, of the embodiments an Invasin polypeptide comprises no more than 500, 400, 300, 200, 190, 180, 170, 160, 150, 140, 130, 120, 110 or 100 amino acids.

In certain aspects, the recombinant Invasin polypeptides comprise one or more of the following features: an amino acid substitution at the position corresponding to Gly 909, an amino acid substitution at the position corresponding to Ser 910, an amino acid substitution at the position corresponding to Phe 844; an amino acid substitution at the position corresponding to Tyr 878; or an amino acid substitution at the position corresponding to Tyr 885. In particular aspects, the Invasin polypeptides comprise an amino acid substitution for a residue having a positively charged side chain at the position corresponding to Gly 909 and an amino acid substitution for an aliphatic residue at the position corresponding to Ser 910. For example, the Invasin polypeptides can comprise an Arg substitution at the position corresponding to Gly 909 and a Gly substitution at the position corresponding to Ser 910. Accordingly, the Invasin polypeptides can comprise an RGD motif at the positions corresponding to residues 909, 910 and 911. In some aspects, the polypeptide comprises an amino acid substitution for a residue having a hydrophobic side chain at the positions corresponding to Phe 844, Tyr 878, and/or Tyr 885. For example, the polypeptide comprises amino acid substitutions of a Tyr substitution at the position corresponding to Phe 844, an Ala substitution at the position corresponding to Tyr 878 and an Ala substitution at the position corresponding to Tyr 885.

In further aspects, the recombinant Invasin polypeptide may comprise one or more amino acid substitutions to an amino acid at a corresponding position in a different, homologous, Invasin coding sequence (e.g., see FIG. 14). Because of the high homology shared between these polypeptides, such substitutions for corresponding amino acid positions discussed above would be expected to result in a coding sequences that, when expressed, maintains integrin binding activity.

In additional aspects, Invasin polypeptides may be further modified by one or more other amino substitutions while maintaining their integrin binding activity. For example, amino acid substitutions can be made at one or more positions wherein the substitution is for an amino acid having a similar hydrophilicity. The importance of the hydrophobic amino acid index in conferring interactive biologic function on a protein is generally understood in the art (Kyte and Doolittle, 1982). It is accepted that the relative hydrophobic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in Invasin and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the Invasin polypeptides described herein may be modified by the substitution of an amino acid, for different, but homologous amino acid with a similar hydrophilicity value. Amino acids with hydrophilicities within +/−1.0, or +/−0.5 points are considered homologous. Furthermore, it is envisioned that serine protease sequences may be modified by amino acid deletions, substitutions, additions or insertions while retaining its enzymatic activity. In addition, amino acid substitutions may be made to increase or decrease the number of T cell epitopes present within the Invasin molecule.

III. FUSION PROTEINS AND CONJUGATES

In some embodiments, the present disclosure provides fusion proteins comprising the recombinant Invasin polypeptides provided herein fused to a therapeutic moiety. In some aspects, the therapeutic moiety is a vaccine comprising an antigen. The vaccine may be antigens generated outside the cell, more typically antigens not derived from the host organism (e.g. a human) itself (i.e. non-self antigens) but rather derived from host cells outside the host organism, e.g. pathogenic antigens, particularly viral antigens, bacterial antigens, fungal antigens, protozoological antigens, animal antigens (preferably selected from animals or organisms as disclosed herein), allergy antigens, etc. Antigens may be from antigens generated inside the cell, the tissue or the body, e.g. by secretion of proteins, their degradation, metabolism, etc. Such antigens include antigens derived from the host organism (e.g. a human) itself, e.g. tumor antigens, self-antigens or auto-antigens, such as auto-immune self-antigens, etc., but also (non-self) antigens as defined above, which have been originally been derived from host cells outside the host organism, but which are fragmented or degraded inside the body, tissue or cell, e.g. by (protease) degradation, metabolism, etc.

Pathogenic antigens particularly comprise e.g. antigens from influenza, preferably influenza A, influenza B, influenza C or thogotovirus, preferably influenza antigens haemagglutinin (HA) and/or neuraminidase (NA), preferably influenza antigens derived from haemagglutinin subtypes H1, H2, H3, H4, H5, H6, H7, H8, H9, H10, H11, H12, H13, H14 or H15, and/or neuraminidase subtypes N1, N2, N3, N4, N5, N6, N7, N8 or N9, or preferably selected from influenza A subtypes H1N1, H1N2, H2N2, H2N3, H3N1, H3N2, H3N3, H5N1, H5N2, H7N7 or H9N2, or any further combination, or from matrix protein 1 (M1), ion channel protein M2 (M2), nucleoprotein (NP), or e.g. antigens from respiratory syncytial virus (RSV), including F-protein, or G-protein.

In some aspects, the antigen is an allergy antigen. Allergy antigens are typically antigens, which cause an allergy in a human and may be derived from either a human or other sources. Such allergy antigens may be selected from antigens derived from different sources, e.g. from animals, plants, fungi, bacteria, etc. Allergens in this context also include antigens derived from e.g. grasses, pollens, molds, drugs, or numerous environmental triggers. Allergy antigens typically belong to different classes of compounds, such as proteins or peptides and their fragments, carbohydrates, polysaccharides, sugars, lipids, or phospholipids.

In some aspects, antigens are derived from animals may cause a disease such as an infectious disease or an autoimmune disease. Antigens may be derived from, without being limited thereto, insects, such as mite (e.g. house dust mites), mosquito, bee (e.g. honey bee, bumble bee), cockroach, tick, moth (e.g. silk moth), midge, bug, flea, wasp, caterpillar, fruit fly, migratory locust, grasshopper, ant aphide, from crustaceans, such as shrimps, crab, krill, lobster, prawn, crawfish, scampi, from birds, such as duck, goose, seagull, turkey, ostrich, chicken, from fishes, such as eel, herring, carp, seabream, codfish, halibut, catfish, beluga, salmon, flounder, mackerel, cuttlefish, perch, form molluscs, such as scallop, octopus, abalone, snail, whelk, squid, clam, mussel, from spiders, from mammals, such as cow, rabbit, sheep, rat, pig, buffalo, dog, guinea pig, horse, cat, mouse, from an arthropod, such as spider, or silverfish, from worms, such as nematodes, from trichinella species, or roundworm, from amphibians, such as frogs, or from sea squirt, etc. Antigens derived from animals may also comprise antigens contained in animal products, preferably contained in animal products derived from animals as defined above, e.g. milk, eggs, meat, etc., but also from excrements or precipitates of any kind, derived from any of these animals.

Antigens derived from plants may include antigens derived from, without being limited thereto, fruits, such as kiwi, pineapple, jackfruit, papaya, lemon, orange, mandarin, melon, sharon fruit, strawberry, lychee, apple, cherry paradise apple, mango, passion fruit, plum, apricot, nectarine, pear, passion fruit, raspberry, grape, from vegetables, such as garlic, onion, leek, soya bean, celery, cauliflower, turnip, paprika, chickpea, fennel, zucchini, cucumber, carrot, yam, bean, pea, olive, tomato, potato, lentil, lettuce, avocado, parsley, horseradish, chirimoya, beet, pumpkin, spinach, from spices, such as mustard, coriander, saffron, pepper, aniseed, from crop, such as oat, buckwheat, barley, rice, wheat, maize, rapeseed, sesame, from nuts, such as cashew, walnut, butternut, pistachio, almond, hazelnut, peanut, brazil nut, pecan, chestnut, from trees, such as alder, hornbeam, cedar, birch, hazel, beech, ash, privet, oak, plane tree, cypress, palm, from flowers, such as ragweed, carnation, forsythia, sunflower, lupine, chamomile, lilac, passion flower, from grasses, such as quack grass, common bent, brome grass, Bermuda grass, sweet vernal grass, rye grass, or from other plants, such as opium poppy, pellitory, ribwort, tobacco, asparagus, mugwort, cress, etc.

Antigens derived from fungi may include antigens derived from, without being limited thereto, e.g. *Alternia* sp., *Aspergillus* sp., *Beauveria* sp., *Candida* sp., *Cladosporium* sp., *Endothia* sp., *Curcularia* sp., *Embellisia* sp., *Epicoccum* sp., *Fusarium* sp., *Malassezia* sp., *Penicillum* sp., *Pleospora* sp., *Saccharomyces* sp., etc.

Antigens derived from bacteria may include antigens derived from, without being limited thereto, e.g. *Bacillus tetani, Staphylococcus aureus, Streptomyces griseus*, etc.

One further class of antigens that may be comprise in a vaccine delivered by a recombinant Invasin comprises tumor antigens. Tumor antigens are preferably located on the surface of the (tumor) cell. Tumor antigens may also be selected from proteins, which are overexpressed in tumor cells compared to a normal cell. Furthermore, tumor antigens also include antigens expressed in cells which are (were) not themselves (or originally not themselves) degenerated but are associated with the supposed tumor. Antigens which are connected with tumor-supplying vessels or (re) formation thereof, in particular those antigens which are associated with neovascularization, e.g. growth factors, such as VEGF, bFGF etc., are also included herein. Antigens connected with a tumor furthermore include antigens from cells or tissues, typically embedding the tumor. Further, some substances (usually proteins or peptides) are expressed in patients suffering (knowingly or not-knowingly) from a cancer disease and they occur in increased concentrations in the body fluids of said patients. These substances are also referred to as "tumor antigens", however they are not antigens in the stringent meaning of an immune response inducing substance. The class of tumor antigens can be divided further into tumor-specific antigens (TSAs) and tumor-associated-antigens (TAAs). TSAs can only be presented by tumor cells and never by normal "healthy" cells. They typically result from a tumor specific mutation. TAAs, which are more common, are usually presented by both tumor and healthy cells. These antigens are recognized and the antigen-presenting cell can be destroyed by cytotoxic T cells. Additionally, tumor antigens can also occur on the surface of the tumor in the form of, e.g., a mutated receptor. In this case, they can be recognized by antibodies.

Examples of tumor antigens include, for example, 5T4, 707-AP (707 alanine proline), 9D7, AFP (alpha-fetoprotein), AlbZIP HPG1, alpha5beta1-Integrin, alpha5beta6-Integrin, alpha-methylacyl-coenzyme A racemase, ART-4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT-9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumor cell-associated extracellular matrix metalloproteinase inducer/), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CALX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumor-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor alpha 2 chain), IL-2R, IL-5, immature laminin receptor, kallikrein 2, kallikrein 4, Ki67, KIAA0205, KK-LC-1 (Kita-kyushu lung cancer antigen 1), KM-FIN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigen-A4), MAGE-A6 (melanoma antigen-A6), MAGE-A9 (melanoma-antigen-A9), MAGE-B1 (melanoma-antigen-B1), MAGE-B10 (melanoma-antigen-B10), MAGE-B16 (melanoma-antigen-B16), MAGE-B17 (melanoma-antigen-B17), MAGE-B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucos-aminyltransferase-V, Neo-PAP (Neo-poly(A) polymerase), NGEP, NMP22, NPM/ALK (nucleophosmin/anaplastic lymphoma kinase fusion protein), NSE (neuron-specific enolase), NY-ESO-1 (New York esophageous 1), NY-ESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGE-like protein-4), PAI-1 (plasminogen activator inhibitor 1), PAI-2 (plasminogen activator inhibitor 2), PAP (prostate acid phosphatase), PART-1, PATE, PDEF, Pim-1-Kinase, Pin1 (Propyl isomerase), POTE, PRAME (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumor 1), SART-2 (squamous antigen rejecting tumor 1), SART-3 (squamous antigen rejecting tumor 1), SCC (squamous cell carcinoma antigen), Sp17 (sperm protein 17), SSX-1 (synovial sarcoma X breakpoint 1), SSX-2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP-2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumor gene), or may comprise e.g. mutant antigens expressed in cancer diseases selected from the group comprising, without being limited thereto, alpha-actinin-4/m, ARTC1/m, bcr/abl (breakpoint cluster region-Abelson fusion protein), beta-Catenin/m (beta-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R170I (arginine to isoleucine exchange at residue 170 of the alpha-helix of the alpha2-domain in the HLA-A2 gene), HLA-A11/m, HLA-A2/m, HSP70-2M (heat shock protein 70-2 mutated), KIAA0205/m, K-Ras/m, LDLR-FUT (LDR-Fucosyltransferase fusion protein), MART2/m, MEl/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS-9/m, p53/m, Pml/RARa (promyelocytic leukemia/retinoic acid receptor alpha), PRDXS/m, PTPRK/m (receptor-type protein-tyrosine phosphatase kappa), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFbRII (TGFbeta receptor II), TPI/m (triosephosphate isomerase).

In some aspects, antigens for use according to the embodiments are selected from Influenza A virus (HA, NA, NP, M2, M1 antigens), influenza B virus (HA, NA antigens), respiratory syncytial virus (F, G, M, SH antigens), parainfluenza virus (glycoprotein antigens), *Streptococcus pneumoniae* (pPht, PcsB, StkP antigens), *Corynebacterium diphtheriae*,

*Clostridium tetani*, Measles, Mumps, Rubella, Rabies virus (G, N antigens), *Staphylococcus aureus* (toxin antigen), *Clostridium difficile* (toxin antigen), *Mycobacterium tuberculosis* (acute and dormant antigens), *Candida albicans*, *Haemophilus influenzae* B (HiB), poliovirus, hepatitis B virus (surface and core antigens), human papillomavirus (L1, L2, E6, E7), human immunodeficiency virus (gp120, gag, env antigens), SARS CoV (spike protein), *Staphylococcus aureus* (IsdA, IsdB, toxin antigens), Pertussis toxin, polio virus (VP1-4), Plasmodium (NANP, CSP protein, ssp2, ama1, msp142 antigens), *Staphylococcus aureus* (IsdA, IsdB, toxin), *Bordetella pertussis* (toxin), polio virus VP1-4, Plasmodium (NANP, CSP protein, ssp2, ama1, msp142 antigens)

A. Linkers

A variety of linkers can be used for linking a recombinant Invasin polypeptide and a therapeutic and/or antigenic moiety. In some aspects a linker can be a random string of one or more amino acids (e.g., 2, 3, 4, 5, 10, 15, 20 or more amino acids). Some specific linkers for use according the embodiments include the 218 (GSTSGSGKPGSGEGSTKG (SEQ ID NO:2)), the HL (EAAAK (SEQ ID NO:3)) and the G4S (GGGGS (SEQ ID NO:4)) linkers (e.g., Robinson et al., 1998; Arai et al., 2004 and Whitlow et al., 1993, each incorporated herein by reference).

In further aspects, a linker can serve as a way of separating different domains of a polypeptide construct, such as by proteolytic cleavage. For example, a linker region may comprise a protease cleavage site, such as the cleavage site recognized by an endogenous intracellular protease. In still further aspects, a protease cleavage site can be a site that is only cleaved in certain cell types (e.g., a site cleaved by a viral protease, such as HIV protease, which is only cleaved in infected cells). Example of protease cleavage site for use according to the embodiments include, without limitation, thrombin, furin (Goyal et al., 2000) and caspase cleavage sites.

The fusion proteins of the embodiments may be joined by a variety of conjugations or linkages that have been previously described in the art. In one example, a biologically-releasable bond, such as a selectively-cleavable linker or amino acid sequence may be used. For instance, peptide linkers that include a cleavage site for an enzyme preferentially located or active within a tumor environment are contemplated. For example, linkers that are cleaved by urokinase, plasmin, thrombin, Factor IXa, Factor Xa, or a metalloproteinase, such as collagenase, gelatinase, or stromelysin. In a preferred embodiment, a linker that is cleaved by an intracellular proteinase is preferred, since this will allow the targeting construct to be internalized intact into targeted cells prior to cleavage.

Amino acids such as selectively-cleavable linkers, synthetic linkers, or other amino acid sequences such as the glycine rich linkers are described above and may be used to separate proteinaceous components. In some specific examples linkers for use in the current embodiments include the 218 linker (GSTSGSGKPGSGQGSTKG (SEQ ID NO:2)) or the $G_4S$ linker (GGGGS (SEQ ID NO:3)). Additionally, while numerous types of disulfide-bond containing linkers are known that can successfully be employed to conjugate the Invasin with a cell targeting moiety, certain linkers will generally be preferred over other linkers, based on differing pharmacologic characteristics and capabilities. For example, linkers that contain a disulfide bond that is sterically "hindered" are to be preferred, due to their greater stability in vivo, thus preventing release of the toxin moiety prior to binding at the site of action.

B. Conjugates

Additionally, any other linking/coupling agents and/or mechanisms known to those of skill in the art can be used to combine the components of the present embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is contemplated that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Thorpe et al., 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (e.g., arginine or lysine) followed by a proline, and is characterized by greater stability and reduced aggregation. U.S. Pat. No. 5,880,270 discloses aminooxy-containing linkers useful in a variety of immunodiagnostic and separative techniques.

IV. ADMINISTRATION AND PHARMACEUTICAL COMPOSITIONS

In some embodiments, an effective amount of a recombinant Invasin polypeptide or a polynucleotide encoding the recombinant Invasin and, optionally, a therapeutic moiety is administered to a cell. In other embodiments, a therapeutically effective amount of the composition comprising a recombinant Invasin and a therapeutic moiety is administered to an individual for the treatment of disease.

In some embodiments, the Invasin variants of the present disclosure can be used to deliver pharmacologically active substances, therapeutic substances, cytotoxic substances, diagnostic substances, etc., herein after commonly referred to as pharmacologically active substances, into cells. When used in this aspect of the present disclosure, the Invasin variant may be, but need not be, linked to the pharmacologically active substance. If desired, pharmacologically active substances can be linked to Invasin variants either by the production of fusion proteins or by coupling the pharmacologically active substance to the recombinant Invasin protein either directly or through the use of a linker. Pharmacologically active substances can be coupled to either the amino- or carboxy-terminus of the recombinant Invasin polypeptides of the present disclosure. For example, drug conjugates wherein the carboxy terminus of a recombinant Invasin protein is linked to a pharmacologically active substance can be prepared by the use of an active ester of the desired pharmacologically active substance in the presence of a dehydrating agent. Alternatively, a functional linker can be placed between the recombinant Invasin protein and the pharmacologically active substance.

In some embodiments, there is provided an adjuvant composition comprising the recombinant Invasin proteins of the present disclosure in a physiologically acceptable solution. An example of a preferred adjuvant composition of the present disclosure is the recombinant IpaC protein purified with a His-Tag® moiety, diluted into PBS, and further dialyzed against several volumes of PBS to remove the remaining denaturant. Preferably, the adjuvant composition comprises a recombinant Invasin protein of at least 95% purity and more preferably of at least 97% purity. The adjuvant may be used alone as a vaccine in order to convey immunity against the organism of the wild type protein from which the protein is derived, or against a closely related organism. The adjuvant compositions of the present disclosure may also be advantageously used, alone or in combination with an antigen, to stimulate the immune response of individuals who are immunologically compromised because of age or immuno-suppression, or for other immuno-therapeutic uses for immuno-stimulatory compounds which have been described in the art, such as immunotolerization (see Czerkinsky et al., *Ann. N.Y. Acad. Sci.*, 778:185-193, 1996). The immune response stimulated can involve T cells, B cells or both. When used for this purpose in combination with an antigen, the ratio of antigen to recombinant Invasin protein is preferably about one part antigen to about 0.0001 to about 10,000 parts recombinant Invasin protein, more preferably about one part antigen to about 0.001 to about 1,000 parts recombinant Invasin protein and most preferably about one part antigen to about 0.01 to about 100 parts recombinant Invasin protein.

The recombinant Invasin polypeptides of the present disclosure may be mixed with antigens of biological or chemical origins to form a vaccine, and then administered to an animal to elicit an immune response to the antigen, as shown in the following examples. The immune response to the antigen can involve T cells, B cells or both. The antigen may be an infective agent, or a subunit thereof, or may be a biologically active chemical or toxoid. An infective agent can be a bacterium, virus, retrovirus, protozoan, parasite or fungus. For example, the vaccine may comprise antigens to gastro-intestinal pathogens, such as norovirus, shigella, or cholera. Such a vaccine formulation, comprising recombinant Invasin protein and an antigen of interest, is considered another aspect of the present embodiments. The recombinant Invasin protein is also preferably combined with the antigen in a ratio of about one part antigen to about 0.0001 to about 10,000 parts purified recombinant Invasin protein. More preferably, the recombinant Invasin protein is preferably combined with the antigen in a ratio of about one part antigen to about 0.001 to about 1,000 parts Invasin protein. Most preferably, the recombinant Invasin protein is preferably combined with the antigen in a ratio of about one part antigen to about 0.01 to about 100 parts Invasin adjuvant protein.

The Invasin variant and the pharmacologically active substance may be administered to a subject per se or in the form of a pharmaceutical composition for the treatment of cancer, autoimmunity, transplantation rejection, post-traumatic immune responses and infectious diseases, for example by targeting viral antigens, such as gp120 of HIV. Pharmaceutical compositions comprising the proteins of the embodiments may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

In particular aspects, the Invasin variant and the pharmacologically active substance are delivered to cells in the intestine, such as microfold (M) cells. For example, oral vaccine may be administered by conjugation of the vaccine to a high affinity recombinant Invasin of the present disclosure for enhanced systemic bioavailability of the oral vaccine.

In specific embodiments, systemic formulations of the Invasin variant and the pharmacologically active substance are contemplated. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

A. Effective Dosages

The Invasin variant and/or the pharmacologically active substance of the embodiments will generally be used in an amount effective to achieve the intended purpose. For use to treat or prevent a disease condition, the molecules of the embodiments, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with compositions the embodiments include, but are not limited to, steroid and non-steroid anti-inflammatory agents.

The carrier component of the pharmaceutical compositions of the present disclosure may include polymeric microparticles or nanoparticles of different materials and of very different sizes. Such particles may have a membrane-walled form, in which the core material is concentrated as a reservoir, or a matrix form in which core material is uniformly dispersed. A variety of suitable materials exist ranging from non-degradable polymers, to biodegradable synthetic polymers, to modified natural products such as gums, starches, proteins, fats and waxes (Sidhu and Weiss, 2004). The carriers may also include non-toxic, non-therapeutic components, such as liposomes, starburst polymers, microspheres, microemulsions, nanocapsules or macroemulsions to facilitate formulation, delivery, controlled release or sustained action of the therapeutic composition.

B. Pharmaceutical Compositions

Pharmaceutical compositions of the present embodiments comprise an effective amount of one or more Invasin variants and at least one pharmaceutically active substance dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of a pharmaceutical composition that contains one or more Invasin variants and at least one pharmaceutically active substance will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

The recombinant Invasin and therapeutic moiety may comprise different types of carriers depending on whether it is to be administered in solid, liquid or aerosol form, and whether it need to be sterile for such routes of administration as injection. The present therapies of the embodiments can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present embodiments administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In embodiments where compositions are provided in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

In one embodiment of the present disclosure, the carrier component of the pharmaceutical composition is a liposome. In an alternate embodiment, the carrier component may be based upon proteinoid technology and consist of various amino acids.

Liposomes are most frequently prepared from phospholipids, but other molecules of similar molecular shape and dimensions and having both a hydrophobic and a hydrophilic moiety can be used. All such suitable liposome-forming molecules are referred to herein as lipids. One or more naturally occurring and/or synthetic lipid compounds may be used in the preparation of the liposomes. Liposomes may be anionic, cationic or neutral depending upon the choice of the hydrophilic group. For instance, when a compound with a phosphate or a sulfate group is used, the resulting liposomes will be anionic. When amino-containing lipids are used, the liposomes will have a positive charge, and will be cationic liposomes. In addition, the pharmaceutical compositions of the present disclosure may include liposome carriers wherein the invasive protein has been incorporated into the liposome bilayer. Representative suitable phospholipids or lipid compounds for forming liposomes include, but are not limited to, phospholipid-related materials such as phosphatidylcholine (lecithin), lysolecithin, lysophosphatidylethanol-amine, phosphatidylserine, phosphatidylinositol, sphingomyelin, phosphatidyl-ethanolamine (cephalin), cardiolipin, phosphatidic acid, cerebrosides, dicetylphosphate, phosphatidyl-choline, and dipalmitoyl-phosphatidylglycerol. Additional nonphosphorous-containing lipids include, but are not limited to, stearylamine, dodecylamine, hexadecyl-amine, acetyl palmitate, glycerol ricinoleate, hexadecyl stearate, isopropyl myristate, amphoteric acrylic polymers, fatty acid, fatty acid amides, cholesterol, cholesterol ester, diacylglycerol, diacylglycerolsuccinate, and the like. In another embodiment of the present disclosure, the therapeutic agent and the transporting ligand might be incorporated together through a polymeric carrier. For example, the polymeric carrier may be a polymer chain. The list of suitable synthetic polymers includes; poly(ethylene glycol), N-(2-hydroxypropyl)methacrylamide and polyvinyl polymers in particular. Other potential polymeric carriers are polypeptide carriers, such as poly(a amino acids), including poly($\alpha$-L-lysine), poly(N^-hydroxypropyl-L-glutamine), poly(L-aspartic acid). In addition, naturally occurring proteins (albumin, immunoglobulins and lectins), and polysaccharides (dextran and charged derivatives) can be used as carriers. The therapeutic and/or the transporting ligand may be attached to the polymer chain through various reactive side chains that may or may not be degradable in vivo.

The carrier may be selected or modified to bind the transport enhancer (i.e., the recombinant Invasin) and or the therapeutic agent either through simple absorption, an ionic interaction or covalent linking. Preferably, the carrier is also able to incorporate large amounts of the therapeutic agent in an active form. The carrier component as well as the therapeutic agent associated with the carrier should be stable in the gut environment, but the carrier may also be selected or modified to release the therapeutic agent once it has been transported across the mucosal barrier. The release of the therapeutic agent may be effectuated by degradative means, such as a cleavable bond, or by degradation of the carrier component. Examples of such release mechanisms may include stabilized Schiff base linkages, acid-cleavable linkages or oligonucleotide sequences cleaved by serum factors.

The compositions of the present disclosure are typically formed by attaching the transport enhancer either directly to the therapeutic agent or to a carrier system. Because the bacterial adhesion proteins described in the present disclosure bind cell receptors, the method of attachment must not prevent the binding of the bacterial protein to the receptor. This can be tested beforehand on in vitro systems containing the appropriate receptors, such as membrane preparations or cell systems.

Various conjugation techniques are known in the art, and the following conjugation techniques are provided by way of illustration. Other conjugation techniques can also be used when appropriate as will be appreciated by those skilled in the art. Where the therapeutic agent is a protein, conjugation may be carried out using bifunctional reagents which are capable of reacting with each of the proteins (i.e., the therapeutic protein and the transport enhancer protein) thereby forming a bridge between the two components. Covalent attachment of the transport enhancer to either the therapeutic agent or the carrier system, through either the available amine or carboxy groups of the transport enhancer, may be carried out using suitable conjugation reagents including; glutaraldehyde and cystamine and EDAC. Other known conjugation agents may be used, as long as they provide linkage of the transport factor without denaturing the protein. One preferred method of conjugation involves thiolation wherein the transport protein is treated with reagents such as N-Succinimidyl 3-(2-pyridyldithio) proprionate (SPDP) to form a disulfide bridge with another sulfhydryl group either in the therapeutic agent or on the carrier. Spacers might also be used and could include polymer chains such as polyethylene glycol, a sugar or a peptide sequence. Alternatively, the transport enhancer could be attached through a simple absorption method as described in a following Examples. In yet another embodiment, the compositions of the present disclosure can be in the form of a fusion protein made by recombinant DNA techniques. Thus, one of ordinary skill can duplicate or mimic bacterial proteins which are suitable as transport enhancers. The use of recombinant DNA techniques requires knowledge of the nucleic acid sequence of the polypeptide or protein therapeutic agent to be delivered. The nucleic acid fragment corresponding to the therapeutic agent is linked to a nucleic acid fragment corresponding to the chosen transport enhancer, thereby forming a recombinant molecule. The recombinant molecule is then operably linked to an expression vector and introduced into a host cell to enable expression of a polypeptide of the present embodiments. When the carrier component of the pharmaceutical composition is also an amino acid sequence, for example a polymer chain, the entire pharmaceutical composition may be produced by recombinant techniques.

The suitability of the resultant pharmaceutical composition as an oral or topical dosage form can be tested following the protocols set forth in the following Examples. Compositions which are formulated based upon the description of the present disclosure will be administered to subjects at a dosage range determined by a skilled investigator or attending physician based upon known and accepted parameters. The dosage regimen involved for a particular therapeutic agent may be determined empirically, and making such determinations is within the skill in the art. Prior to administering the agent, it is preferable to determine toxicity levels of the therapeutic agent (s) so as to avoid deleterious effects. Other considerations will include various factors which modify the action of drugs, e.g., the age, condition, body weight, sex and diet of the patient, the nature and severity of the condition as well as any complicating illness, time of administration and other clinical factors. Optimal dosages of the drug of interest can be determined by one of ordinary skill in the art using conventional techniques. As a general rule, the dosage levels will correspond to the accepted and established dosage for the particular therapeutic agent to be delivered, i.e., the dosage will be adjusted to attain clinical equivalence and/or bioequivalence to the parenteral dosage form of the therapeutic agent, or correspond to the dosage that achieves the desired physiological or therapeutic response.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Expression & Purification of Soluble Invasin Variants

To compare the integrin binding abilities of different Invasin variants, the C-terminal domains of Invasin (D1D5 or D4D5) were expressed as maltose binding protein (MBP) fusion proteins in the *E. coli* cytoplasm, as previously described (Panthani et al., 2013; Leong et al., 1995). The D1D5 domains were amplified from plasmid pRI203 using primers

```
                                              (SEQ ID NO: 5)
5'-agctatcGAGCTCgaactcattcacattgagcgtc-3'
and
                                              (SEQ ID NO: 6)
5'-cgtcattataCCATGGctagttaatcattatattgacagcgcacag
ag-3'
```

(restriction sites in uppercase and underlined), and cloned into vector pMAL-c5x (NEB) using SacI and NcoI sites to generate plasmid pTAK035 (MBP-D1D5). Domains D1-D3 were deleted using PCR-based plasmid mutagenesis, as above, to create plasmid pTAK039 (MBP-D4D5). Invasin variants selected from mutagenic libraries were either subcloned into pMAL-c5x or generated by site-directed mutagenesis of pTAK035 or pTAK039.

The pTAK035 plasmid was transformed into *E. coli* strain Origami B to support formation of the di-sulfide bond in the D4-D5 region during cytoplasmic expression. To enhance yields, the 17 kDa Skp chaperone was co-expressed cytoplasmically from a compatible vector, pAR3-Skp, without its native periplasmic leader sequence (Levy et al., 2001). Starter cultures grown in LB with ampicillin (150 µg/ml), chloramphenicol (34 µg/ml), kanamycin (15 µg/ml), tetracycline (12.5 µg/ml), 0.2% glucose were sub-cultured into 250 ml of Terrific Broth (TB) containing the same additives. After about 16 hours growth at 37° C., the cells were harvested and resuspended in fresh TB with antibiotics, but without glucose, and shaken at 25° C. and 225 rpm. After 30 min, arabinose was added to a final concentration of 0.2% to induce the expression of Skp; after another 30 min, IPTG was added at a final concentration of 1 mM to induce the Invasin expression for another 4 to 5 hours.

Cells were then harvested, resuspended in Buffer A (50 mM Hepes, 200 mM NaCl pH 7.4), and lysed with a French Press (Thermo Electron). To minimize degradation, complete protease inhibitor tablets (Roche) were immediately added and the cell lysate clarified via centrifugation for 20 min at 20,000 RPM and filtration through a 45 µm filter (Millipore). The supernatant was applied to an MBPTrap column on an ÅKTA FPLC (GE healthcare), followed by elution with Buffer B (Buffer A+10 mM maltose). The eluent was further purified by size exclusion chromatography using a Superdex 75 (MBP-D4D5 constructs) or 200 column (MBP-D1D5 constructs; GE Healthcare) with Buffer A as running buffer. Protein purity was analyzed by SDS-PAGE.

Relative Surface Density of Invasin on the *E. coli* Surface

To present the native Invasin protein on the *E. coli* outer membrane, the intact Invasin gene was cloned into the pBAD plasmid. The Invasin gene was PCR amplified from plasmid pRI203[5] using primers

```
                                              (SEQ ID NO: 7)
5'-taactgacgaTCTAGAacttttaagaaggagatataccatgatggtt
ttccagcc-3'
and
                                              (SEQ ID NO: 8)
5'-tacgatgtctaatgtatGCATGCtcaattattcattatattgacag
cgcacag-3',
``` digested with XbaI and SphI (NEB) and ligated into the similarly digested pBAD30 vector (Guzman et al., 1995) to create plasmid pTAK020. Individual alanine substitutions at positions D881, Y860, Y863, Y878, R883, Y885, D911 and Y976 were introduced using QuickChange-type mutagenesis. Plasmids encoding intact Invasin variants were transformed into *E. coli* BL21(DE3) cells. Starter cultures grown in TB broth with ampicillin (150 µg/ml) and 2% glucose at 37° C. were diluted into fresh media at an $OD_{600}$=0.05. Cells were grown for two hours ($OD_{600}$~0.4-0.8) at 37° C., arabinose was added to a final concentration of 0.2%, and cells were grown for an additional two hours.

Analysis of *E. coli* Surface-Displayed Invasin Variants Via Flow Cytometry

Flow cytometry with the 3A2 anti-Invasin monoclonal antibody (Isberg and Leong, 1990) was used to assess the relative levels of Invasin on the bacterial surface. Specifically, $10^7$ cells were harvested and resuspended in 100 µL staining buffer (PBS-1% BSA) with 2 µg/mL 3A2 antibody. After 30 minutes incubation on ice, cells were washed twice with staining buffer and resuspended in 100 µL of 1:200 APC-conjugated goat anti-mouse IgG, Fc-specific, (Becton-Dickinson) or 1:100 Cy5-conjugated goat anti-mouse IgG (Invitrogen) antibody for an additional 30 minutes. After two wash steps, cells were analyzed on an LSRF ortessa (Becton-Dickinson).

To assess Invasin $\alpha_5\beta_1$ integrin-binding activity, FACS was used with fluorescently-labeled or biotinylated integrin. For fluorescent labeling of integrin and *E. coli* staining, Alexa Fluor 647 (Invitrogen) was dissolved in acetonitrile at 1 mg/ml, aliquoted in 50 µg fractions, dried and stored at −20° C. A 50 µg aliquot of $\alpha_5\beta_1$ integrin (R&D Systems), was adjusted to 1 mM sodium bicarbonate and combined with 20 µL dye solution (prepared from 50 µg Alexa Fluor 647 dissolved in 5 µL of dimethylformamide plus 45 µL of 1 M sodium bicarbonate). The reaction was allowed to proceed for 1.5 hours with rotation at room temperature, after which the solution was dialyzed against integrin buffer (50 mM HEPES, 200 mM NaCl, 2 mM $MnCl_2$ pH 7.5) using a 20 KDa molecular weight cut off dialysis cassette (Pierce) to remove unreacted dye. To prevent photobleaching, all steps proceeded in the dark. *E. coli* cells expressing Invasin ($1\times10^8$ cells) were pelleted and resuspended in 25 µL integrin buffer (50 mM HEPES, 200 mM NaCl, 2 mM $MnCl_2$ pH 7.5) with 4% BSA, followed by addition of 25 µL of a 200 nM labeled $\alpha_5\beta_1$ in integrin buffer and incubation of 30 min at room temperature. For biotinylation of integrin and *E. coli* staining, a 100-fold molar excess of EZ-Link Sulfo-NHS-LC-Biotin (Thermo Scientific) was added into $\alpha_5\beta_1$ integrin in PBS and incubated at room temperature for 1-3 h before quenching with 1M Tris (pH 8.0) and dialyzing against PBS overnight in 4° C. *E. coli* cells expressing Invasin ($1\times10^7$ cells) were added into 100 µL of 42 nM biotinylated $\alpha_5\beta_1$ integrin in staining buffer (50 mM HEPES, 150 mM NaCl, 2 mM $MnCl_2$ pH 7.5 with 1% BSA). After 30 min incubation on ice and one wash with staining buffer, the cells were stained with 1:200 PE-conjugated streptavidin (BioLegend). Before flow cytometric analysis, cells were resuspended in 1 mL of integrin buffer. All cytometry data were analyzed using FlowJo software and all experiments were performed at least twice with replicate cultures to assess variation due to growth and induction steps.

Invasion of Caco-2 Cells by *E. coli* Expressing Invasin Variants

The Caco-2 invasion assays were performed as previously described (Critchley-Thorne et al., 2006). Briefly, BL21 (DE3) cells were co-transformed with two plasmids: a pBAD30 plasmid encoding a surface-displayed Invasin variant and a pET28 plasmid encoding green fluorescent protein (GFP) as a reporter molecule to track bacterial adhesion and internalization. Bacterial cultures were grown as above, except that Invasin expression was induced with 0.2% arabinose at 37° C. for one hour prior to induction of GFP with 1 mM IPTG for an additional hour at 37° C.

Caco-2 cells (ATCC HTB-37; passages between P23-P33) were seeded at a density of 104/cm2 in complete media (DMEM) supplemented with MEM nonessential amino acids (Mediatech), penicillin/streptomycin (Gibco), GlutaMAX (Gibco), and 10% fetal bovine serum (Gibco) and placed in a CO2 incubator (5%) for two days. Immediately prior to assay, the Caco-2 cells were washed twice with DMEM without supplements, then provided infection media (complete growth medium with heat-inactivated FBS, 200 ug/mL ampicillin, 50 ug/mL kanamycin, without penicillin/streptomycin). Bacteria were added to the cultures at a multiplicity of infection of 70 and allowed to incubate for 1.5 hours at 5% CO2 and 37° C. Next, the Caco-2 cells were washed three times with plain DMEM and three times with PBS to remove non-adherent *E. coli*. CHO-K1 cells were grown similarly except without pyruvate, nonessential amino acids, or GlutaMAX in growth media.

For internalization assays, the cells were incubated in infection media with gentamicin (25 ug/ml) overnight to kill extracellular bacteria. The next day, the Caco-2 cells were trypsinized, washed with PBS and resuspended in PBS+1% FBS for FACS analysis (LSRFortessa). For adhesion assays, the Caco-2 or CHO-K1 cells were analyzed without overnight incubation in gentamycin. Under both conditions, the eukaryotic cell population exhibited a bimodal distribution, with high and low fluorescent populations. The percentage of the higher fluorescence population is reported as % (invasion or adhesion); the population with lower fluorescence overlapped with uninfected cells. The % GFP-positive cells are reported instead of mean fluorescence intensity (MFI) so that the results are not obscured by bacterial growth after adhesion.

To test the adhesion for CHO variants with different integrin profiles, CHO-B2 cells, lacking α5 integrin22, were cultured in DMEM supplemented with 10% FBS, 1% antibiotics-antimycotics, 1% L-glutamine, 1% non-essential amino acids, and 1% sodium pyruvate; while CHO-B2 cells with stably transfected a5 integrin (CHO-B2+X5C5, here called CHO-B2+α5) were cultured with 250 µg/mL G418; CHO-B2 cells with stably transfected αvβ3 integrin (CHO-B2+αvβ3) were cultured with 500 µg/mL zeocin; CHO-B2 cells with stably transfected α5 and αvβ3 integrin (CHO-B2+α5+αvβ$_3$) were cultured with both G418 and zeocin 23. Cells were seeded at 4×104/cm2 in respective medium 24-48 hrs before conducting the adhesion assays, which were performed as above.

Confocal Microscopy

Confocal microscopy was used to directly visualize the location and number of *E. coli* after incubation with Caco-2 and CHO-K1 eukaryotic cells. The incubation steps to detect adherent and internalized or only internalized bacteria were performed as above, with the exception that eukaryotic cells were grown on coverslips. Caco-2 cells were seeded on poly-lysine coated coverslips at a density of $2\times10^4/cm^2$ in 6-well plates two days prior to the assay; CHO-K1 cells were seeded on untreated coverslips at the same density. After incubation with *E. coli* at an MOT of 70 for 1.5 hr or overnight, the coverslips were washed six times with media to remove free *E. coli*. Next, 1 mL of 1:1000 CellMask DeepRed (Life Technologies) diluted in DMEM was added for 5 min at 37° C. to visualize the cell membrane. Then the staining solution was removed and cells were fixed with 1% formaldehyde in PBS and incubated at 37° C. for 10 min. After three washes with PBS, the coverslips were mounted on glass slides with Fluoromount-G (SouthernBiotech) and imaged on Zeiss LSM700 confocal microscope.

Generation of Site-Saturation Mutagenesis Libraries

Four libraries were created, each with a theoretical library size of ≤3-6×10$^6$ in order to allow for complete experimental sampling of the library. This was achieved by randomizing a small number of residues in each library (ten or fewer) and by using a soft randomization procedure to preserve physicochemical properties, which may be important for folding or stability. All libraries were designed to allow for sampling of the wild-type sequence of Invasin. Library 1, with a theoretical library size of 3.98×10$^6$, was created with degenerate oligonucleotides randomizing only the following codons: 844(KHT), 847(VAK), 858(NTT), 859(WMC), 860 (KHT), 861(MAW), 862(RSC), 863(KHT), 864(KHT), and 865(GAW). Library 2, with a theoretical library size of 5.31×10$^6$, used: 878(KHT), 870(KHT), 880(NTT), 881 (KHT), 882 (TMT), 883(MRM), 884 (NTT), 885 (KHT), 887 (MAS), and 888(MRG). Library 3, with a theoretical library size of 4.19×10$^6$, used: 809(NNS), 810(NNS), 811 (NNS), 812(NNS), and 814(NTT). Library 4, with a theoretical library used: 908(NWW), 909(NNC), 910(NNC), 911(KHT), 912(NNS), and 913(KMT).

The libraries were generated using a modified protocol from Sidhu and Weiss[24]. Briefly, inactive Invasin templates were created by introducing stop codons or frame shift mutations into the regions targeted for mutagenesis. The templates were transformed into *E. coli* strain CJ236 and infected with M13KO7 helper phage in media with uridine to isolate uracil-containing single-stranded plasmid DNA (dU-ssDNA). The four separate libraries were each created by annealing the mutagenic primer to dU-ssDNA templates in the presence of T4 ligase and T7 polymerase to generate double-stranded heteroduplex DNA which was transformed into electrocompetent MC1061 cells. In all cases, the numbers of transformants were ~10-fold greater than the predicted library sizes. Colonies were scraped from plates, the cell concentration measured by absorbance at 600 nm, adjusted to 15% glycerol and frozen at −80° C.

Selection of Invasin variants

In order to select for Invasin variants able to both target and invade M cells, a dual selection approach was employed using MC1061 bacterial cells with displaying Invasin. Each library underwent two rounds of Caco-2 cell panning, followed by 2-4 rounds of FACS based selection with fluorescent integrin. Finally, 6-10 clones from each round were sequenced to assess the sequence convergence.

The first Caco-2 selection round recovered all bacterial cells either adhering to or internalized by Caco-2 cells, while the second more stringent round only recovered internalized bacteria by using gentamycin to kill extracellular bacteria. Bacterial cultures were grown as above, using a 100 µL aliquot of frozen library to seed a starter culture, followed by growth and expression in a 20 ml culture. The Caco-2 cells were washed and prepared as above, before adding 3×10$^9$ bacteria at a multiplicity of infection (MOI) ~800 for two hours at 5% $CO_2$, 37° C. Next, the Caco-2 cells were washed with media to remove unbound bacteria. To lyse Caco-2 cells and recover internalized bacteria, about 6 ml of LB with ampicillin (150 ug/ml) and 1% Triton X100 was added to the flask for 10 minutes. The flasks were then scraped and the contents transferred to microfuge tubes, washed to remove Triton X-100, and transferred to 20 ml of TB with ampicillin and 2% glucose for overnight growth at 37° C.

For the second Caco-2 selection round, 1×10$^9$ bacterial cells grown after round one were inoculated into 20 ml of fresh LB with ampicillin, for expression and infection as above. After two hours infection at an MOI ~800, the flask of infected Caco-2 cells, were washed with media, followed by overnight incubation in infection medium with gentamycin. The next day, bacterial cells were recovered as above with a fraction plated for sequence analysis. Overnight cultures were either sub-cultured for subsequent FACS-based selection or frozen.

For the third selection round using integrin labeling and FACS selection, bacterial cells grown from round two were sub-cultured and induced. Bacteria (~1×10$^8$) were labeled with fluorescent $\alpha_5\beta_1$ at concentrations ranging from 100 nM-250 nM as above, and sorted on an FACSAria (Becton-Dickinson) Cells were diluted in integrin buffer to reach a sorting rates of 1,000-5,000 events per second. The forward scatter and side-scatter thresholds were adjusted to remove debris. A size gate was set to encompass ~90% of events. Initial sorting rounds were less stringent and sorted 3-5% of the most fluorescent events, while later sorting rounds became more restrictive, collecting only the top 0.5-1%. Fractions of collected cells were plated for single colony FACS and sequence analysis. The remaining cells were grown overnight and the sorting process repeated one to three times. Single clones were analyzed as above.

Invasin-Integrin Binding Affinity and Specificity

To assess the relative affinity of Invasin variants and fibronectin for select integrins, ELISA plates (Costar) were coated with recombinant human integrin $\alpha_5\beta_1$, $\alpha_v\beta_1$, or $\alpha_v\beta_3$ extracellular domains (R&D systems) in PBS at ~1 µg/mL overnight at 4° C. Coated plates were washed with washing buffer (50 mM HEPES, 200 nM NaCl, 2 mM $MnCl_2$, 0.05% Tween20) and blocked with 5% PBST-milk with 2 mM $MnCl_2$ or 2% BSA in washing buffer. The addition of 2 mM $MnCl_2$ was essential to support Invasin-integrin binding and increases fibronectin binding (Saltman et al., 1996). Purified Invasin variants (MBP-D1D5 or MBP-D4D5) or glutathione-S-transferase (GST)-fibronectin III (Palumbo and Wang, 2006; Panthani et al., 2013; Fairman et al., 2012) (KeraFast) were titrated on the plates starting from 1000 nM in blocking buffer and allowed to equilibrate for 1.5 hours. Plates were washed 3 times, and incubated with 1:3333 HRP-conjugated anti-MBP monoclonal antibody (NEB) to detect Invasin variants or anti-GST-HRP (ThermoFisher) to detect fibronectin for 1 hour. Plates were washed a final time prior to the addition of TMB substrate (Pierce), quenched with 1N HCl and the absorbance measured at 450 nm. Data were fit to a 4-parameter logistic equation (GraphPad).

Binding affinities for $\alpha_5\beta_1$ integrin were compared by surface plasmon resonance (SPR) using a BIAcore 3000 (GE Healthcare) as previously reported (Swiatkowska et al., 2008). Briefly, the $\alpha_5\beta_1$ integrin (R&D Systems) was covalently attached via NHS/EDC chemistry to a CMS chip by injecting 20 µL of 10 µg/mL integrin in 50 mM citrate pH 3.9. All experiments were performed at 25° C. using a running buffer of 50 mM Hepes, 200 mM NaCl, 1 mM $MnCl_2$ pH 7.5, and flow rate of 30 µL/min. Wild-type, RGD844 and D911A Invasin variants expressed as MBP-D1D5 fusions were injected at 1000 nM for a total volume of 60 µL and allowed to dissociate for 400 seconds. The surface was regenerated by successive injections of running buffer with 50 mM EDTA.

Biophysical Analyses of Invasin Variants

The melting temperature of purified MBP-D1D5 Invasin was assessed using differential scanning fluorimetry at 3.2 mg/ml and Sypro Orange (1:6,000 dilution). The solution temperature was gradually increased (1° C./min) and the fluorescence was recorded using an ABI 7900HT Fast Real-Time PCR System, with the inflection point of two-state unfolding recorded as the melting temperature. Circular dichroism measurements were obtained with a Jasco-J815 CD Spectrometer from 260 nm to 185 nm (1 nm increments) in a 5 mM phosphate buffer.

Surface Integrin Expression on CHO-K1 and Caco-2 Cells

To compare the integrin expression profiles of CHO-K1 and Caco-2 cells, cells were washed three times with PBS, and detached with Accutase (BD) at room temperature for 10 min to preserve the surface integrins. Next, 3×10$^5$ cells were stained with 1 µg of anti-$\alpha_5\beta_1$ (MAB1969, Chemicon) or anti-$\alpha_v\beta_3$ (MAB1976, Chemicon) antibodies or isotype control in 100 µL final volume for 30 min on PBS wash steps, the cells were stained with Allophycocyanin (APC)- conjugated anti-mouse IgG antibody for 30 min on ice. Then the cells were washed twice more and analyzed by cytometry with an LSRFortessa.

Example 2—Results

Expression of Active Invasin Domains in *E. coli*

In order to engineer Invasin and characterize the resulting variants, it was desirable to have both a soluble expression system and a display system suitable for directed evolution. Notably, the C-terminal domains four and five (D4D5) comprise the minimal receptor binding protein, while the complete extracellular protein, consisting of domains one through five (D1D5) weakly homodimerize, mediated by domain D2 (Dersch and Isberg, 2000). As both versions have been expressed recombinantly and have been shown to support receptor binding and internalization (Leong et al., 1990; Isberg et al., 1993), the D1D5 (residues 503-986) and D4D5 (residues 795-986) fragments downstream of the *E. coli* maltose binding protein were cloned (FIG. 1A). A variant with the D911A substitution, known to severely compromise integrin binding, was cloned as a control.

Figure 1B:
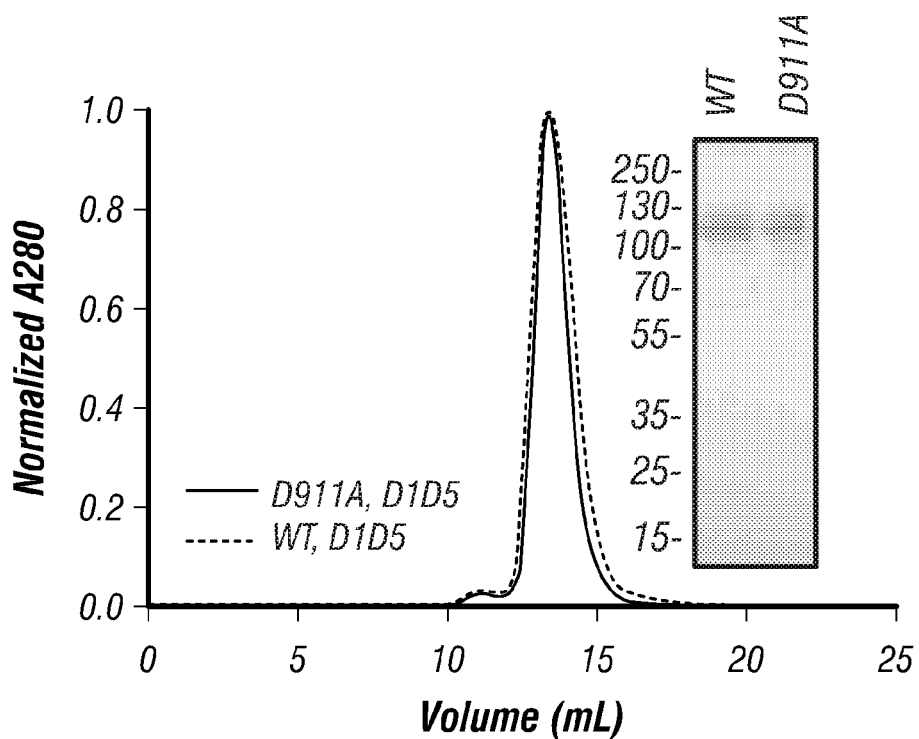
Figure 1C:
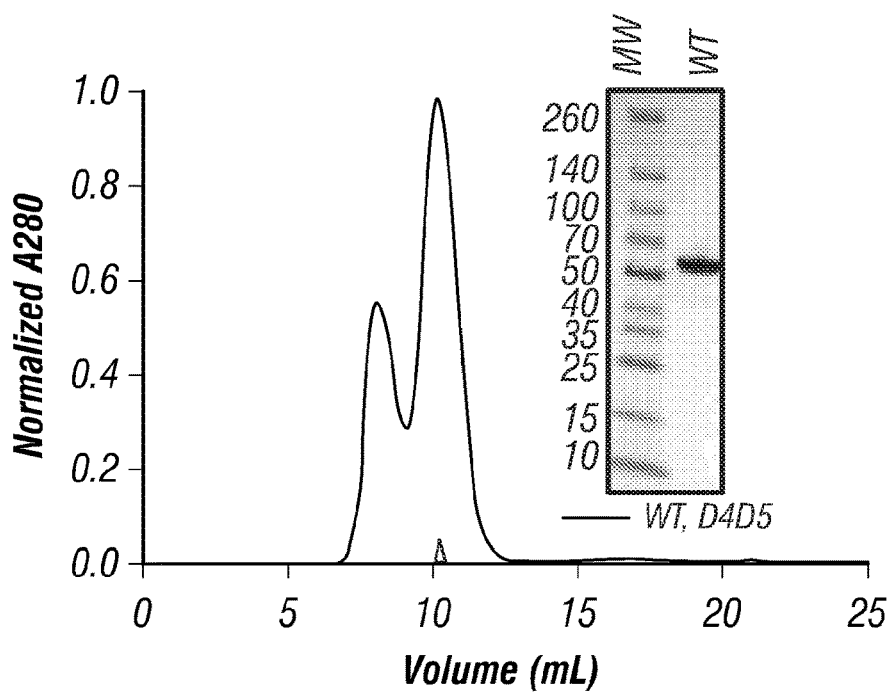

Cytoplasmic expression in *E. coli*, with co-expression of the Skp chaperone from a compatible plasmid, followed by maltose affinity and size exclusion chromatographic steps resulted in highly pure protein preparations of up to 100 mg/L for the MBP-D1D5 and MBP-D4D5 versions (FIGS. 1B, 1C). The observed molecular weight is about 145 kDa for MBP-D1D5, which is intermediate to the predicted sizes for monomer and dimer (94 kDa and 188 kDa, respectively). This may reflect slow migration of monomers of the rod-like protein, as the D1D5 construct has been reported to purify as a monomer (Dersch and Isberg, 1999; Hamburger et al., 1999; Dersch and Isberg, 2000).

Figure 1D:
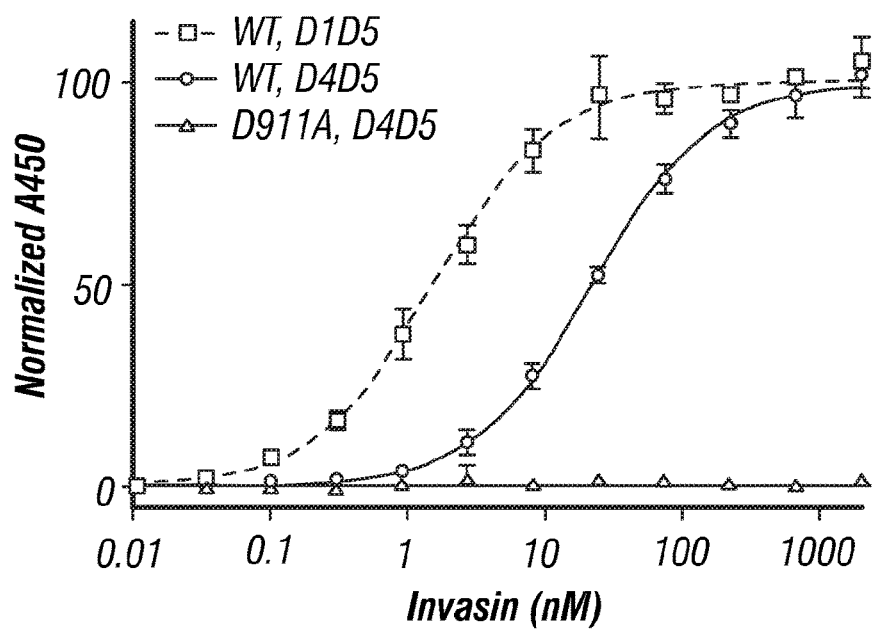
Figure 2A:
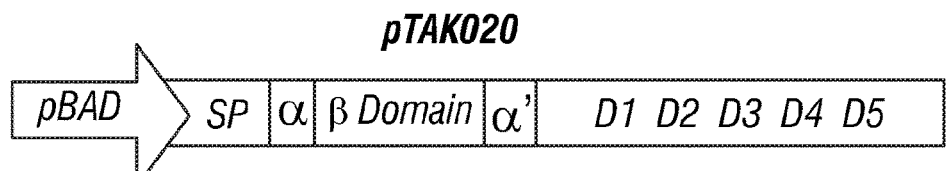
FIGS. 2A-2C—Expression of active Invasin on the E. coli surface. 2A, To display Invasin on the surface of E. coli BL21(DE3) cells, the plasmid pTAK020 was constructed by inserting the complete Invasin gene, including signal sequence, into the pBAD30 plasmid under an arabinose inducible promoter. 2B, After induction of pTAK020, E. coli cells present Invasin on their surface. Invasin was detected by the anti-Invasin murine antibody 3A2 followed by anti-mouse-Alexa647 using flow cytometry. The wild-type Invasin (dashed line) and the D911A variant (solid black line) are readily detected; cells incubated without the 3A2 antibody (gray line) or cells with control pBAD30 plasmid lacking the Invasin gene have low fluorescence. 2C, To assess integrin binding activity of E. coli-displayed Invasin, bacteria were labeled with biotinylated $\alpha_5\beta_1$ integrin followed by streptavidin-PE and again analyzed by flow cytometry. Shown are wild-type Invasin (dashed line), the D911A variant (black line), and cells with plasmid lacking the Invasin gene (gray line). In both cases, counts are shown on the y-axis.
Figure 2B:
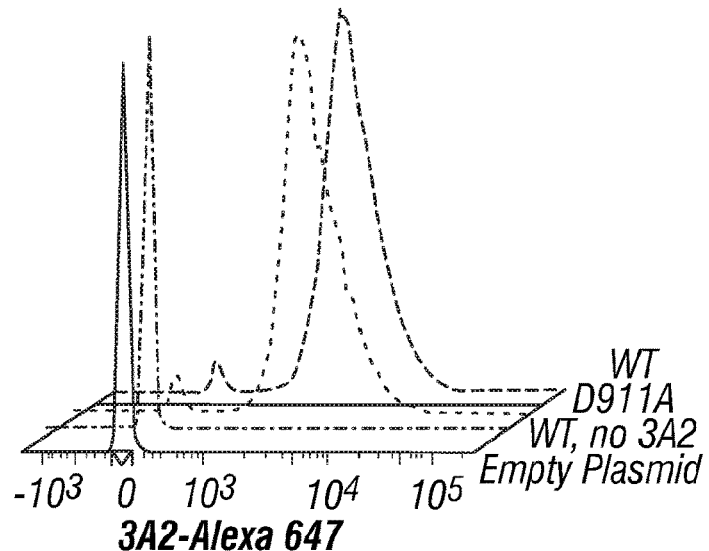
Figure 2C:
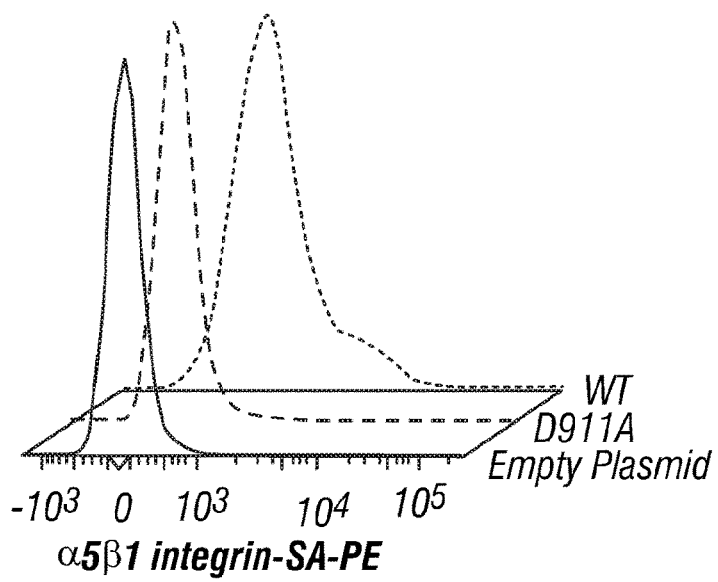

An ELISA demonstrated Invasin activity in terms of the ability to bind soluble $\alpha5\beta1$ integrin. The monomeric, wild-type D4D5 construct exhibited an ELISA $EC_{50}$ of about 18 nM (Table 1) (Kuolee and Chen, 2008), versus the previously reported affinity of about 70 nM (Tran Van Nhieu and Isberg, 1993). The wild-type, D1D5 construct was detected more sensitively, with an $EC_{50}$ of 3.8±0.4 nM, similar to previously reported values of about 5 nM (Van Nhieu and Isberg, 1991) (Table 1). No detectable binding was observed for the D911A variant (FIG. 1D). The higher observed affinity of D1D5 is likely due to avidity effects from dimer formation near the solid surface, as has been proposed to occur on the bacterial surface (Dersch and Isberg, 1999).

all the required elements to mediate transportation to and immobilization in the outer membrane of gram-negative bacteria was used advantageously. The entire gene was cloned, including the native signal peptide, beta barrel and the D1D5 extracellular domains into plasmid pBAD30 to yield plasmid pTAK020 (FIG. 2A). Expression in *E. coli* cells, followed by labeling with the anti-Invasin antibody 3A2 (Leong et al., 1990), demonstrated a high level of Invasin displayed on *E. coli* cells expressing wild-type or D911A Invasin as compared to cells containing the parent pBAD30 plasmid (FIG. 2B). Similarly, biotinylated soluble $\alpha_5\beta_1$ integrin specifically bound bacterial cells displaying wild-type Invasin but not the inactive D911A variant or control cells (FIG. 2C). Together, these data demonstrate that full-length Invasin can be displayed at a high level and in active conformation on the *E. coli* bacterial outer membrane, enabling high-throughput FACS-based sorting schemes.

Identification of Residues Key for Invasin-Integrin Binding

Figure 3A:
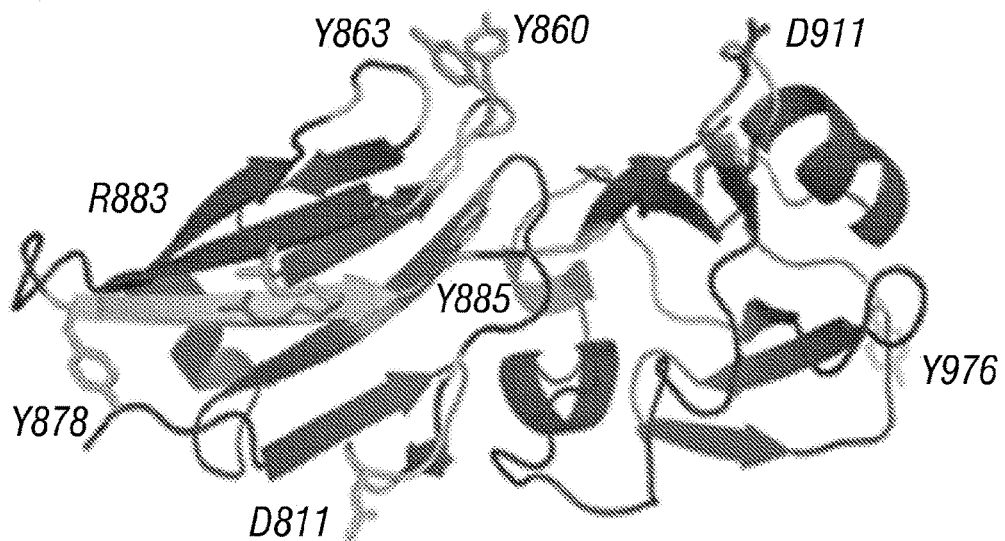
FIGS. 3A-3B—Surface exposed residues involved in integrin binding. 3A, Structure of Invasin D4D5 domain with residues tested for the ability of alanine substitution to affect $\alpha_5\beta_1$ integrin binding as reported in panel B: Y878, D811, Y976, and Y885=negligible or enhanced effect; Y863 and Y860=modest negative effect; D911=pronounced negative effect. The disulfide bond is shown. Figure made from PDB 1CWV with PyMol. 3B, E. coli displaying individual Invasin variants were each stained separately with fluorescent $\alpha_5\beta_1$ integrin and with anti-Invasin monoclonal antibody 3A2 to assess the ability of each variant to bind integrin and assess the relative Invasin surface density. The median fluorescence intensities were each normalized to the corresponding signals for wild-type Invasin, with the ratio of the normalized integrin binding to normalized antibody binding used as a metric of specific activity (non-normalized. *Variant Y976A showed no binding to the 3A2 antibody, thus only the normalized integrin binding activity is reported.

To help guide library design for identification of affinity-enhanced variants, it was first desirable to identify Invasin regions that are likely to influence receptor binding and may be amenable to substitution with different residues that increase binding affinity. Reasoning that solvent-exposed tyrosine residues are highly represented among energetically important protein-protein binding interfaces (Leahy et al., 1996), these were targeted for substitution with alanine. Several of the identified tyrosines fell within the region between residues D911 and the putative synergy site R883, which is a cleft in the integrin-binding domains of fibronectin type III (repeats 9 and 10), but a hydrophobic bulge with five aromatic residues in Invasin (Hamburger et al., 1999; Leahy et al., 1996). Five residues were identified meeting the criteria (Y860, Y863, Y878, Y885, and Y976) and individually altered each to alanine (FIG. 3A). The residues D911 and D811 were previously shown to support integrin binding (Hamburger et al., 1999; Saltman et al., 1996), while R883 was speculated to play a role (Hamburger et al., 1999), and were included.

Figure 9A:
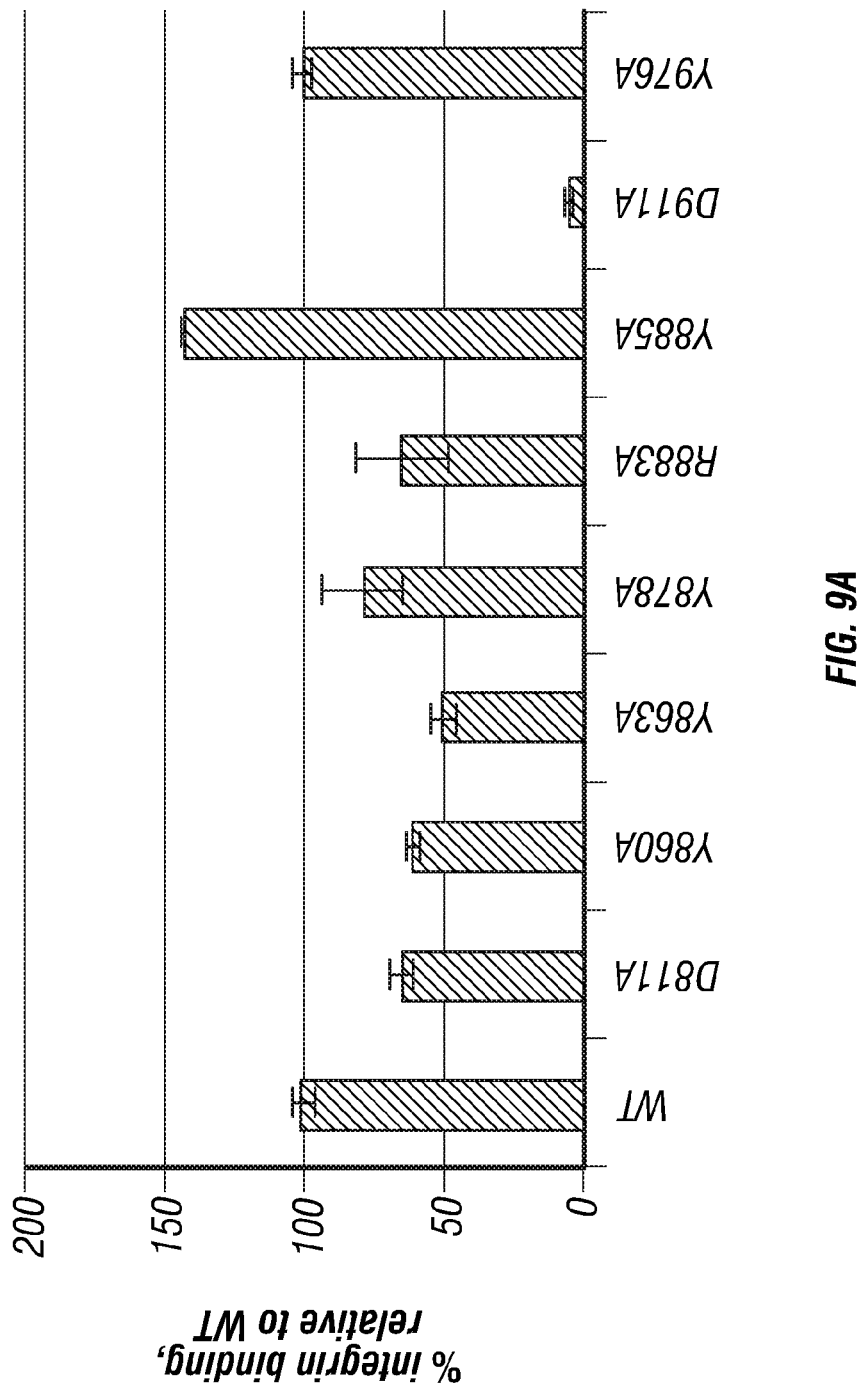
FIGS. 9A-9B—Expression levels and activity of Invasin alanine variants on the E. coli surface. 9A, Integrin binding of Invasin variants. E. coli displaying individual Invasin variants were stained with biotinylated $\alpha_5\beta_1$ integrin followed by streptavidin-PE and analyzed by flow cytometry. 9B, Relative display levels of Invasin variants on E. coli. E. coli displaying individual Invasin variants were stained with the 3A2 antibody, followed by anti-mouse IgG-APC and analyzed by flow cytometry. The mean fluorescence intensity of each sample was normalized as follows: (sample MFI−average background MFI)/(average WT MFI−average background MFI)×100%. Background fluorescence was determined as the fluorescence resulting from stained cells with empty plasmid and from cells expressing WT Invasin that were incubated only with the secondary reagent (SA-PE or anti-mouse IgG-APC). Data shown is average of replicate cultures; the experiment was repeated twice.
Figure 9B:
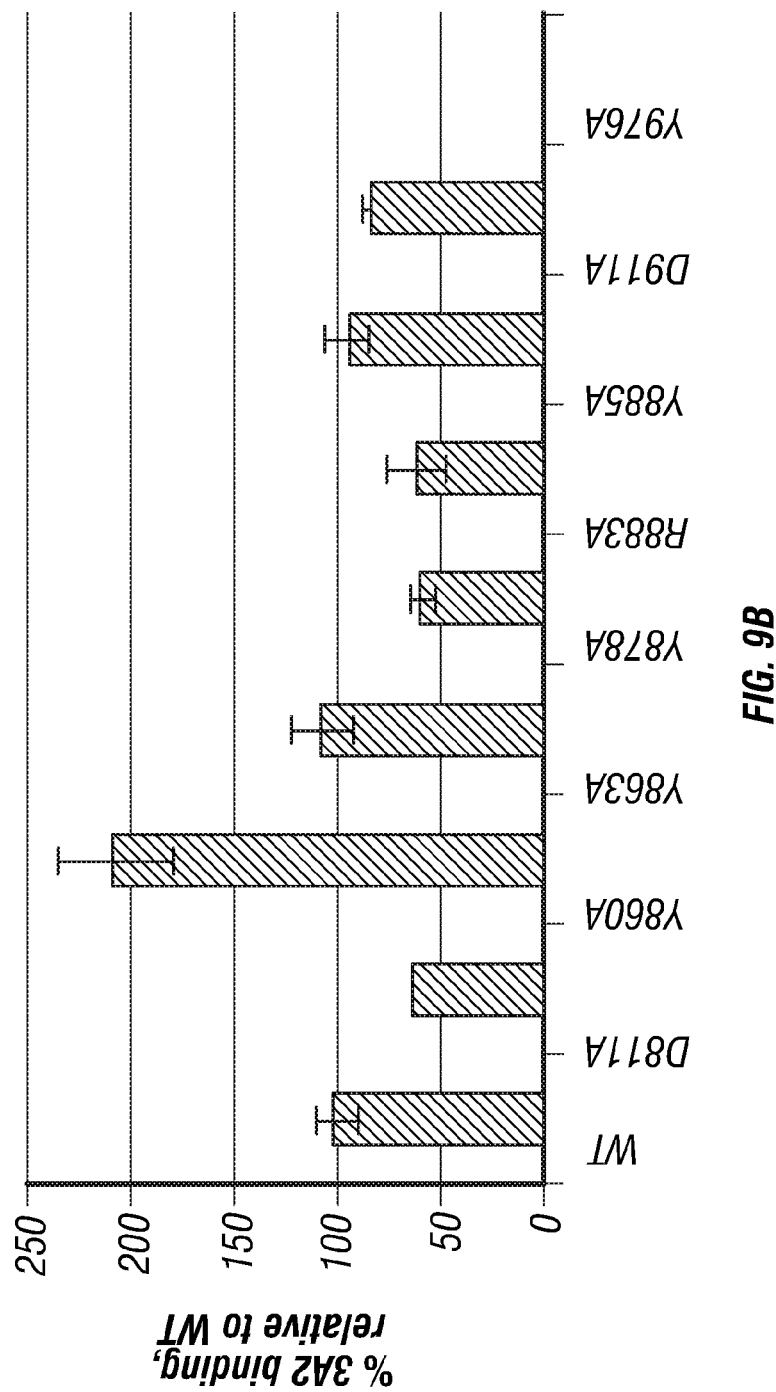
Figure 10:
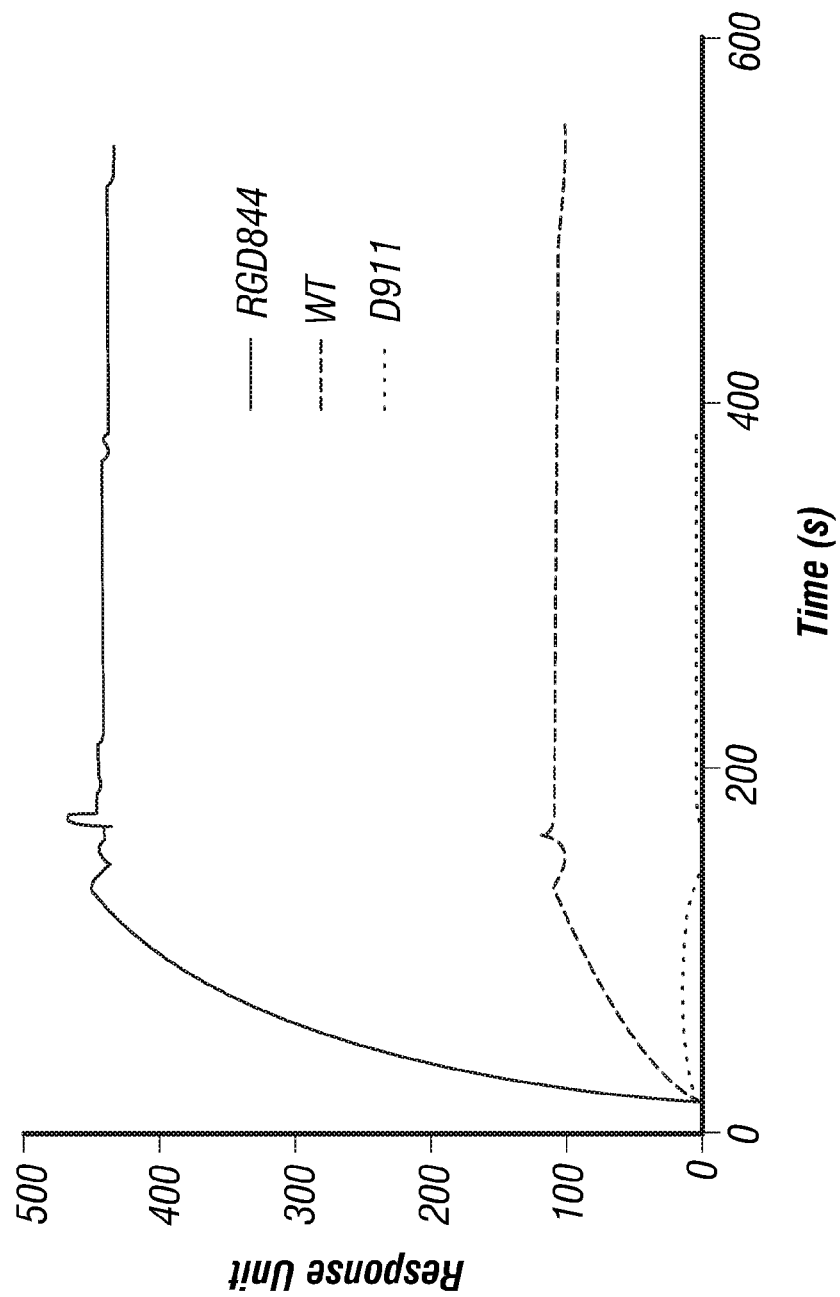
FIG. 10—SPR binding of Invasin variants to soluble a5b1 integrin. Representative surface plasmon resonance analysis for D911A, RGD844 and WT Invasin. Soluble $\alpha_5\beta_1$ integrin was coupled to a CMS chip via EDC/NHS chemistry, with MBP-D1D5 Invasin variants injected at a concentration of 1000 nM over the surface in the presence of 2 mM MnCl$_2$. The experiment was performed on a BIAcore 3000 instrument with a flow rate of 30 µL/min.
Figure 11A:
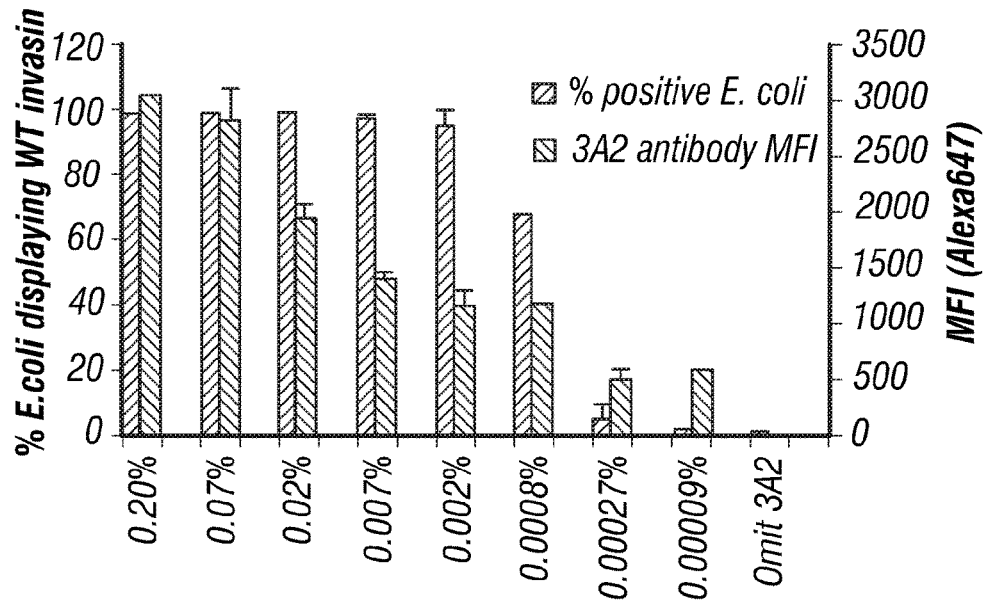
FIGS. 11A-11E—Differential cellular invasion by Invasin variants is not due to expression differences. To carefully control for potential confounding effects due to differences in either the percent of E. coli cells displaying Invasin or the surface density of Invasin, the arabinose concentrations were titrated to adjust induction levels and compared the results for WT and RGD844 Invasin. The resulting percent of E. coli displaying Invasin and the relative surface density of Invasin were measured using the 3A2 antibody and flow cytometry data are shown in 11A and 11B for the WT and RGD844 variants, respectively. Note, these variants have identical affinity for the 3A2 antibody, as shown in FIG. 12. A eukaryotic cell invasion assay was next used to assess the impact of varying percent positive E. coli and Invasin surface densities on cellular invasion. 11C and 11D show this data for the WT and RGD844 variants, respectively, and 11E shows this for uptake of bacteria expressing WT Invasin into Caco-2 cells. Under the assay conditions, with an MOI of 70, the ability of E. coli to invade eukaryotic cells is not sensitive to arabinose concentration above 0.002%.
Figure 11B:
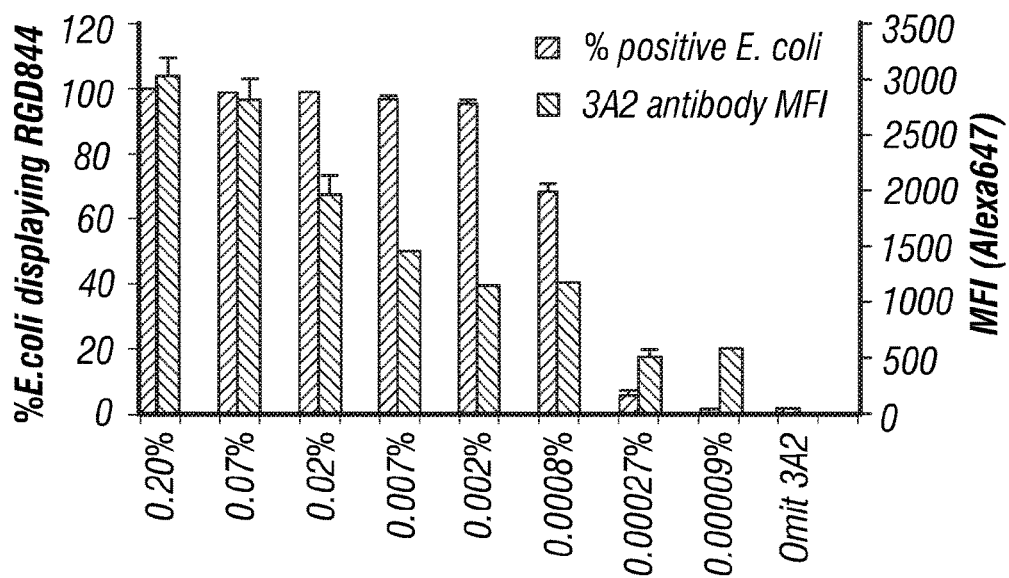
Figure 11C:
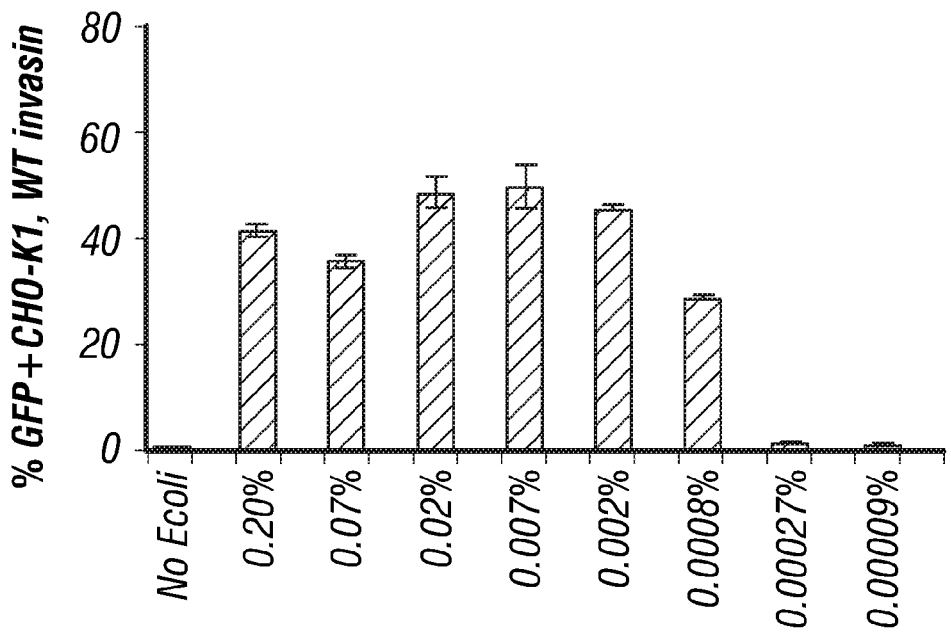
Figure 11D:
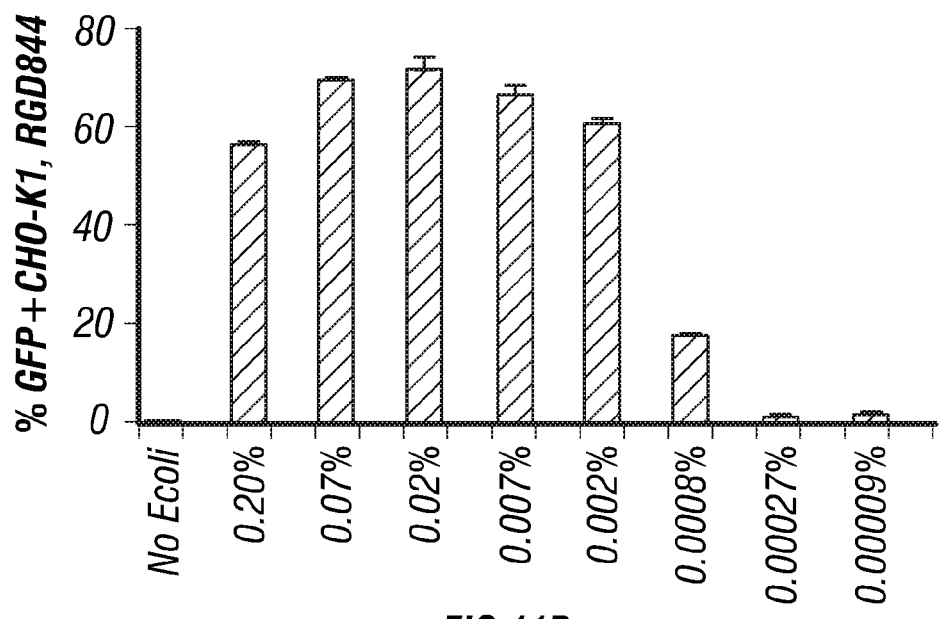
Figure 11E:
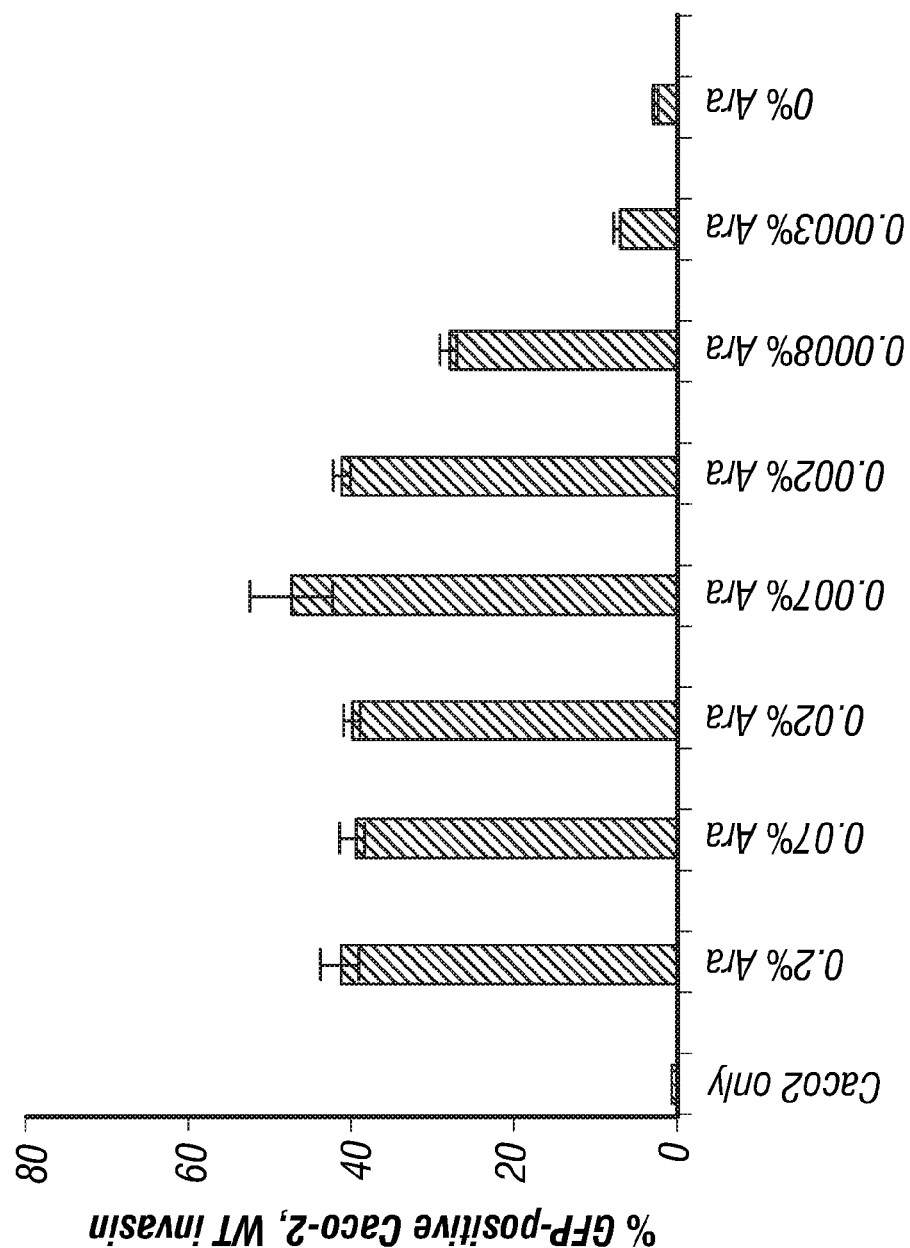

All alanine variants were cloned into pTAK020 for display on the *E. coli* surface. Each variant was individually analyzed by flow cytometry for the ability to bind the 3A2 antibody, as a measure of surface display level, and biotinylated $\alpha_5\beta_1$ integrin, as a measure of activity. The expression levels of all variants, except Y976A, were within two-fold of the wild type level (FIGS. 9A and 9B). To compare the variants, the specific activity was calculated as

TABLE 1

Binding of Invasin variants to select integrins.

| | Affinity for integrin variants, ELISA $EC_{50}$ (nM)** | | | | |
|---|---|---|---|---|---|
| | MBP-D1D5 | | | MBP-D4D5 | |
| Variant | $\alpha_5\beta_1$ | $\alpha_v\beta_1$ | $\alpha_v\beta_3$ | $\alpha_5\beta_1$* | $\alpha_3\beta_1$* |
| WT | 3.77 ± 0.40 | 104.6 ± 0.78 | >>1000 | 18.2 ± 0.74 | 1.72 ± 0.60 |
| D911A | ND | ND | >>1000 | ND | ND |
| RGD | 0.47 ± 0.06 | 1.23 ± 0.11 | about1000 | 3.1 ± 0.54 | 0.79 ± 0.19 |
| F844Y | 2.59 ± 0.3 | 86.13 ± 1.75 | >>1000 | 7.85 ± 1.40 | 2.61 ± 1.02 |
| RGD844 | 0.40 ± 0.05 | 1.53 ± 0.17 | ND | 2.34 ± 0.15 | 0.82 ± 0.14 |
| Fbn | 0.67 ± 0.09 | 4.64 ± 0.30 | 44.55 ± 4.28 | N/A | ND |

**All ELISAs were performed in the presence of 2 mM Mn2+. All assays were performed with MBP-D1D5 except those noted by * were performed with MBP-D4D5.

Figure 3B:
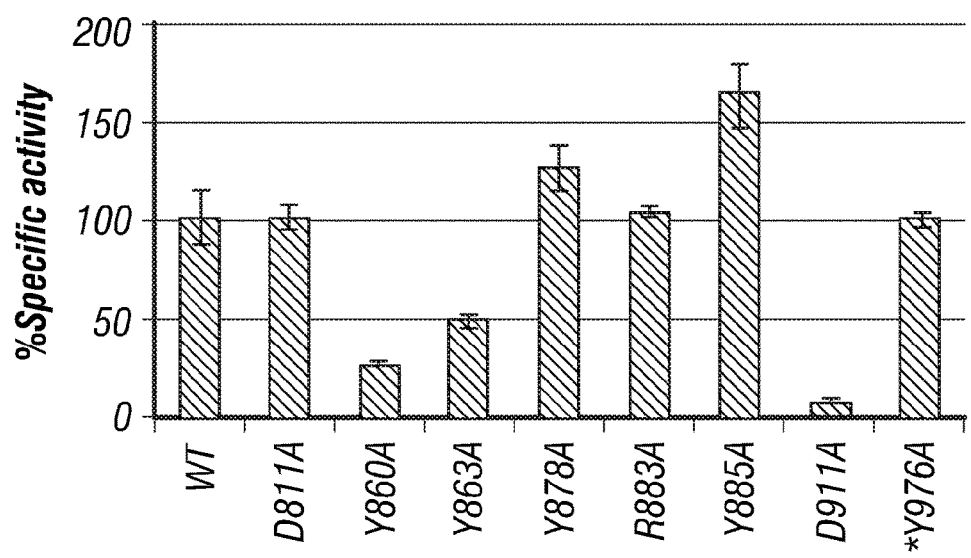

In order to perform directed evolution to select higher affinity variants, the fact that the intact Invasin gene contains the ratio of wild-type normalized integrin binding activity to wild-type normalized expression level. Wild-type Invasin exhibited high levels of integrin binding activity, while the D911A control again showed minimal activity, similar to control bacteria lacking Invasin. Of the remaining variants, Y860A and Y863A exhibited reduced $\alpha_5\beta_1$ integrin binding activities, while variants Y878A, and Y885A exhibited modest increases in binding (FIG. 3B; non-normalized data in FIGS. 9A and 9B). Roles for residues Y860 and Y863 in integrin binding can be explained by inspection of the structure, as they are in close proximity to and on the same face of the protein as D911 (FIG. 3A). Since the Y976A variant was not detected by the 3A2 antibody but showed wild-type levels of integrin binding activity, it is conclude that this residue is critical for 3A2 antibody recognition and report the normalized integrin binding activity (FIGS. 9A and 9B). Residue Y976A is distant from the other tested residues (FIG. 3A), and thus it is unlikely that any other tested residues directly impact 3A2 binding.

Invasin Library Design and Selection

Based on this information, four site-saturation mutagenesis libraries were generated to fine-tune the interactions of key Invasin residues with integrin. Library 1 randomized ten residues 858-865 that form a loop including Y860 and Y863, and residues F844 and N847 that are located on an adjacent loop with side chains oriented towards the 860-863 loop. Similarly, library 2 randomized the surface exposed residues on the beta sheet between positions 878-883, including Y878 and R883. Library 3 surrounded the residue D811, targeting the surface loop between residues 809-814. Library 4 surrounded the essential residue D911, randomizing the 908-913 loop. Each library contained >10$^7$ unique transformants, ten-fold greater than the theoretical library size.

Libraries were displayed on the surface of E. coli and subjected to sequential cellular invasion and FACS-based $\alpha_5\beta_1$ integrin binding enrichment steps. The initial selection, based on the ability to bind and/or be internalized by Caco-2 cells, was designed to mimic the in vivo delivery process. Caco-2 cells are derived from a human colon carcinoma and possess key features of intestinal M cells. As a result, they have become a popular M cell model and are commonly used in permeability and uptake assays. The Caco-2 screening step is expected to select for clones expressing full-length, correctly folded Invasin variants but minimally discriminate between variants with different integrin binding affinities due to avidity effects. The subsequent screening steps using soluble, fluorescent $\alpha_5\beta_1$ integrin as a basis for FACS sorting are expected to recover variants with higher integrin binding affinity. Each library was subjected to two rounds of Caco-2 selection followed by up to four rounds of FACS with decreasing integrin concentrations. At this point, the populations were enriched, as indicated by stable population MFI and sequence convergence (Table 3).

TABLE 3

Sequences of Invasin variants selected from libraries.

| Clone Name** | Amino acid changes |
| --- | --- |
| 1R5-2 | F844A, N847H, I858V, Y863F, S864Y |
| 1R6-1 | F844Y |
| 2R5-2 | S879A, S881V |
| 2R5-3 | Y885S |
| 2R5-4 | S881V, R883K, Y885S |
| 2R6-7 | S881V |
| 3R5-2 | A809P, T810P, D811S, K812G, F814L |
| 3R5-4 | A809T, T810P, K812H, F814L |
| 4R3-3 | G909R, S910G, M912L, S913A |
| RGD | G909R, S910G |
| DLA | M912L, S913A |
| RGD844 | F844Y, G909R, S910G |

**Nomenclature is such that the first number indicates the library of origin, Rx indicates the selection round from which the clone was recovered, while the final number indicates the clone #.

For library 1, all positions were dominated by the wild-type residues, except for position F844, which was replaced by tyrosine in 7 of 10 sequenced clones. Similarly, for library 2 only one position was dominated by a non-wild-type amino acid, S881V, observed in 8 of 10 clones. Library 3 did not exhibit sequence convergence, suggesting the region is permissive to amino acid substitution. Library 4, surrounding the critical D911 residue, exhibited rapid sequence convergence. All clones sequenced after two Caco-2 cell enrichment steps included the wild-type D911 residue, while three of those sequenced after the first FACS sort further modified the local D911 environment to include a RGD motif, a motif known to mediate binding to certain integrins (Ruoslahti, 1996). Further rounds of enrichment and sequence analysis isolated clones containing the RGD motif in addition to M912L and/or S913A substitutions, collectively termed RGDLA.

Generation of High Affinity Invasin Variants Containing RGD-Motif

Figure 4A:
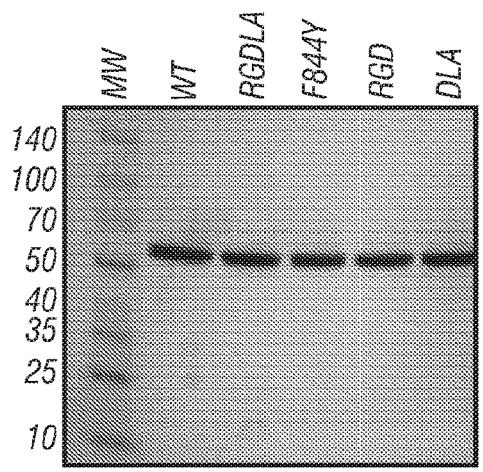
FIGS. 4A-4C—Selected Invasin variants have increased $\alpha_5\beta_1$ integrin binding affinity. 4A, SDS-PAGE of purified MBP-D4D5 Invasin variants, with molecular weight markers shown. 4B, ELISA of the RGDLA clone selected from library 4, and derivative with only the RGD or DLA amino acid changes versus WT. An ELISA plate was coated recombinant $\alpha_5\beta_1$ integrin, blocked and Invasin variants titrated in the presence of 2 mM MnCl$_2$, followed by detection with anti-MBP antibody-HRP conjugate. 4C, ELISA comparison of WT Invasin with variants containing F884Y, RGD, and a variant combining the RGD and F844Y changes (RGD844).
Figure 4B:
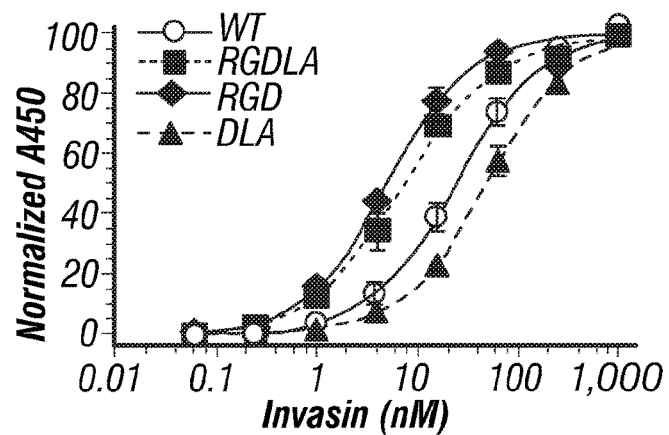
Figure 4C:
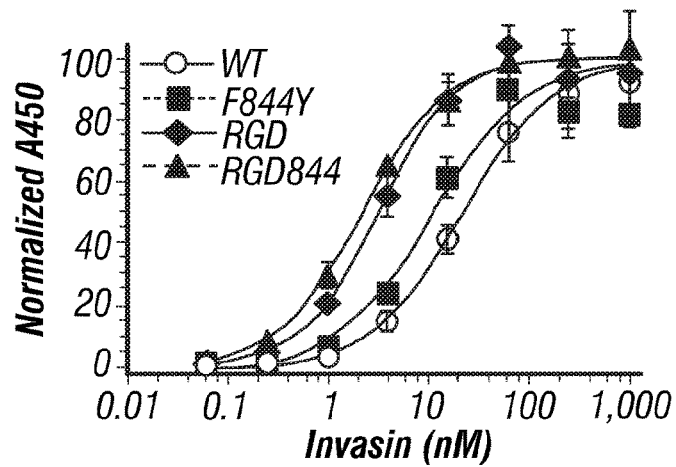

These dominant clones were expressed as monomeric MBP-D4D5 proteins (FIG. 4A) to more readily discriminate between affinity differences in ELISA with immobilized $\alpha_5\beta_1$ integrin. Invasin variants containing the RGDLA substitutions showed increased binding over wild type Invasin (FIG. 4B). In order to understand the contributions of the selected substitutions to binding, the co-selected G909R/S910G and M912L/S913A substitutions were uncoupled. Two separate variants were generated: RGD, containing G909R/S910G, and DLA, containing the M912L/S913A substitutions. An ELISA with purified Invasin in the MBP-D4D5 format showed similar binding for DLA and wild-type Invasin, while RGD exhibited similar binding as the RGDLA variant and about a six-fold lower EC$_{50}$ as compared to wild-type Invasin (FIG. 4B; Table 1). Substitution F884Y, enriched in Library 1, exhibited slightly improvement binding as compared to wild-type (FIG. 4C). The S881V clone exhibited lower binding than wild type and was not further pursued.

Since the selected RGD and F844Y substitutions are distant from each other in the structure, it was theorized that they may independently contribute to enhanced binding and could be combined to generate a variant with further enhanced affinity. Therefore the F844Y change was introduced into the RGD variant to create variant RGD844. This conferred a small additional affinity enhancement beyond that of the RGD variant, as observed in ELISA (FIG. 4C) that was also observed with BIAcore (FIG. 4D). Due to difficulties in regenerating the $\alpha_5\beta_1$ integrin surface without denaturing the receptor, a previously reported concern (Lord et al., 2996), only representative traces are shown at 1000 nM. Coupling of the MBP-D1D5 proteins led to no detectable binding signal when flowing soluble integrin over the surface. To determine whether improved affinity is due to higher stability, the thermal stability of wild-type, D911A, was compared to RGD844 Invasin variants with no significant differences observed.

Affinity Improved Invasin Variants do not Mediate Enhanced Bacterial Invasion of Caco2 Cells Next, it was investigated whether improved affinity would also confer enhanced invasive capabilities. The pTAK020 surface display vector containing Invasin variants was co-transformed with pET28_GFP into *E. coli* BL21(DE3). A serial induction scheme, with arabinose to induce Invasin followed by IPTG to induce GFP, resulted in similar GFP intensity and Invasin surface display levels for all variants (FIGS. 9A-9B). Induced *E. coli* cells were incubated with Caco-2 cells for 1.5 hours, after which the Caco-2 cells were washed, trypsinized, and resuspended for FACS analysis (Critchley-Thorne et al., 2006). The resulting Caco-2 cells displayed bimodal distributions, with a GFP-positive population indicating the presence of adherent and/or internalized *E. coli* and a GFP-negative population indicating the absence of bacteria.

Figure 5A:
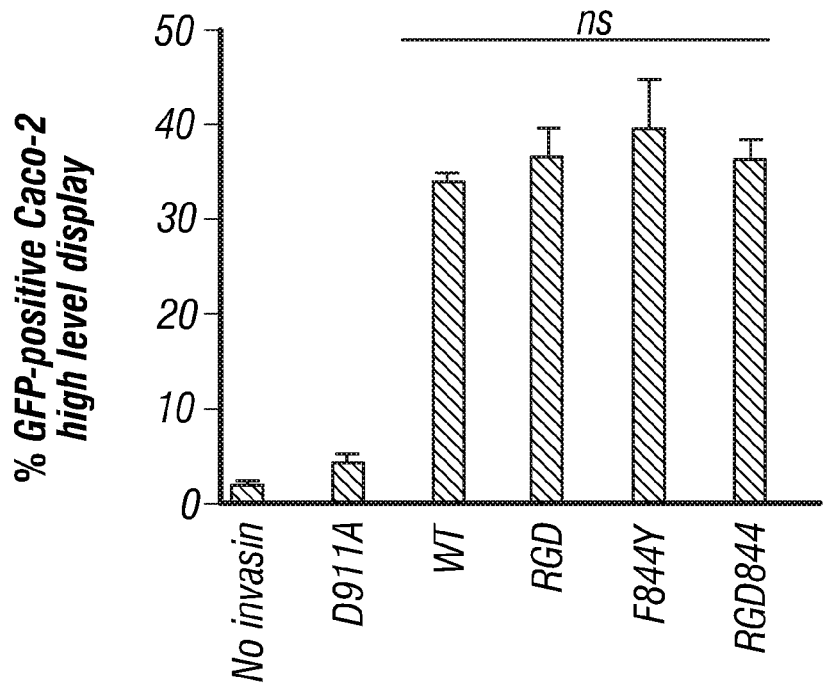
FIGS. 5A-5D—RGD containing Invasin variants do not better adhere to or invade Caco-2 cells. 5A, E. coli cells serially induced to express high levels of Invasin (0.2% arabinose) and GFP (1 mM IPTG) were incubated with Caco-2 monolayers at an MOI of 70 for 1.5 hours, followed by flow cytometry to assess the percent of GFP-positive Caco-2 cells due to the presence of adherent and internalized bacteria. 5B, E. coli cells serially induced to express low levels of Invasin (0.0008% arabinose) and GFP (1 mM IPTG) were incubated with Caco-2 cells and analyzed as above. Ns, not significant. 5C, Confocal microscopy to visualize Invasin-expressing bacteria in association with Caco-2 cells. Bacteria were induced for low or high Invasin expression, incubated with Caco-2 cells as above and imaged immediately to visualize adherent cells. CellMask Deep Red was used to visualize the Caco-2 membrane; GFP (shown as white) indicates the location of bacteria. 5D, Confocal microscopy as above, but Caco-2 cells were treated with gentamycin overnight to kill extracellular bacteria. Imaging the next day visualized only intracellular bacteria. All experiments were repeated at least twice with replicate bacterial cultures used in each experiment.
Figure 12:
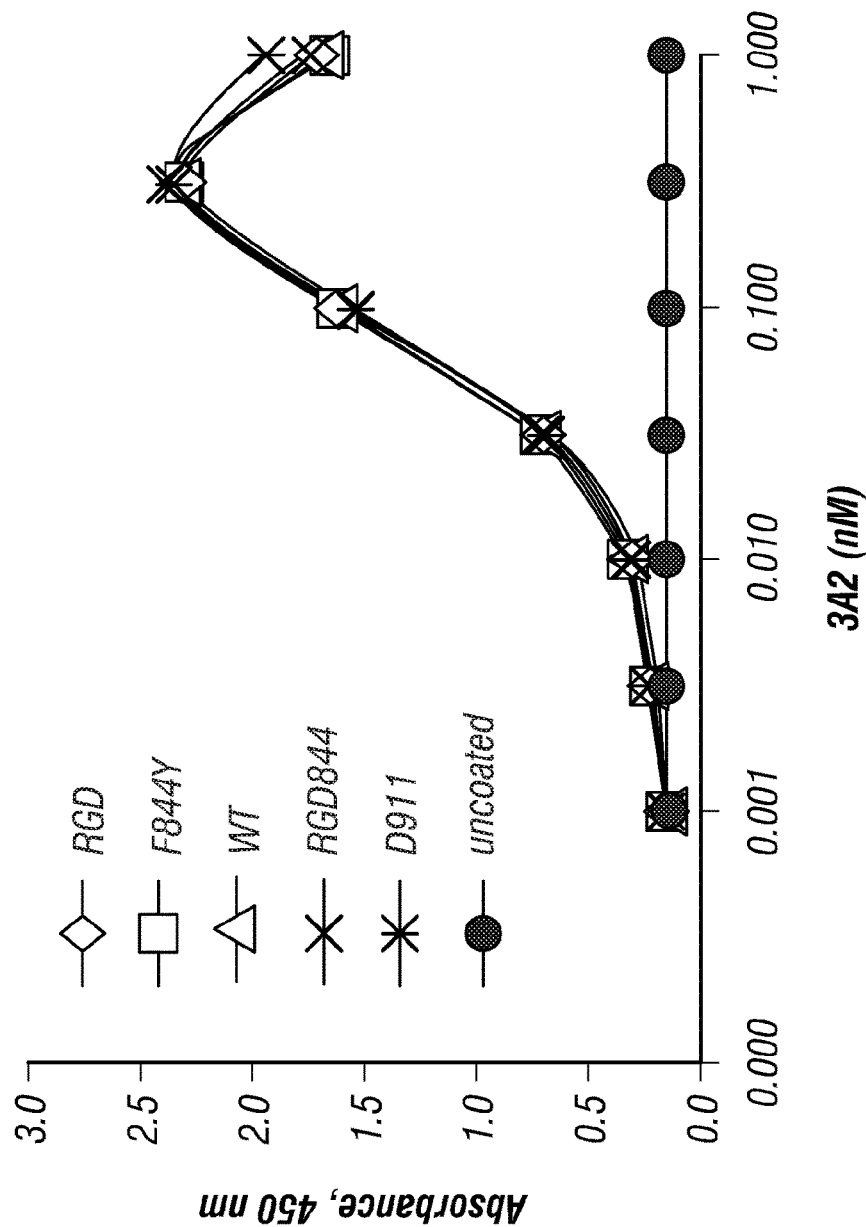
FIG. 12—Selected Invasin variants have identical affinity for 3A2 anti-Invasin antibody. Direct ELISA assay in which purified Invasin variants were coated on the plate at equal concentrations, from preparations of equal purity. After blocking, the 3A2 antibody was titrated and detected with anti-mouse-IgG-HRP.

When Invasin expression was induced with 0.2% arabinose, neither the RGD, F844Y nor the RGD844 variants mediated significantly higher GFP-fluorescence after incubation with Caco-2 cells (FIG. 5A). It was hypothesized that high levels of Invasin display might obscure affinity differences through avidity effects, as previously noted (Dersch and Isberg, 2000). Arabinose titration experiments showed that concentrations of 0.0008% to 0.002% resulted in titratable Invasin expression levels that correlated with bacterial invasion. Induction with a sub-saturating arabinose concentration (0.0008%), followed by GFP induction resulted in consistently low levels of Invasin display and percent GFP-positive cell populations among all variants (FIGS. 11A-11E). The 3A2 antibody bound all variants with similar affinity (FIG. 12), thus the variant expression levels were similar.

Figure 5B:
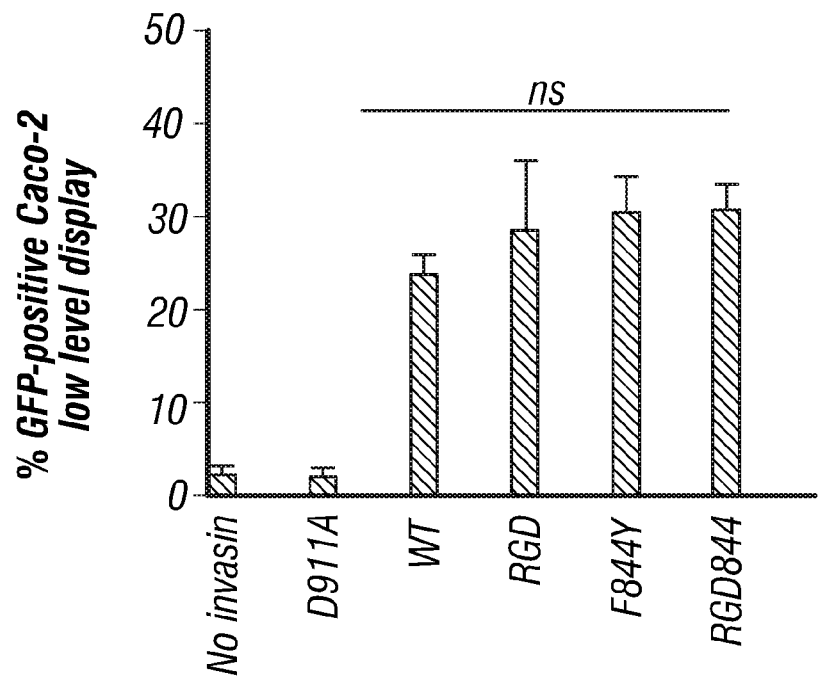
Figure 5C:
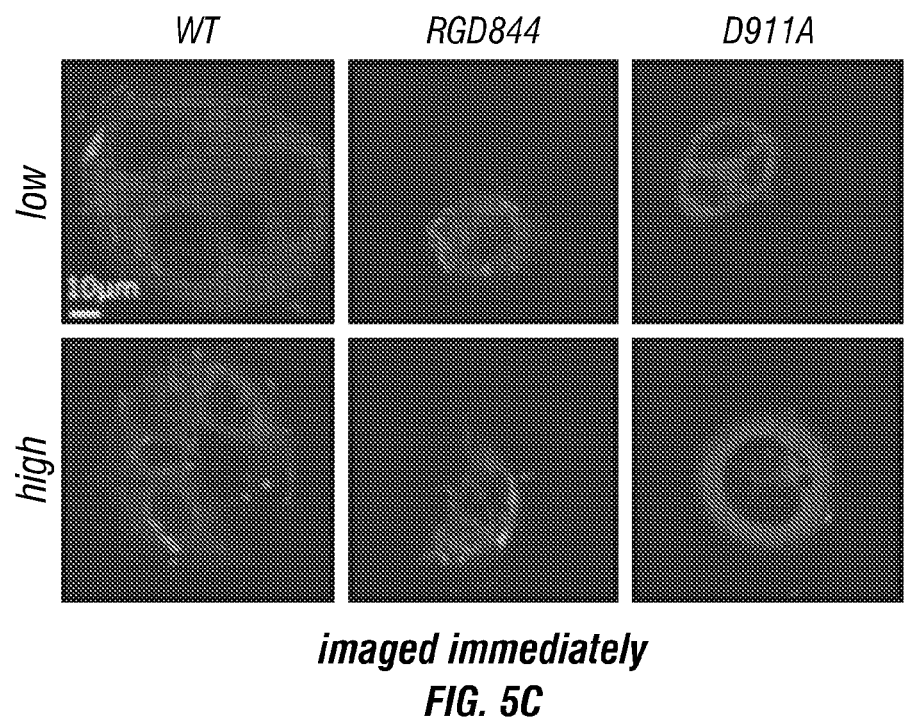
Figure 5D:
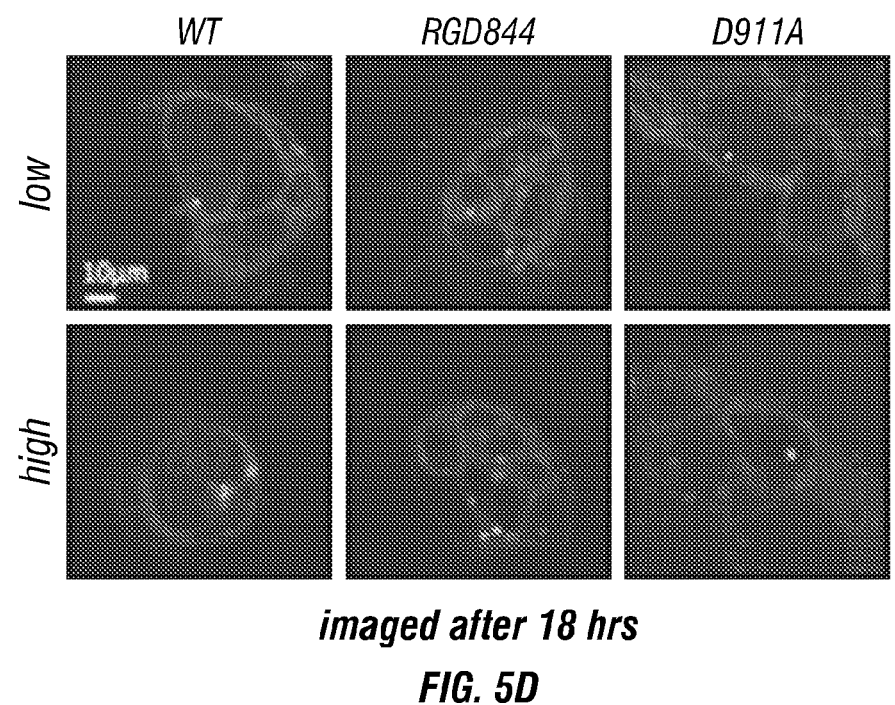
Figure 6A:
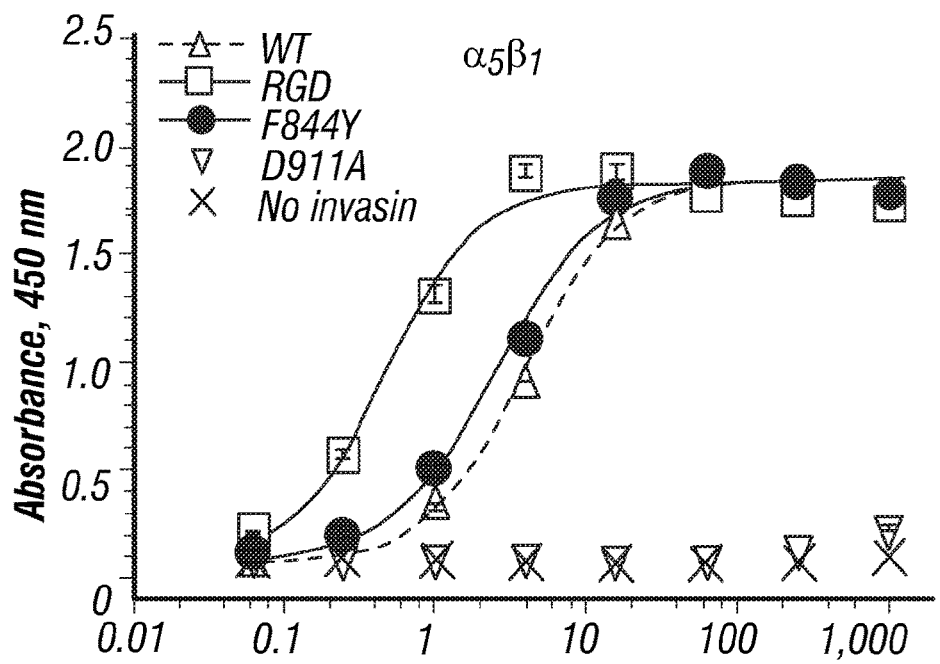
FIGS. 6A-6C—RGD containing Invasin variants have altered integrin binding affinity and specificity. Purified MBP-D1D5 variants were titrated on ELISA plates coated with 6A, soluble $\alpha_5\beta_1$ integrin, 6B, soluble $a_\nu b_1$ and 6C, soluble $a_\nu b_3$ integrin. Invasin variants were detected with anti-MBP-HRP conjugate; controls to assess integrin non-specific binding included the D911A Invasin variant and a no Invasin control.
Figure 6B:
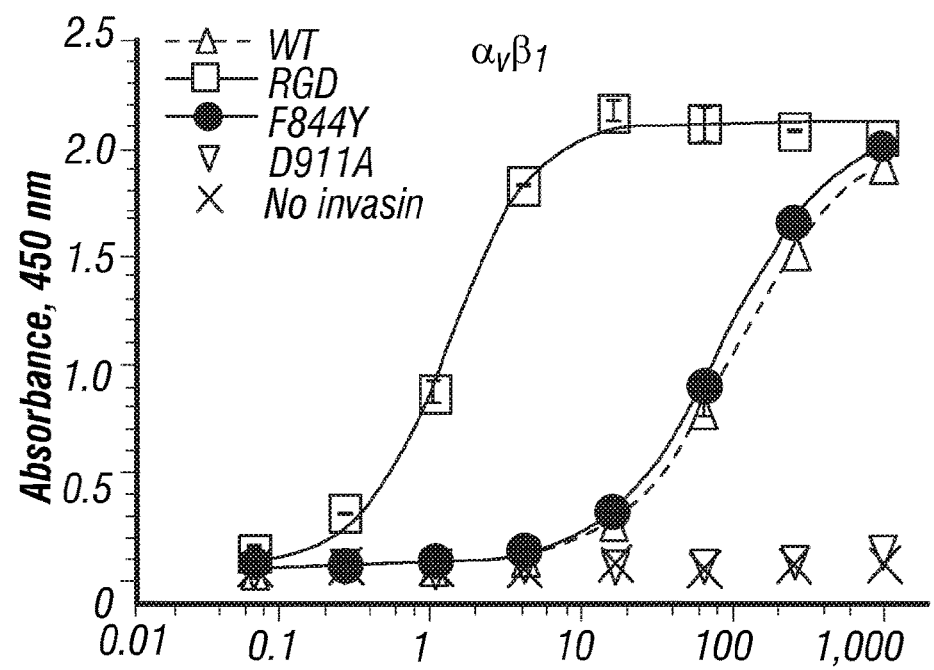
Figure 6C:
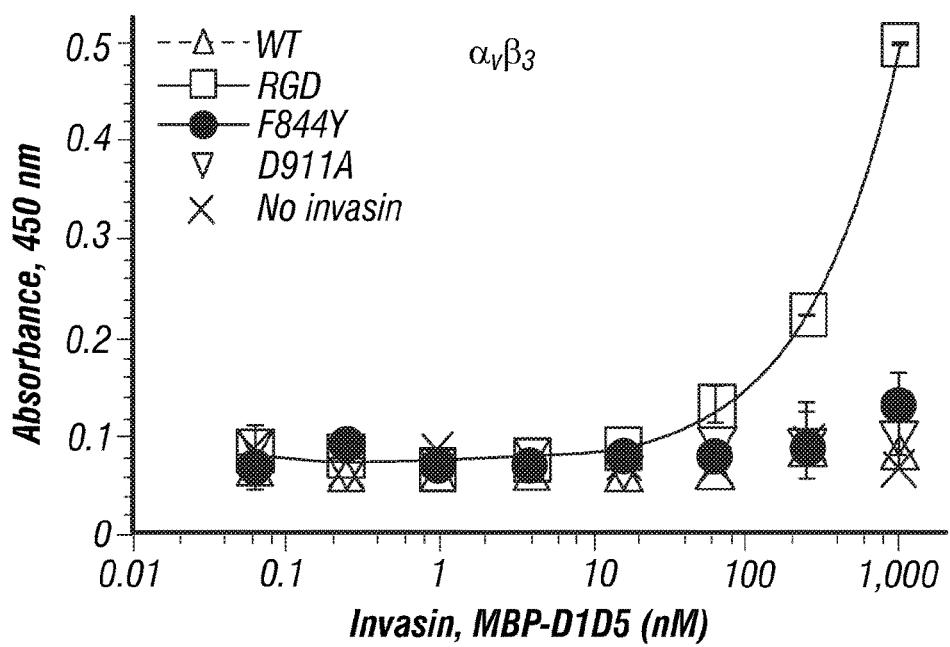

Under these carefully controlled conditions, the ability of Invasin-decorated bacteria to adhere to and invade Caco-2 monolayers was again assessed. The RGD, F844Y and RGD844 variants each only showed a marginally higher adhesion %, which was not statistically significant (FIG. 5B). This supports the idea that Caco-2 invasion during selection served to primarily remove variants with stop codons and other detrimental mutations, while selection with soluble integrin recovered variants with enhanced affinity. Confocal microscopy supports the FACS data. After incubation with Caco-2 cells for 1.5 hours or overnight with gentamycin, *E. coli* displaying wild-type or RGD844 Invasin were observed both adherent and internalized into Caco-2 cells (FIGS. 5C and 5D). In contrast, *E. coli* cells displaying the D911A Invasin variant were very rarely detected in association with Caco-2 cells (FIGS. 5C and 5D). Due to the ease of quantification, flow cytometry statistics were used to compare the variants.

Invasin RGD Variants have Altered Integrin Specificity

The RGD motif was found to significantly increase Invasin $\alpha_5\beta_1$ integrin binding affinity yet did not confer increased Caco-2 invasion. Inspection of Invasin sequences from various *Yersinia* strains and the related *E. coli* adhesion, intimin, revealed that none of these proteins have evolved an RGD motif in their integrin binding site (Table 2). Considering this, it was noted that RGD-containing proteins such as fibronectin are promiscuous, binding a wide variety of integrins, including several which are not bound by Invasin (Ruoslahti and Pierschbacher, 1986). It was therefore hypothesized that inclusion of an RGD motif, while increasing the binding affinity of Invasin for the $\alpha_5\beta_1$ integrin, may also increase affinity for other integrins, altering cell specificity in ways which does not promote *Yersinia* fitness in the context of a bacterial infection.

TABLE 2

Alignment of Invasin and fibronectin sequences surrounding the key aspartic acid.

| Invasin residue | 908 | 909 | 910 | 911 | 912 | 913 |
|---|---|---|---|---|---|---|
| *Y. pseudotuberculosis* | Q | G | S | D | M | S |
| *Y. enterocolitica* | Q | R | T | D | F | T |
| *Y. pestis* | Q | G | S | D | M | S |
| RGD844 | Q | R | G | D | M | S |
| Fibronectin III, repeat 10 | G | R | G | D | S | P |
| high affinity $\alpha_v\beta_3$ antagonist | G | R | G | D | W | N |
| Fibronectin residue | 1492 | 1493 | 1494 | 1495 | 1496 | 1497 |

To test this hypothesis, binding of D1D5 Invasin variants to several other integrin receptors was assessed by ELISA. While the inclusion of an RGD motif increases Invasin binding to the $\alpha_5\beta_1$ integrin about 10-fold, as measured by ELISA $EC_{50}$ (FIG. 6A), this motif also increased affinity for other integrins (Table 1). Notably, Invasin variants including the RGD motif showed about a 70-fold increase in binding to $\alpha_v\beta_1$ (from $EC_{50}$ about 100 nM to about 1.5 nM for RGD, FIG. 6B). Binding to $\alpha_v\beta_3$, an integrin reported to bind and mediate uptake of RGD-containing proteins but not Invasin (Isberg and Leong, 1990; Dupuy and Caron, 2008), was then tested. Only the Invasin RGD variant exhibited detectable binding to $\alpha_v\beta_3$. Although the affinity is still weak ($EC_{50}$ about 1 μM, FIG. 6C), this suggests that RGD-containing Invasin variants are more promiscuous than wild-type.

TABLE 4

Invasin domain locations and functions.

| Domain | Residues | Function | Reference |
|---|---|---|---|
| Signal peptide | 1-48 | Translocation across inner membrane | (Fairman, 2012) |
| Beta barrel | 128-486 | Outermembrane anchor | (Fairman, 2012) |
| D1 | 503-594 | | (Hamburger, 1999) |
| D2 | 595-693 | (Putative) dimerization domain | (Dersch, 1999), (Dersch, 2000) |
| D3 | 694-794 | | (Hamburger, 1999) |
| D4/D5 | 795-986 | Integrin binding superdomain, necessary & sufficient for binding | (Leong, 1991), (Hamburger, 1999) |
| D5 | 887-986 | C-type lectin-like fold | PDB 1CWV |

Next, the cellular adhesion assay was repeated with a different cell line, CHO-K1. Caco-2 cells share some similarities with intestinal epithelial cells and express 12 integrins, including four of the five that bind Invasin (Honore et al., 2000). In contrast, CHO-K1 is a common endothelial cell line expressing a variety of integrins. (Felding-Habermann et al., 1997). Staining of the two cell types with anti-$\alpha_5\beta_1$ antibodies shows that CHO-K1 cells have significantly higher levels of $\alpha_5\beta_1$ integrin than Caco-2 cells. Staining with anti-$\alpha_v\beta_3$ demonstrated that CHO-K1 cells express no detectable $\alpha_5\beta_1$ integrin, while Caco2 cells express low levels of $\alpha_v\beta_3$ integrin (FIGS. 7A and 7B). Under both high and low arabinose induction conditions, *E. coli* displaying Invasin-RGD mediated significantly higher adhesion and/or invasion to CHO-K1 cells than the wild type Invasin as measured by flow cytometry (FIG. 7C) and visualized by confocal microscopy. This result dramatically contrasts with the result obtained with Caco-2 cells. The control experiments allow for the exclusion of the possibility that enhanced CHO-K1 invasion by the RGD844 variant was due to expression level differences (FIGS. 11A-11E). Taken together, induction with 0.002% or 0.0008% arabinose results in *E. coli* populations that are highly similar for the WT and RGD844 variants in terms of the percent of *E. coli* cells expressing Invasin and the relative density of Invasin on the *E. coli* surface. These arabinose concentrations also define the dose-response regime for induction of this protein.

To determine whether the altered integrin specificity conferred by the

Figure 7A:
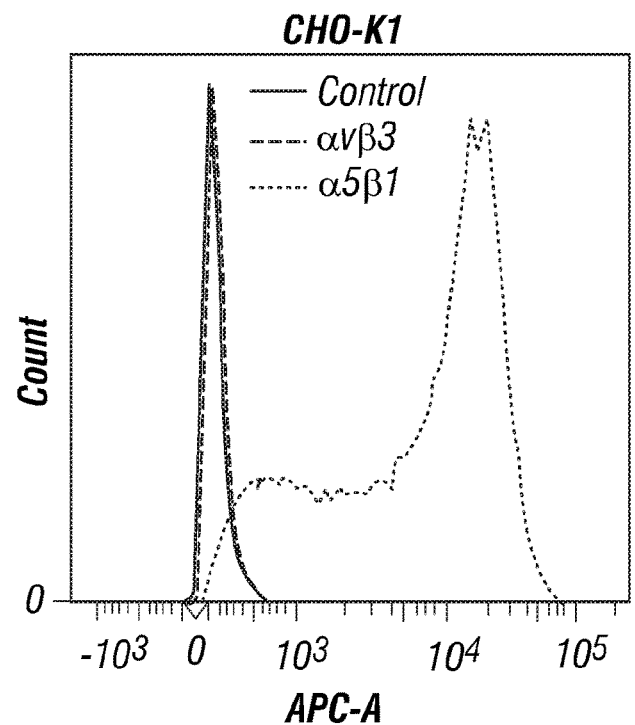
FIGS. 7A-7D—RGD-containing Invasin variants have altered cell selectivity. 7A, CHO-K1 and 7B, Caco-2 cells express different integrin profiles. Flow cytometry was used to assess the levels of $\alpha_5\beta_1$ and $\alpha_\nu\beta_3$ integrins on the cell surface, using integrin specific antibodies, or an isotype control, followed by anti-mouse IgG-allophycocyanin-conjugate. CHO-K1 bacterial invasion assay with Invasin variants. 7C, E. coli were serially induced to express Invasin at low levels, followed by GFP induction and incubation with CHO-K1 cells, washing and flow cytometry analysis to detect GFP-positive CHO-K1 cells. 7D, E. coli were similarly induced but incubated with CHO-K1 cell lines expressing altered integrin profiles. Significance is indicated by * p<0.05,  p<0.01 and * p<0.001; ns, not significant. Control bacteria with empty plasmid indicated by "no Invasin." Each experiment was repeated at least twice and each experiment included replicate bacterial cultures.
Figure 7B:
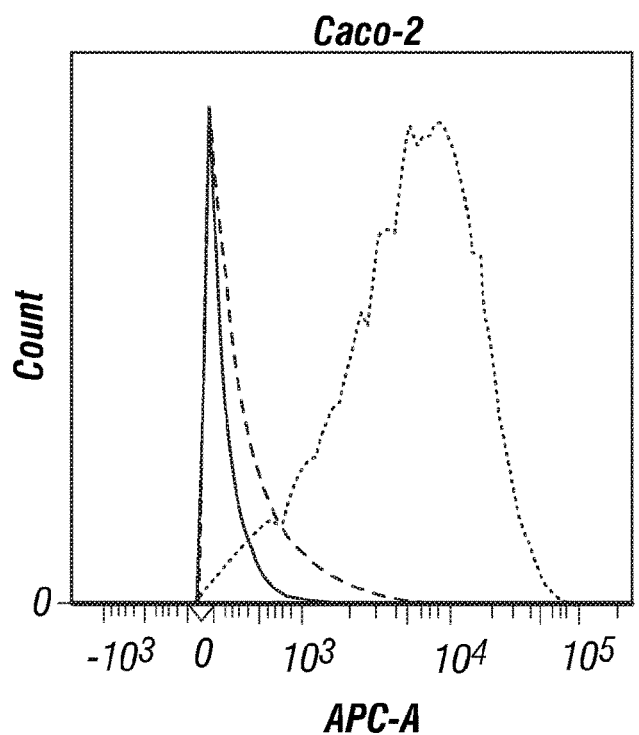
Figure 7C:
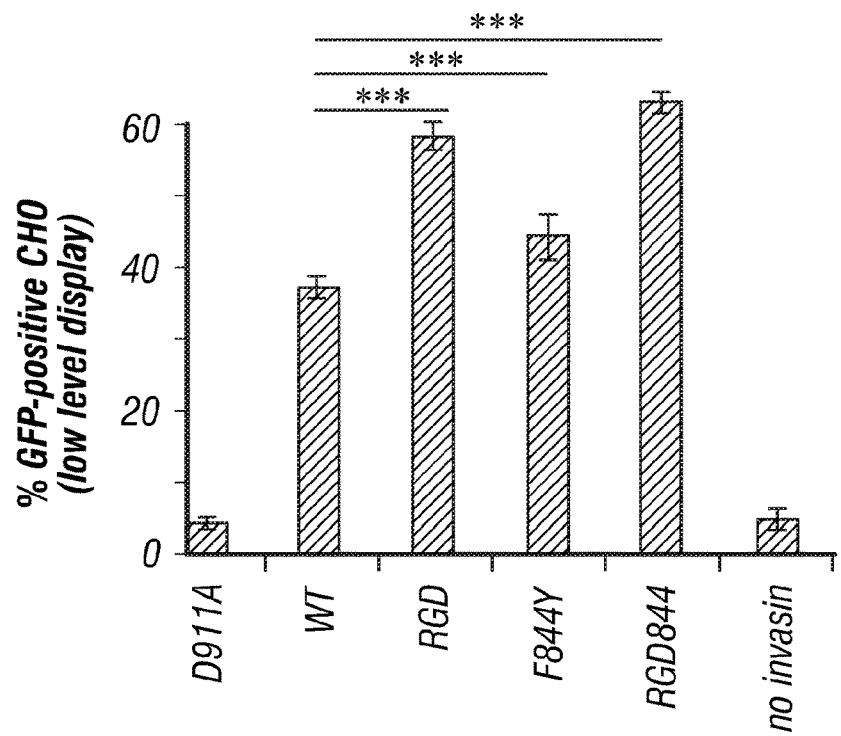
Figure 7D:
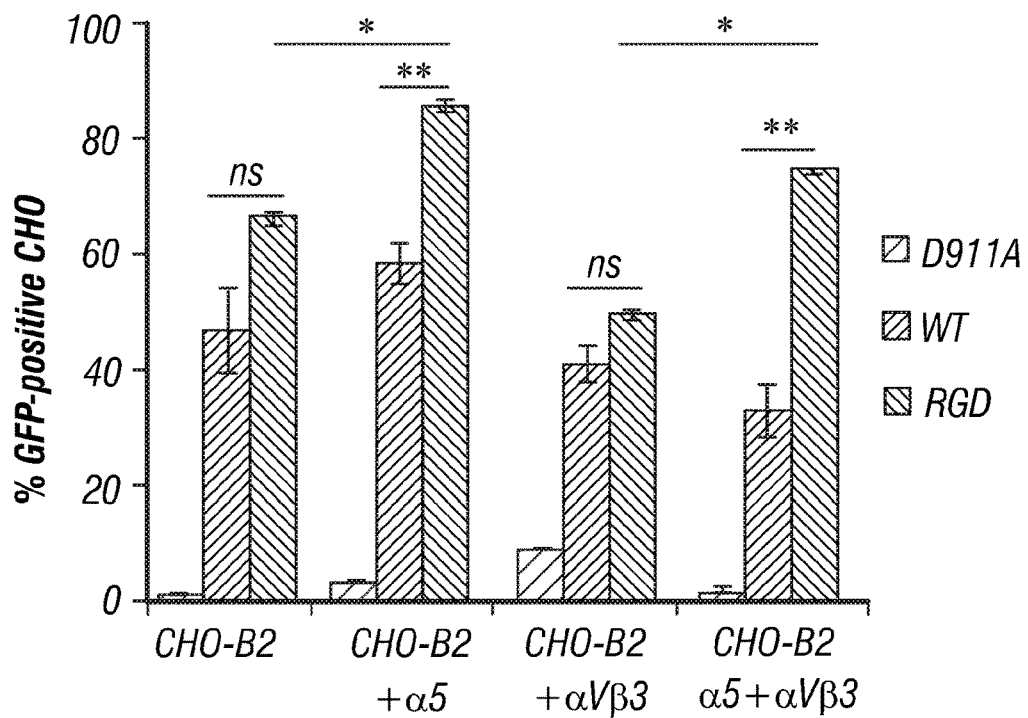
Figure 13A:
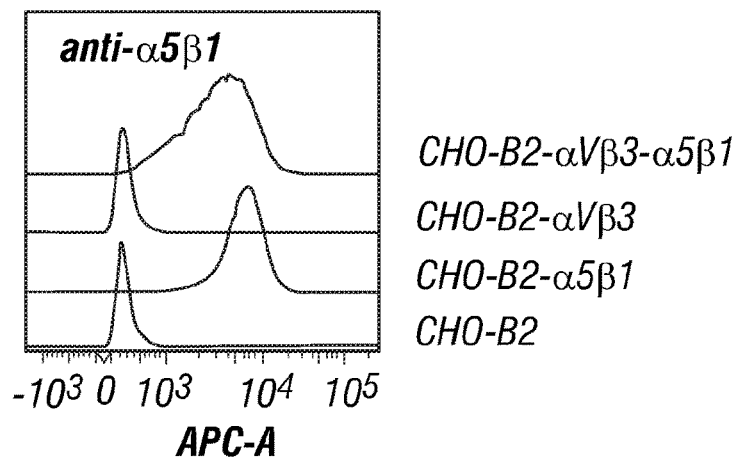
FIGS. 13A-13C—Engineered CHO cell lines express different integrin receptors on their surface. Growing stable CHO cell lines were washed with PBS and detached with Accutase. Next, $2 \times 10^5$ cells were stained with 1 ug each of anti-human $\alpha_5\beta_1$ (13A) (Millipore, MAB1969), anti-human $\alpha_v\beta_3$ (13B) (Millipore, MAB1976), or an isotype control antibody (13C) in 100 uL PBS+1% FBS for 30 min on ice. The cells were washed once before incubation with 1:200 APC anti-mouse Ig (BD). Cells were washed a second time before analysis by flow cytometry (Fortessa).
Figure 13B:
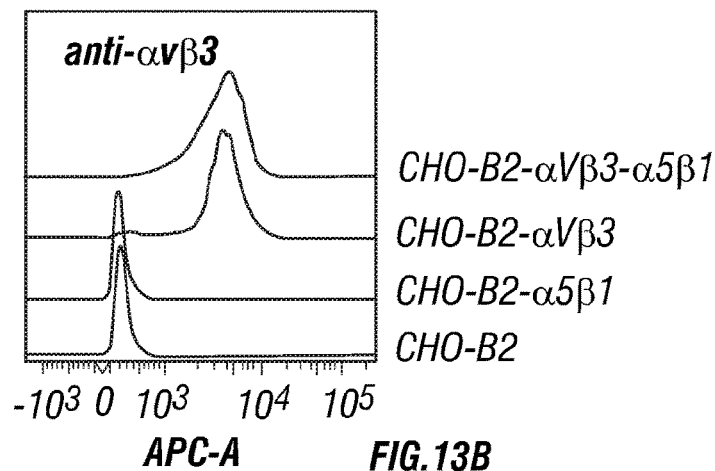
Figure 13C:
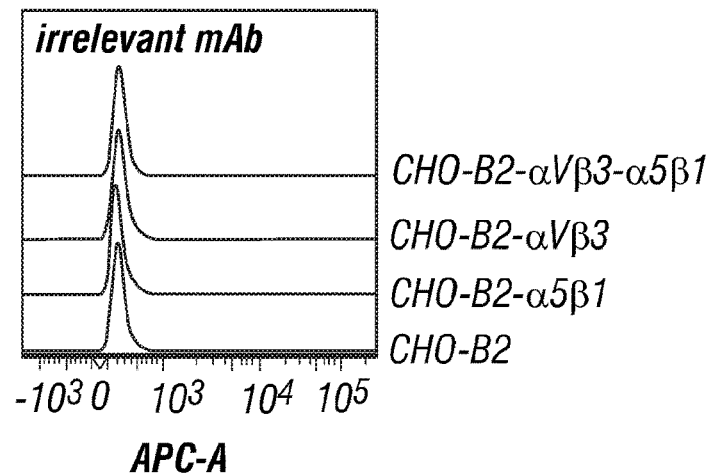
Figure 15A:
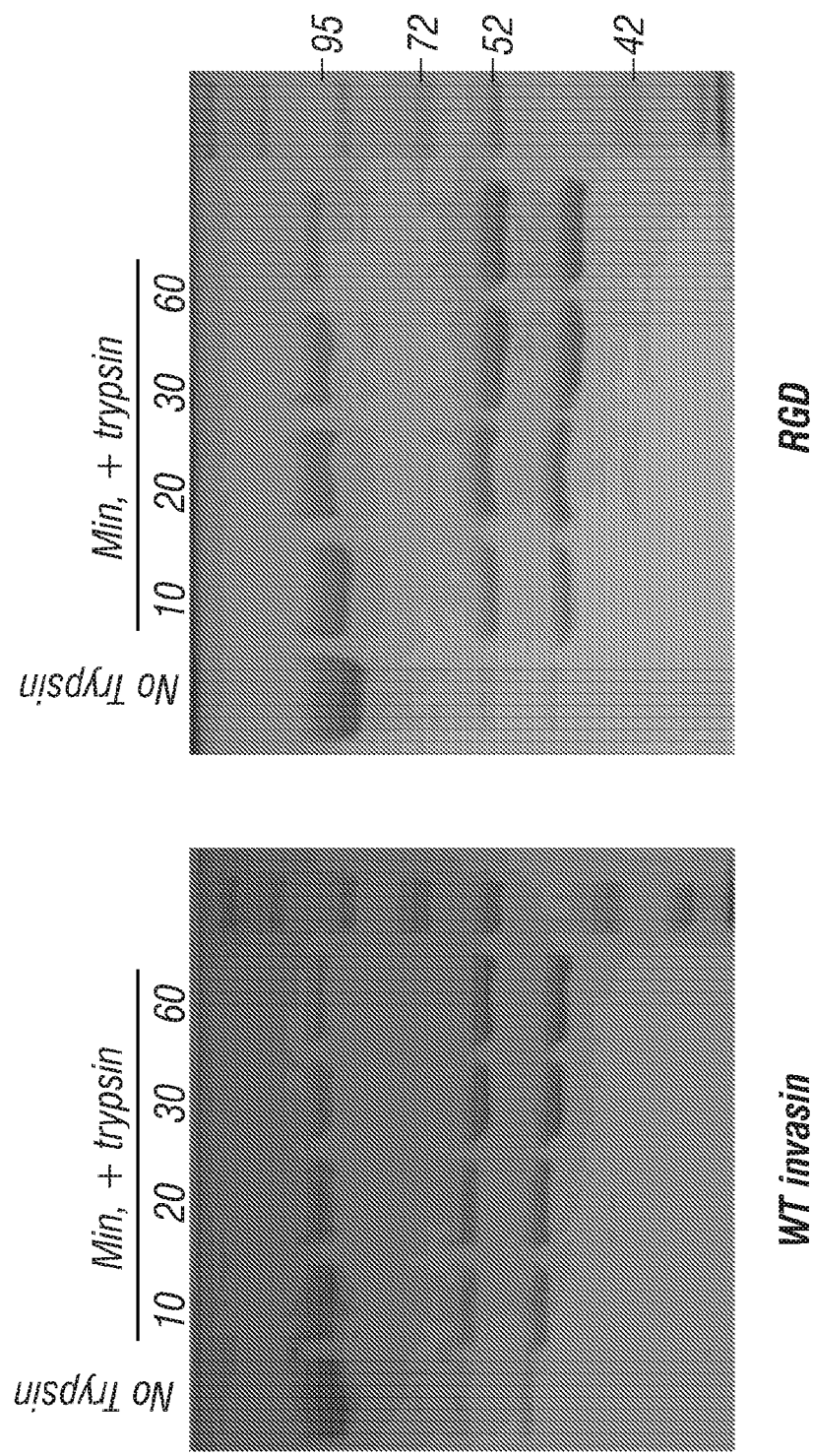
Figure 15B:
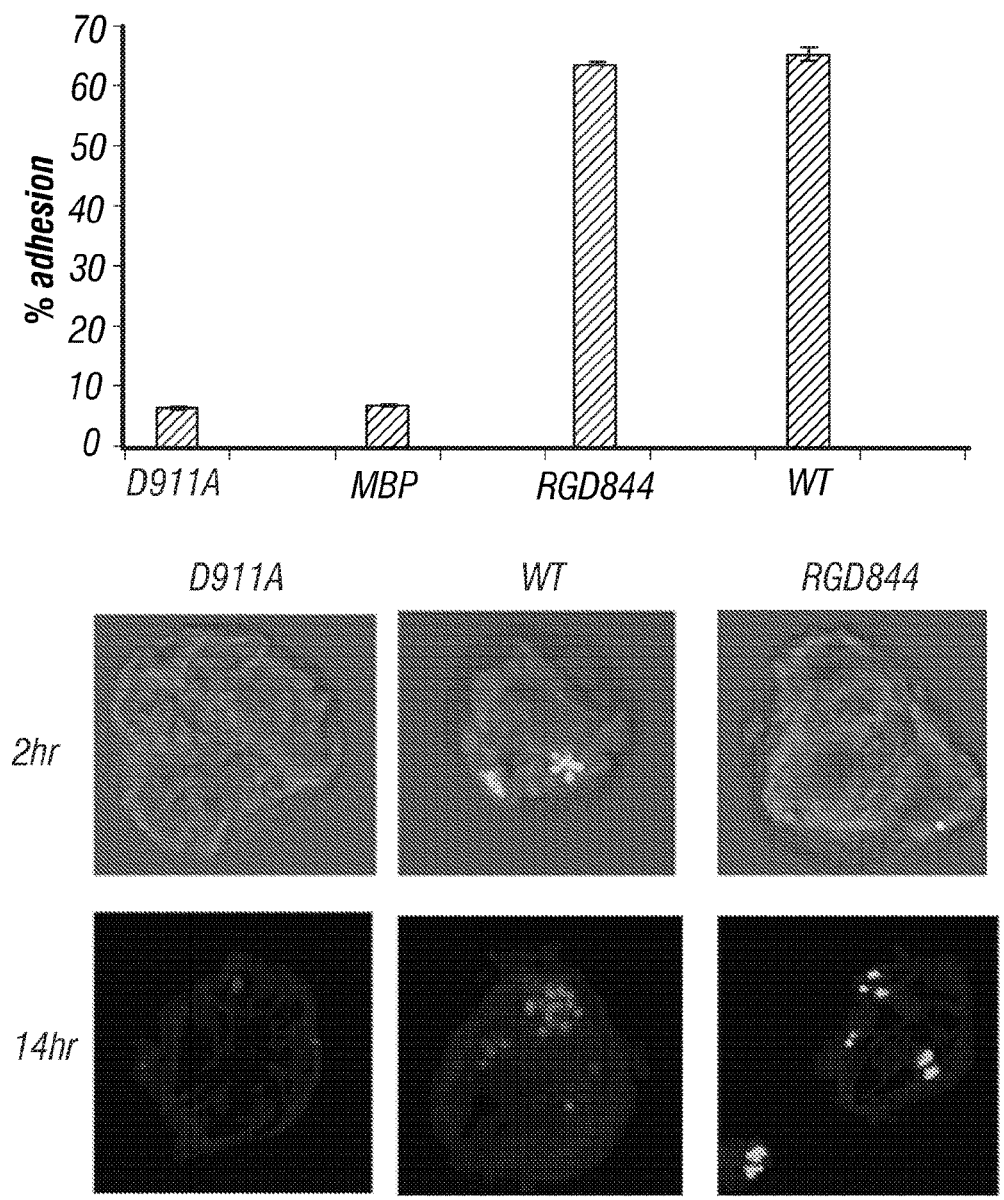
Figure 16:
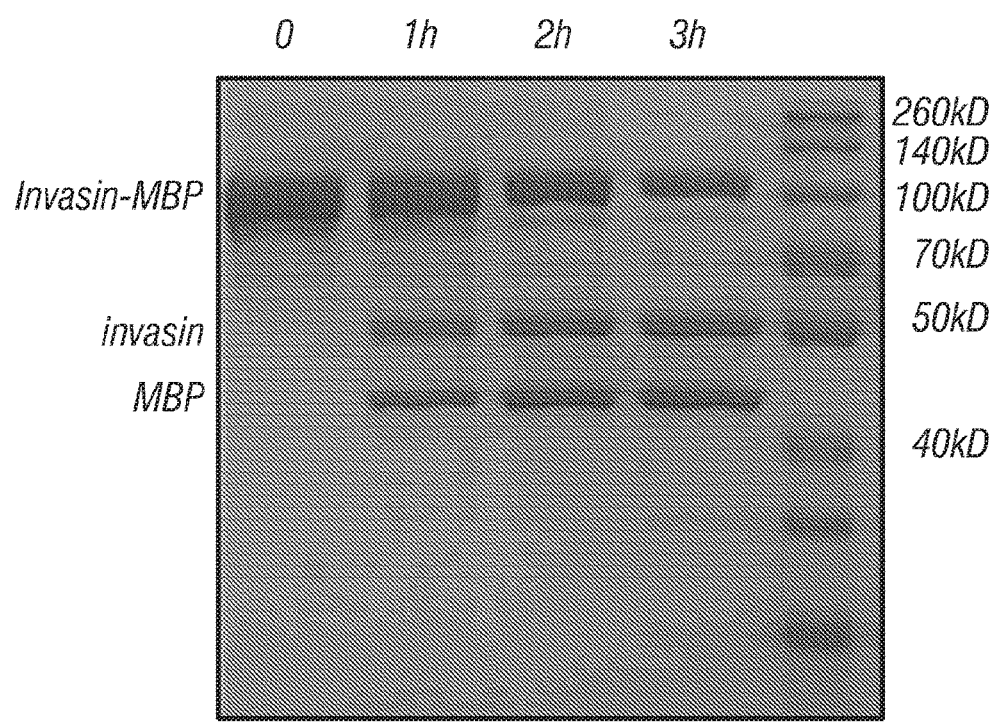
Figure 17:
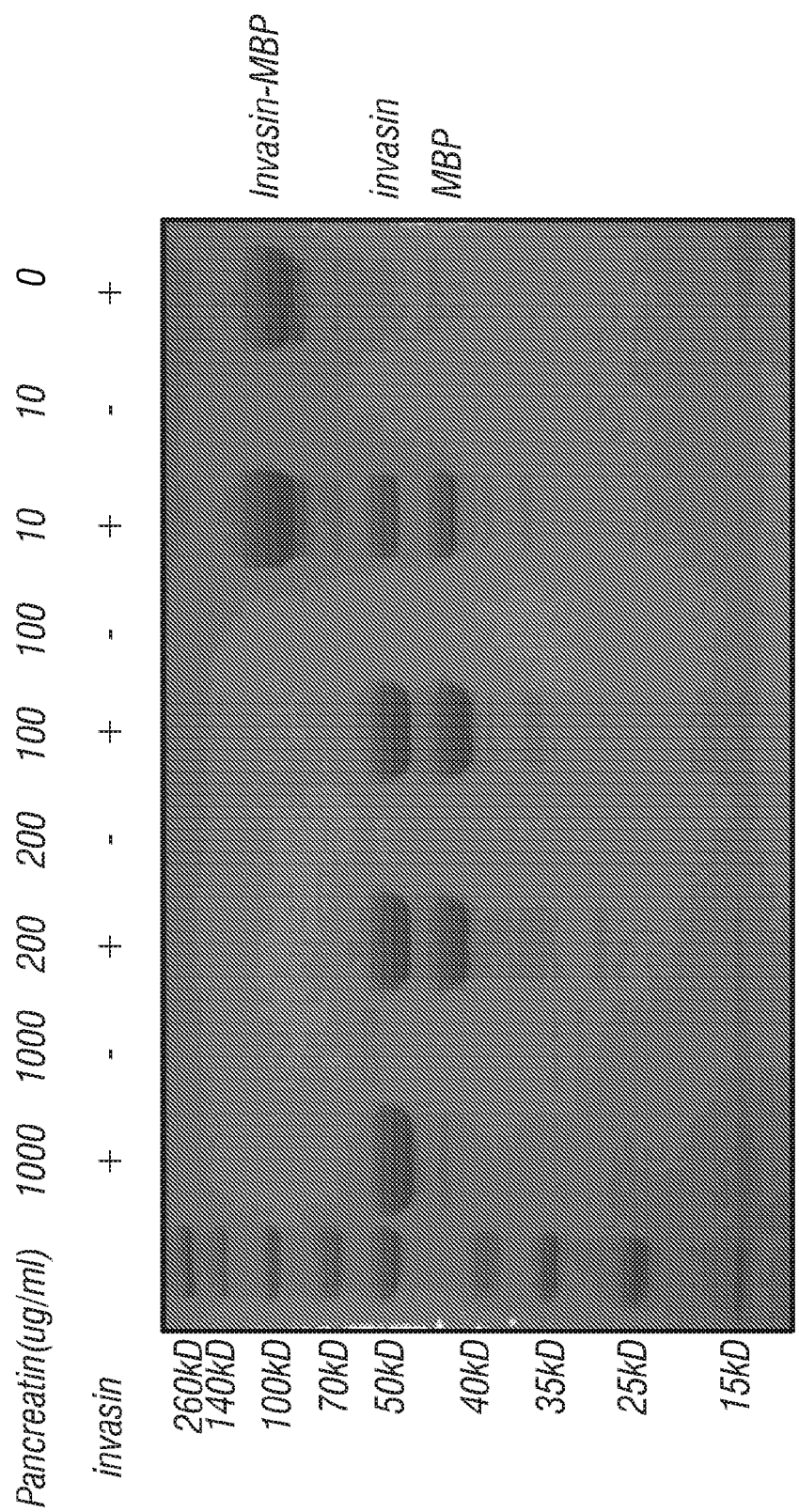
Figure 18:
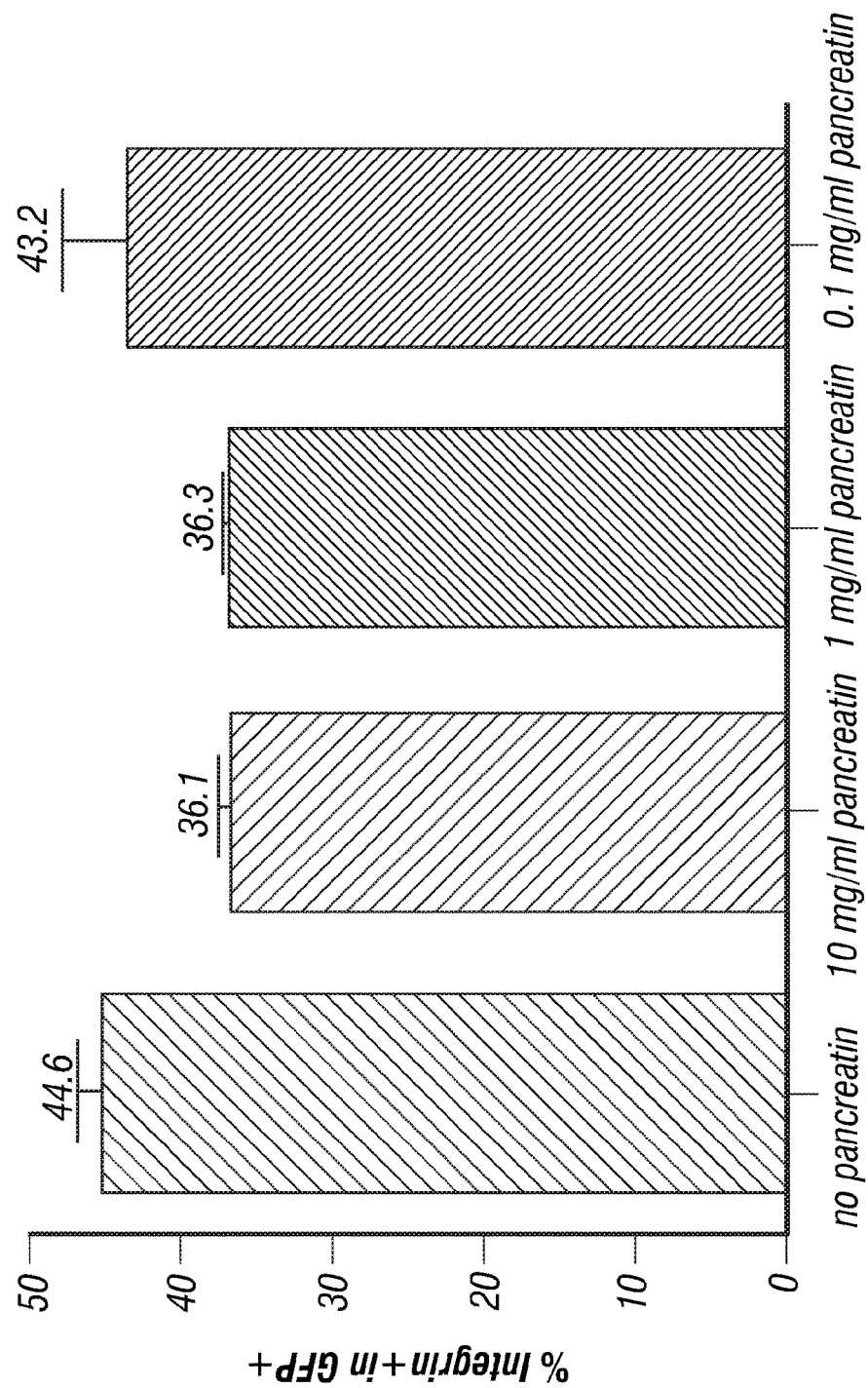

RGD motif alters cellular specificity, a set of stable CHO-K1 cell lines genetically modified to alter their integrin expression profiles was obtained. The CHO B2 line lacks expression of the as chain and has <2% of native fibronectin binding capacity (Schreiner et al., 1989). Derivatives of this line stably express the human as chain and/or $\beta_3$ integrin chains, resulting in lines with no $\alpha_5\beta_1$ expression (but retain expression of other $\beta_1$-containing integrins that can support internalization of Invasin coated bacteria), or defined levels of $\alpha_5\beta_1$, $\alpha_v\beta_3$ or $\alpha_5\beta_1$ and $\alpha_v\beta_3$ (Ly et al., 2003). These integrin expression profiles were confirmed using antibodies specific for the $\alpha_5\beta_1$ and $\alpha_v\beta_3$ chains and flow cytometry (FIGS. 13A-13C) and repeated the bacterial invasion assay with cells expressing WT, D911A and RGD Invasin variants (FIG. 7D).

In each case, bacteria expressing the RGD Invasin variant invaded CHO cells more efficiently than the WT Invasin, a difference which was highly significant for CHO-B2+$\alpha_5$ and CHO-B2+$\alpha_v\beta_3$+$\alpha_5$ lines (p<0.01; two-tailed t-test). Comparison of the cell lines showed first that invasion is increased by expression of the as integrin (p<0.05). Second, it also shows that the presence of $\alpha_v\beta_3$ reduces invasion when compared to the corresponding line only expressing $\alpha_5\beta_1$ or other $\alpha_v\beta_3$ integrins (B2 line; p<0.05). Notably, the Caco-2 line also expresses both $\alpha_5\beta_1$ and $\alpha_v\beta_3$ integrins. Together, these data suggest that binding to $\alpha_v\beta_3$ may inhibit $\beta_1$-mediated internalization via competitive inhibition or signaling cross-talk and may offset gains due to enhanced integrin affinity.

Figure 8A:
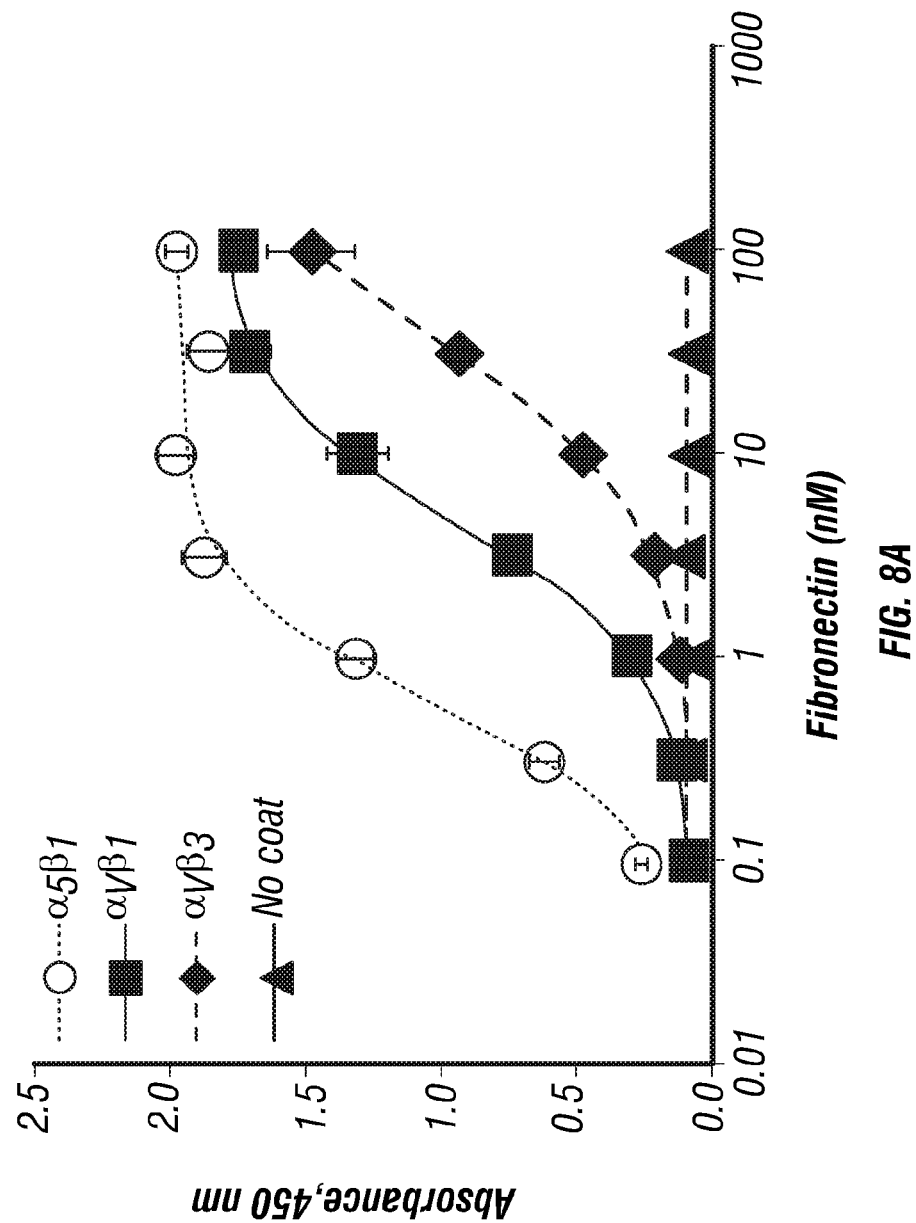
FIGS. 8A-8C—Fibronectin-integrin binding specificity. 8A, ELISA showing fibronectin binding affinity selected integrins. Purified fibronectin was titrated on plates coated with soluble $\alpha_5\beta_1$ (○), $\alpha_\nu\beta_1$ (■), $\alpha_\nu\beta_3$ integrins (▲) and no coat control (▼), followed by detection with anti-GST-HRP. 8B, Structural comparison of the Invasin and fibronectin RGD and synergy sites suggests a different structural engagement of integrins. The black line indicates the axis of the molecule, while the gray dashed line connects the critical aspartate residues in the primary and synergy sites. Figure made with PDB 1CWV and 1FNF using Pymol. 8C, Venn diagram comparing the integrin binding specificities of fibronectin and Invasin. Data from (Isberg and Leong, 1990; Hynes, 2002).
Figure 8B:
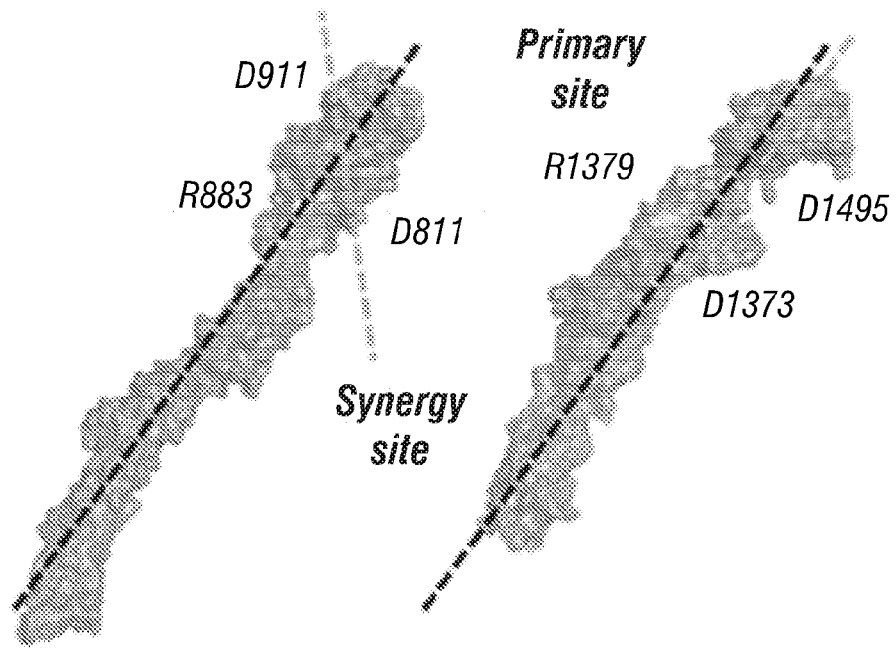
Figure 8C:
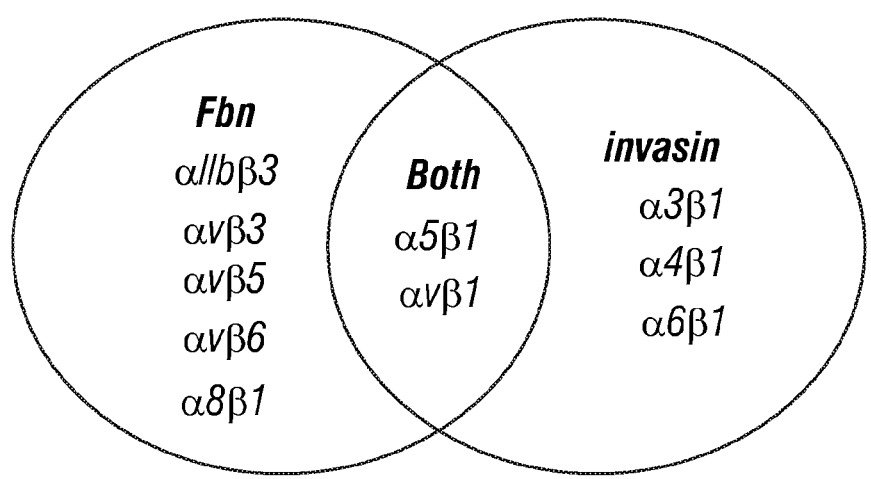

To compare the RGD Invasin to fibronectin, the ability of fibronectin to bind the same set of integrins was analyzed by ELISA. Fibronectin shows a similar affinity trend, with $\alpha_5\beta_1$>$\alpha_5\beta_1$>$\alpha_v\beta_3$ supporting the notion that the RGD increases Invasin promiscuity (FIG. 8A). To gain insight into the structural role of RGD in invasion, the structures of Invasin (PDB 1CWV) was compared with that of fibronectin (PDB 1FNF). Both proteins are elongated rods, with primary integrin binding sites located in the terminal domain (including the residues D911 and D1495, located in the RGD motif). Both proteins also present secondary synergy sites located about 32 Å away, containing additional aspartate and arginine residues important for integrin binding (D811 and R883 in Invasin; D1373 and R1379 in fibronectin). Interestingly, the relative positions of the primary and synergy sites appear different for Invasin and fibronectin. In Invasin, the two sites form a line defined by D911 and D811 which is offset from the axis the protein axis, while in fibronectin the two sites are from a line roughly parallel to the protein axis (FIG. 8B).

Example 3—Invasin Variants Resistant to Proteolysis

To determine if the Invasin from Examples 1-2 can be used to target vaccine antigens, such as in the context of an in vivo intestinal environment, proteolysis experiments were performed. First, Invasin was expressed as maltose binding protein (MBP) fusion protein and digested with trypsin for 1 h, 2 h or 3 h. SDS page analysis (FIG. 16) and mass spectrometry demonstrated that the digested product at 52 kD was Invasin, and the digested product at 41 kD was MBP.

Next, simulated intestinal fluid with different concentrations of the enzyme pancreatin was used to digest Invasin-MBP at 37° C. for 2 h. With the increase of pancreatin concentration, more Invasion-MBP was cut into Invasin and MBP, but Invasin itself was not cut into small pieces (FIG. 17).

Finally, Invasin display *E. coli* expressing a high level of GFP were digested with simulated intestinal fluid. Proteolytic resistant Invasin was labeled by fluorescent a5131 integrins. FACS was used to record the percentage of a5131 integrins positive in the digested *E. coli*. As the simulated intestinal fluid could not digest Invasin displayed on *E. coli*, the digested *E. coli* could still be labeled with fluorescent $\alpha_5\beta_1$ integrins indicating they retain the ability to bind M cells under realistic intestinal conditions (FIG. 18). Thus, Engineered Invasin is resistant to proteolysis by trypsin or other intestinal enzymes in buffer or simulated intestinal fluid conditions. These data support the use of Invasin provided herein for targeting vaccine antigens to M cells, such as in the context of an in vivo intestinal environment.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,680,338
U.S. Pat. No. 5,141,648
U.S. Pat. No. 5,563,250
U.S. Pat. No. 5,856,456
U.S. Pat. No. 5,880,270
Arai et al., 2004
Brayden et al., Keynote review: intestinal Peyer's patch M cells and oral vaccine targeting, *Drug Discov Today* 10, 1145-1157, 2005.
Clark et al., M-cell surface beta1 integrin expression and Invasin-mediated targeting of *Yersinia pseudotuberculosis* to mouse Peyer's patch M cells, *Infect Immun* 66, 1237-1243, 1998.
Critchley-Thorne et al., Recombinant *Escherichia coli* expressing Invasin targets the Peyer's patches: the basis for a bacterial formulation for oral vaccination, *Mol Ther* 14, 183-191, 2006.

Czerkinsky et al., *Ann. N.Y. Acad. Sci.*, 778:185-193, 1996

Dersch and Isberg, A region of the *Yersinia pseudotuberculosis* Invasin protein enhances integrin-mediated uptake into mammalian cells and promotes self-association, *EMBO J* 18, 1199-1213, 1999.

Dersch and Isberg, An immunoglobulin superfamily-like domain unique to the *Yersinia pseudotuberculosis* Invasin protein is required for stimulation of bacterial uptake via integrin receptors, *Infect Immun* 68, 2930-2938, 2000.

Dupuy and Caron, Integrin-dependent phagocytosis: spreading from microadhesion to new concepts, *Journal of cell science* 121, 1773-1783, 2008.

Fairman et al., Crystal structures of the outer membrane domain of intimin and Invasin from enterohemorrhagic *E. coli* and enteropathogenic *Y. pseudotuberculosis*, *Structure* 20, 1233-1243, 2012.

Felding-Habermann et al., A single immunoglobulin-like domain of the human neural cell adhesion molecule L1 supports adhesion by multiple vascular and platelet integrins, *J Cell Biol* 139, 1567-1581, 1997.

Guzman et al., Tight regulation, modulation, and high-level expression by vectors containing the arabinose PBAD promoter, *Journal of Bacteriology* 177, 4121-4130, 1995.

Hamburger et al., Crystal structure of Invasin: a bacterial integrin-binding protein, *Science* 286, 291-295, 1999.

Honore et al., Outside-in regulation of integrin clustering processes by ECM components per se and their involvement in actin cytoskeleton organization in a colon adenocarcinoma cell line, *Histochem Cell Biol* 114, 323-335, 2000.

Hynes, R. O, Integrins: bidirectional, allosteric signaling machines, *Cell* 110, 673-687, 2002.

Isberg and Leong, Multiple beta 1 chain integrins are receptors for Invasin, a protein that promotes bacterial penetration into mammalian cells, *Cell* 60, 861-871, 1990.

Isberg et al., Identification of Invasin: a protein that allows enteric bacteria to penetrate cultured mammalian cells, *Cell* 50, 769-778, 1987.

Isberg et al., Residues added to the carboxyl terminus of the *Yersinia pseudotuberculosis* Invasin protein interfere with recognition by integrin receptors, *J Biol Chem* 268, 15840-15846, 1993.

Kyte and Doolittle, 1982

Leahy et al., 2.0 A crystal structure of a four-domain segment of human fibronectin encompassing the RGD loop and synergy region, *Cell* 84, 155-164, 1996.

Leibiger et al., *Yersinia enterocolitica* Yop mutants as oral live carrier vaccines, *Vaccine* 26, 6664-6670, 2008.

Leong et al., An aspartate residue of the *Yersinia pseudotuberculosis* Invasin protein that is critical for integrin binding, *EMBO J* 14, 422-431, 1995.

Leong et al., Identification of the integrin binding domain of the *Yersinia pseudotuberculosis* Invasin protein, *EMBO J* 9, 1979-1989, 1990.

Levy et al., Production of correctly folded Fab antibody fragment in the cytoplasm of *Escherichia coli* trxB gor mutants via the coexpression of molecular chaperones, *Protein Expr Purif* 23, 338-347, 2001.

Lord et al., Analysis of the interaction between RGD-expressing adenovirus type 5 fiber knob domains and alphavbeta3 integrin reveals distinct binding profiles and intracellular trafficking, *J Gen Virol* 87, 2497-2505, 2006.

Ly et al., De novo expression of the integrin alpha5beta1 regulates alphavbeta3-mediated adhesion and migration on fibrinogen, *J Biol Chem* 278, 21878-21885, 2003.

Palumbo and Wang, Bacterial Invasin: structure, function, and implication for targeted oral gene delivery, *Current drug delivery* 3, 47-53, 2006.

Panthani et al., In vivo whole animal fluorescence imaging of a microparticle-based oral vaccine containing (CuInSe(x)S(2-x))/ZnS core/shell quantum dots, *Nano Lett* 13, 4294-4298, 2013.

Remington's Pharmaceutical Sciences, 18th Ed. Mack Printing Company, pp. 1289-1329, 1990.

Robinson et al., 1998

Ruoslahti and Pierschbacher, Arg-Gly-Asp: a versatile cell recognition signal, *Cell* 44, 517-518, 1986.

Ruoslahti, E., RGD and other recognition sequences for integrins, *Annual review of cell and developmental biology* 12, 697-715, 1996.

Saltman et al., A region of the *Yersinia pseudotuberculosis* Invasin protein that contributes to high affinity binding to integrin receptors, *J Biol Chem* 271, 23438-23444, 1996.

Schreiner et al., Isolation and characterization of Chinese hamster ovary cell variants deficient in the expression of fibronectin receptor, *J Cell Biol* 109, 3157-3167, 1989.

Schulte et al., Translocation of *Yersinia entrocolitica* across reconstituted intestinal epithelial monolayers is triggered by *Yersinia* Invasin binding to beta1 integrins apically expressed on M-like cells, *Cell Microbiol* 2, 173-185, 2000.

Sidhu and Weiss, Constructing phage display libraries by oligonucleotide-directed mutagenesis, In *Phage display: a practical approach* (Tim Clackson, H. B. L., Ed.), pp 27-42, Oxford University Press, Oxford, 2004.

Swiatkowska et al., Interaction and functional association of protein disulfide isomerase with alphaVbeta3 integrin on endothelial cells, *FEBS J* 275, 1813-1823, 2008.

Thorpe et al., 1987

Whitlow et al., 1993

What is claimed is:

1. A recombinant polypeptide comprising an Invasin D5 domain coding sequence at least 80% identical to amino acid residues 887-986 of SEQ ID NO: 1, wherein the Invasin D5 domain coding sequence comprises an amino acid substitution at the position corresponding to Gly 909 and/or an amino acid substitution at the position corresponding to Ser 910.

2. The polypeptide of claim 1, wherein the polypeptide comprises an amino acid substitution at the position corresponding to Gly 909 and an amino acid substitution at the position corresponding to Ser 910.

3. The polypeptide of claim 1, wherein the polypeptide comprises an amino acid substitution for a residue having a positively charged side chain at the position corresponding to Gly 909.

4. The polypeptide of claim 3, wherein the polypeptide comprises an Arg substitution at the position corresponding to Gly 909.

5. The polypeptide of claim 1, wherein the polypeptide comprises an amino acid substitution for an aliphatic residue at the position corresponding to Ser 910.

6. The polypeptide of claim 5, wherein the polypeptide comprises a Gly substitution at the position corresponding to Ser 910.

7. The polypeptide of claim 2, wherein the polypeptide comprises an Arg substitution at the position corresponding to Gly 909 and a Gly substitution at the position corresponding to Ser 910.

8. The polypeptide of claim 7, wherein the polypeptide comprises a $^{909}$RGD$^{911}$ motif.

9. The polypeptide of claim 8, wherein the $^{909}$RGD$^{911}$ motif increases integrin binding affinity by at least 10 fold as compared to wild-type Invasin.

10. The polypeptide of claim 8, wherein the $^{909}$RGD$^{911}$ motif increases integrin binding affinity by at least 50 fold as compared to wild-type Invasin.

11. The polypeptide of claim 8, wherein the $^{909}$RGD$^{911}$ motif increases integrin binding affinity by at least 1000 fold as compared to wild-type Invasin.

12. The polypeptide of claim 1, further comprising an Invasin D4 coding sequence at least 80% identical to amino acid residues 795-886 of SEQ ID NO: 1.

13. The polypeptide of claim 12, wherein the Invasin D4 coding sequence comprises one or more of the following features:

(a) an amino acid substitution at the position corresponding to Phe 844;

(b) an amino acid substitution at the position corresponding to Tyr 878; or (c) an amino acid substitution at the position corresponding to Tyr 885.

14. The polypeptide of claim 12, wherein the polypeptide comprises an amino acid substitution for a residue having a hydrophobic side chain at the position corresponding to Phe 844.

15. The polypeptide of claim 14, wherein the polypeptide comprises a Tyr substitution at the position corresponding to Phe 844.

16. A composition comprising a polypeptide of claim 1 in a pharmaceutically acceptable carrier.

17. A method for the delivery of a therapeutic agent to a subject comprising administering a therapeutic agent and a polypeptide of claim 1 to the subject.

18. A method of eliciting an immune response in a subject comprising administering at least one antigen and an Invasin polypeptide according to claim 1 to the subject.

19. The method of claim 18, wherein the antigen is associated with a disease.

20. The method of claim 19, wherein the disease is an infectious diseases, autoimmune disease, allergy, or cancer.

* * * * *

SEQUENCE LISTING

<160> NUMBER OF SEQ ID NOS: 11

<210> SEQ ID NO 1
<211> LENGTH: 986
<212> TYPE: PRT
<213> ORGANISM: Yersinia pseudotuberculosis

<400> SEQUENCE: 1

Met Met Val Phe Gln Pro Ile Ser Glu Phe Leu Leu Ile Arg Asn Ala
1               5                   10                  15

Gly Met Ser Met Tyr Phe Asn Lys Ile Ile Ser Phe Asn Ile Ile Ser
            20                  25                  30

-continued

```
Arg Ile Val Ile Cys Ile Phe Leu Ile Cys Gly Met Phe Met Ala Gly
            35                  40                  45

Ala Ser Glu Lys Tyr Asp Ala Asn Ala Pro Gln Gln Val Gln Pro Tyr
 50                  55                  60

Ser Val Ser Ser Ser Ala Phe Glu Asn Leu His Pro Asn Asn Glu Met
 65                  70                  75                  80

Glu Ser Ser Ile Asn Pro Phe Ser Ala Ser Asp Thr Glu Arg Asn Ala
                 85                  90                  95

Ala Ile Ile Asp Arg Ala Asn Lys Glu Gln Glu Thr Glu Ala Val Asn
                100                 105                 110

Lys Met Ile Ser Thr Gly Ala Arg Leu Ala Ala Ser Gly Arg Ala Ser
                115                 120                 125

Asp Val Ala His Ser Met Val Gly Asp Ala Val Asn Gln Glu Ile Lys
                130                 135                 140

Gln Trp Leu Asn Arg Phe Gly Thr Ala Gln Val Asn Leu Asn Phe Asp
145                 150                 155                 160

Lys Asn Phe Ser Leu Lys Glu Ser Ser Leu Asp Trp Leu Ala Pro Trp
                165                 170                 175

Tyr Asp Ser Ala Ser Phe Leu Phe Phe Ser Gln Leu Gly Ile Arg Asn
                180                 185                 190

Lys Asp Ser Arg Asn Thr Leu Asn Leu Gly Val Gly Ile Arg Thr Leu
                195                 200                 205

Glu Asn Gly Trp Leu Tyr Gly Leu Asn Thr Phe Tyr Asp Asn Asp Leu
    210                 215                 220

Thr Gly His Asn His Arg Ile Gly Leu Gly Ala Glu Ala Trp Thr Asp
225                 230                 235                 240

Tyr Leu Gln Leu Ala Ala Asn Gly Tyr Phe Arg Leu Asn Gly Trp His
                245                 250                 255

Ser Ser Arg Asp Phe Ser Asp Tyr Lys Glu Arg Pro Ala Thr Gly Gly
                260                 265                 270

Asp Leu Arg Ala Asn Ala Tyr Leu Pro Ala Leu Pro Gln Leu Gly Gly
                275                 280                 285

Lys Leu Met Tyr Glu Gln Tyr Thr Gly Glu Arg Val Ala Leu Phe Gly
                290                 295                 300

Lys Asp Asn Leu Gln Arg Asn Pro Tyr Ala Val Thr Ala Gly Ile Asn
305                 310                 315                 320

Tyr Thr Pro Val Pro Leu Leu Thr Val Gly Val Asp Gln Arg Met Gly
                325                 330                 335

Lys Ser Ser Lys His Glu Thr Gln Trp Asn Leu Gln Met Asn Tyr Arg
                340                 345                 350

Leu Gly Glu Ser Phe Gln Ser Gln Leu Ser Pro Ser Ala Val Ala Gly
                355                 360                 365

Thr Arg Leu Leu Ala Glu Ser Arg Tyr Asn Leu Val Asp Arg Asn Asn
                370                 375                 380

Asn Ile Val Leu Glu Tyr Gln Lys Gln Val Val Lys Leu Thr Leu
385                 390                 395                 400

Ser Pro Ala Thr Ile Ser Gly Leu Pro Gly Gln Val Tyr Gln Val Asn
                405                 410                 415

Ala Gln Val Gln Gly Ala Ser Ala Val Arg Glu Ile Val Trp Ser Asp
                420                 425                 430

Ala Glu Leu Ile Ala Ala Gly Gly Thr Leu Thr Pro Leu Ser Thr Thr
                435                 440                 445
```

-continued

```
Gln Phe Asn Leu Val Leu Pro Pro Tyr Lys Arg Thr Ala Gln Val Ser
450                 455                 460
Arg Val Thr Asp Asp Leu Thr Ala Asn Phe Tyr Ser Leu Ser Ala Leu
465                 470                 475                 480
Ala Val Asp His Gln Gly Asn Arg Ser Asn Ser Phe Thr Leu Ser Val
                485                 490                 495
Thr Val Gln Gln Pro Gln Leu Thr Leu Thr Ala Ala Val Ile Gly Asp
            500                 505                 510
Gly Ala Pro Ala Asn Gly Lys Thr Ala Ile Thr Val Glu Phe Thr Val
            515                 520                 525
Ala Asp Phe Glu Gly Lys Pro Leu Ala Gly Gln Glu Val Val Ile Thr
530                 535                 540
Thr Asn Asn Gly Ala Leu Pro Asn Lys Ile Thr Glu Lys Thr Asp Ala
545                 550                 555                 560
Asn Gly Val Ala Arg Ile Ala Leu Thr Asn Thr Thr Asp Gly Val Thr
                565                 570                 575
Val Val Thr Ala Glu Val Glu Gly Gln Arg Gln Ser Val Asp Thr His
            580                 585                 590
Phe Val Lys Gly Thr Ile Ala Ala Asp Lys Ser Thr Leu Ala Ala Val
            595                 600                 605
Pro Thr Ser Ile Ile Ala Asp Gly Leu Met Ala Ser Thr Ile Thr Leu
610                 615                 620
Glu Leu Lys Asp Thr Tyr Gly Asp Pro Gln Ala Gly Ala Asn Val Ala
625                 630                 635                 640
Phe Asp Thr Thr Leu Gly Asn Met Gly Val Ile Thr Asp His Asn Asp
                645                 650                 655
Gly Thr Tyr Ser Ala Pro Leu Thr Ser Thr Thr Leu Gly Val Ala Thr
            660                 665                 670
Val Thr Val Lys Val Asp Gly Ala Ala Phe Ser Val Pro Ser Val Thr
            675                 680                 685
Val Asn Phe Thr Ala Asp Pro Ile Pro Asp Ala Gly Arg Ser Ser Phe
690                 695                 700
Thr Val Ser Thr Pro Asp Ile Leu Ala Asp Gly Thr Met Ser Ser Thr
705                 710                 715                 720
Leu Ser Phe Val Pro Val Asp Lys Asn Gly His Phe Ile Ser Gly Met
                725                 730                 735
Gln Gly Leu Ser Phe Thr Gln Asn Gly Val Pro Val Ser Ile Ser Pro
            740                 745                 750
Ile Thr Glu Gln Pro Asp Ser Tyr Thr Ala Thr Val Val Gly Asn Ser
            755                 760                 765
Val Gly Asp Val Thr Ile Thr Pro Gln Val Asp Thr Leu Ile Leu Ser
770                 775                 780
Thr Leu Gln Lys Lys Ile Ser Leu Phe Pro Val Pro Thr Leu Thr Gly
785                 790                 795                 800
Ile Leu Val Asn Gly Gln Asn Phe Ala Thr Asp Lys Gly Phe Pro Lys
                805                 810                 815
Thr Ile Phe Lys Asn Ala Thr Phe Gln Leu Gln Met Asp Asn Asp Val
            820                 825                 830
Ala Asn Asn Thr Gln Tyr Glu Trp Ser Ser Phe Thr Pro Asn Val
            835                 840                 845
Ser Val Asn Asp Gln Gly Gln Val Thr Ile Thr Tyr Gln Thr Tyr Ser
850                 855                 860
Glu Val Ala Val Thr Ala Lys Ser Lys Lys Phe Pro Ser Tyr Ser Val
```

```
            865                 870                 875                 880
Ser Tyr Arg Phe Tyr Pro Asn Arg Trp Ile Tyr Asp Gly Gly Arg Ser
                    885                 890                 895

Leu Val Ser Ser Leu Glu Ala Ser Arg Gln Cys Gln Gly Ser Asp Met
                900                 905                 910

Ser Ala Val Leu Glu Ser Ser Arg Ala Thr Asn Gly Thr Arg Ala Pro
            915                 920                 925

Asp Gly Thr Leu Trp Gly Glu Trp Gly Ser Leu Thr Ala Tyr Ser Ser
        930                 935                 940

Asp Trp Gln Ser Gly Glu Tyr Trp Val Lys Lys Thr Ser Thr Asp Phe
945                 950                 955                 960

Glu Thr Met Asn Met Asp Thr Gly Ala Leu Gln Pro Gly Pro Ala Tyr
                965                 970                 975

Leu Ala Phe Pro Leu Cys Ala Leu Ser Ile
            980                 985

<210> SEQ ID NO 2
<211> LENGTH: 18
<212> TYPE: PRT
<213> ORGANISM: Artificial Sequence
<220> FEATURE:
<223> OTHER INFORMATION: Synthetic peptide (218 linker)

<400> SEQUENCE: 2

Gly Ser Thr Ser Gly Ser Gly Lys Pro Gly Ser Gly Glu Gly Ser Thr
1               5                   10                  15

Lys Gly

<210> SEQ ID NO 3
<211> LENGTH: 5
<212> TYPE: PRT
<213> ORGANISM: Artificial Sequence
<220> FEATURE:
<223> OTHER INFORMATION: Synthetic peptide (HL linker)

<400> SEQUENCE: 3

Glu Ala Ala Ala Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic peptide

<400> SEQUENCE: 4

Gly Gly Gly Gly Ser
1               5

<210> SEQ ID NO 5
<211> LENGTH: 35
<212> TYPE: DNA
<213> ORGANISM: Artificial Sequence
<220> FEATURE:
<223> OTHER INFORMATION: Synthetic primer

<400> SEQUENCE: 5
agctatcgag ctcgaactca ttcacattga gcgtc                              35

<210> SEQ ID NO 6
<211> LENGTH: 48
```

<212> TYPE: DNA
<213> ORGANISM: Artificial Sequence
<220> FEATURE:
<223> OTHER INFORMATION: primer

<400> SEQUENCE: 6
cgtcattata ccatggctag ttaatcatta tattgacagc gcacagag          48

<210> SEQ ID NO 7
<211> LENGTH: 54
<212> TYPE: DNA
<213> ORGANISM: Artificial Sequence
<220> FEATURE:
<223> OTHER INFORMATION: Synthetic primer

<400> SEQUENCE: 7
taactgacga tctagaactt taagaaggag atataccatg atggttttcc agcc    54

<210> SEQ ID NO 8
<211> LENGTH: 53
<212> TYPE: DNA
<213> ORGANISM: Artificial Sequence
<220> FEATURE:
<223> OTHER INFORMATION: Synthetic primer

<400> SEQUENCE: 8
tacgatgtct aatgtatgca tgctcaatta ttcattatat tgacagcgca cag     53

<210> SEQ ID NO 9
<211> LENGTH: 742
<212> TYPE: PRT
<213> ORGANISM: Yersinia enterocolitica

<400> SEQUENCE: 9

Met Thr Ser Phe Phe Asn Thr Leu Thr Val Thr Lys Ile Ile Ser Arg
1 5 10 15

Leu Ile Leu Ser Ile Gly Leu Ile Phe Gly Ile Phe Thr Tyr Gly Phe
20 25 30

Ser Gln Cys His Tyr Phe Asn Ser Glu Ala Leu Glu Asn Pro Ala Glu
35 40 45

His Asn Gly Ala Gly Val Arg Thr Phe Gln Gln Ser Trp Met Tyr Gly
50 55 60

Phe Asn Thr Phe Tyr Asp Asn Asp Met Thr Gly His Asn His Arg Ile
65 70 75 80

Gly Val Gly Ala Glu Ala Trp Thr Asp Tyr Leu Gln Leu Ser Ala Asn
85 90 95

Gly Tyr Phe Arg Leu Asn Gly Trp His Gln Ser Arg Asp Phe Ala Asp
100 105 110

Tyr Asn Glu Arg Pro Ala Ser Gly Gly Asp Ile His Val Lys Ala Tyr
115 120 125

Leu Pro Ala Leu Pro Gln Leu Gly Gly Lys Leu Lys Tyr Glu Gln Tyr
130 135 140

Arg Gly Glu Arg Val Ala Leu Phe Gly Lys Asp Asn Leu Gln Ser Asn
145 150 155 160

Pro Tyr Ala Val Thr Thr Gly Leu Ile Tyr Thr Pro Ile Pro Phe Ile
165 170 175

Thr Leu Gly Val Asp Gln Arg Met Gly Lys Ser Arg Gln His Glu Ile
180 185 190

Gln Trp Asn Leu Gln Met Asp Tyr Arg Leu Gly Glu Ser Phe Arg Ser
195 200 205

```
Gln Phe Ser Pro Ala Val Val Ala Gly Thr Arg Leu Leu Ala Glu Ser
    210                 215                 220

Arg Tyr Asn Leu Val Glu Arg Asn Pro Asn Ile Val Leu Glu Tyr Gln
225                 230                 235                 240

Lys Gln Asn Thr Ile Lys Leu Ala Phe Ser Pro Ala Val Leu Ser Gly
                245                 250                 255

Leu Pro Gly Gln Val Tyr Ser Val Ser Ala Gln Ile Gln Ser Gln Ala
            260                 265                 270

Leu Gln Arg Ile Leu Trp Asn Asp Ala Gln Trp Val Ala Ala Gly Gly
        275                 280                 285

Lys Leu Ile Pro Val Ser Ala Thr Asp Tyr Asn Val Val Leu Pro Pro
290                 295                 300

Tyr Lys Pro Met Ala Pro Ala Ser Arg Thr Val Gly Lys Thr Gly Glu
305                 310                 315                 320

Ser Glu Ala Ala Val Asn Thr Tyr Thr Leu Ser Ala Thr Ala Ile Asp
                325                 330                 335

Asn His Gly Asn Ser Ser Asn Pro Ala Thr Leu Thr Val Ile Val Gln
            340                 345                 350

Gln Pro Gln Phe Val Ile Thr Ser Glu Val Thr Asp Asp Gly Ala Leu
        355                 360                 365

Ala Asp Gly Arg Thr Pro Ile Thr Val Lys Phe Asn Thr Val Thr Asn
370                 375                 380

Ile Asp Ser Thr Pro Val Ala Glu Gln Glu Gly Val Ile Thr Thr Ser
385                 390                 395                 400

Asn Gly Ala Leu Pro Ser Lys Val Thr Lys Thr Asp Ala Gln Gly
                405                 410                 415

Val Ile Ser Ile Ala Leu Thr Ser Phe Thr Val Gly Val Ser Val Val
            420                 425                 430

Thr Leu Asp Ile Gln Gly Gln Gln Ala Thr Val Asp Val Arg Phe Ala
        435                 440                 445

Val Leu Pro Pro Asp Val Thr Asn Ser Ser Phe Asn Val Ser Pro Ser
450                 455                 460

Asp Ile Val Ala Asp Gly Ser Met Gln Ser Ile Leu Thr Phe Val Pro
465                 470                 475                 480

Arg Asn Lys Asn Asn Glu Phe Val Ser Gly Ile Thr Asp Leu Glu Phe
                485                 490                 495

Ile Gln Ser Gly Val Pro Val Thr Ile Ser Ser Val Thr Glu Asn Ala
            500                 505                 510

Asp Asn Tyr Thr Ala Ser Val Val Gly Asn Ser Val Gly Asp Val Asp
        515                 520                 525

Ile Thr Thr Gln Val Gly Gly Glu Ser Leu Asp Leu Leu Gln Lys Arg
530                 535                 540

Ile Thr Leu Tyr Pro Val Pro Ile Thr Gly Ile Lys Val Asn Gly Glu
545                 550                 555                 560

Gln Phe Ala Thr Asp Lys Gly Phe Pro Lys Thr Phe Asn Lys Ala
                565                 570                 575

Thr Phe Gln Leu Val Met Asn Asp Asp Val Ala Asn Asn Thr Gln Tyr
            580                 585                 590

Asp Trp Thr Ser Ser Tyr Ala Ala Ser Ala Pro Val Asp Asn Gln Gly
        595                 600                 605

Lys Val Asn Ile Ala Tyr Lys Thr Tyr Gly Ser Thr Val Thr Val Thr
610                 615                 620
```

Ala Lys Ser Lys Lys Phe Pro Ser Tyr Thr Ala Thr Tyr Gln Phe Lys
625                 630                 635                 640

Pro Asn Leu Trp Val Phe Ser Gly Thr Met Ser Ser Leu Gln Ser Ser
            645                 650                 655

Val Glu Ala Ser Arg Asn Cys Gln Arg Thr Asp Phe Thr Ala Leu Ile
        660                 665                 670

Glu Ser Ala Arg Ala Ser Asn Gly Ser Arg Ser Pro Asp Gly Thr Leu
    675                 680                 685

Trp Gly Glu Trp Gly Ser Leu Ala Thr Tyr Asp Ser Ala Glu Trp Pro
690                 695                 700

Ser Gly Asn Tyr Trp Thr Lys Lys Thr Ser Thr Asp Phe Val Thr Asn
705                 710                 715                 720

Asp Met Thr Thr Gly Asp Ile Pro Thr Ser Ala Ala Thr Ala Tyr Pro
            725                 730                 735

Leu Cys Ala Glu Pro Gln
            740

<210> SEQ ID NO 10
<211> LENGTH: 785
<212> TYPE: PRT
<213> ORGANISM: Yersinia pseudotuberculosis

<400> SEQUENCE: 10

Met Val Phe Gln Pro Ile Ser Glu Phe Leu Leu Ile Arg Asn Ala Gly
1               5                   10                  15

Met Ser Met Tyr Phe Asn Lys Ile Ile Ser Phe Asn Ile Ile Ser Arg
            20                  25                  30

Ile Val Ile Cys Ile Phe Leu Ile Cys Gly Met Phe Met Ala Gly Ala
        35                  40                  45

Ser Glu Lys Tyr Asp Ala Asn Ala Pro Gln Gln Val Gln Pro Tyr Ser
    50                  55                  60

Val Ser Ser Ala Phe Glu Asn Leu His Pro Asn Asn Glu Met Glu
65              70                  75                  80

Ser Ser Ile Asn Pro Phe Ser Ala Ser Asp Thr Glu Arg Asn Ala Ala
            85                  90                  95

Ile Ile Asp Arg Gly Val Gly Ile Arg Thr Leu Glu Asn Gly Trp Leu
        100                 105                 110

Tyr Gly Leu Asn Thr Phe Tyr Asp Asn Asp Leu Thr Gly His Asn His
    115                 120                 125

Arg Ile Gly Leu Gly Ala Glu Ala Trp Thr Asp Tyr Leu Gln Leu Ala
130                 135                 140

Ala Asn Gly Tyr Phe Arg Leu Asn Gly Trp His Ser Ser Arg Asp Phe
145                 150                 155                 160

Ser Asp Tyr Lys Glu Arg Pro Ala Thr Gly Gly Asp Leu Arg Ala Asn
            165                 170                 175

Ala Tyr Leu Pro Ala Leu Pro Gln Leu Gly Gly Lys Leu Met Tyr Glu
        180                 185                 190

Gln Tyr Thr Gly Glu Arg Val Ala Pro Ala Thr Ile Ser Gly Leu Pro
    195                 200                 205

Gly Gln Val Thr Gln Asn Val Ala Gln Val Gly Ala Ser Ala Val
210                 215                 220

Arg Glu Ile Val Trp Ser Asp Ala Glu Leu Ile Ala Ala Gly Gly Thr
225                 230                 235                 240

Leu Thr Pro Leu Ser Thr Thr Gln Phe Asn Leu Val Leu Pro Pro Tyr
            245                 250                 255

```
Lys Arg Thr Ala Gln Val Ser Arg Val Thr Asp Asp Leu Thr Ala Asn
            260                 265                 270

Phe Tyr Ser Leu Ser Ala Leu Ala Val Asp His Gln Gly Asn Arg Ser
            275                 280                 285

Asn Ser Phe Thr Leu Ser Val Thr Val Gln Gln Pro Gln Leu Thr Leu
            290                 295                 300

Thr Ala Ala Val Ile Gly Asp Gly Ala Pro Ala Asn Gly Lys Thr Ala
305                 310                 315                 320

Ile Thr Val Glu Phe Thr Val Ala Asp Phe Glu Gly Lys Pro Leu Ala
            325                 330                 335

Gly Gln Glu Val Val Ile Thr Thr Asn Asn Gly Ala Leu Pro Asn Lys
            340                 345                 350

Ile Thr Glu Lys Thr Asp Ala Asn Gly Val Ala Arg Ile Ala Leu Thr
            355                 360                 365

Asn Thr Thr Asp Gly Val Thr Val Thr Ala Glu Val Glu Gly Gln
            370                 375                 380

Arg Gln Ser Val Asp Thr His Phe Val Lys Gly Thr Ile Ala Ala Asp
385                 390                 395                 400

Lys Ser Thr Leu Ala Ala Val Pro Thr Ser Ile Ile Ala Asp Gly Leu
            405                 410                 415

Met Ala Ser Thr Ile Thr Leu Glu Leu Lys Asp Thr Tyr Gly Asp Pro
            420                 425                 430

Gln Ala Gly Ala Asn Val Ala Phe Asp Thr Thr Leu Gly Asn Met Gly
            435                 440                 445

Val Ile Thr Asp His Asn Asp Gly Thr Tyr Ser Ala Pro Leu Thr Ser
            450                 455                 460

Thr Thr Leu Gly Val Ala Thr Val Thr Val Lys Val Asp Gly Ala Ala
465                 470                 475                 480

Phe Ser Val Pro Ser Val Thr Val Asn Phe Thr Ala Asp Pro Ile Pro
            485                 490                 495

Asp Ala Gly Arg Ser Ser Phe Thr Val Ser Thr Pro Asp Ile Leu Ala
            500                 505                 510

Asp Gly Thr Asn Ser Ser Thr Leu Ser Phe Val Pro Val Asp Lys Asn
            515                 520                 525

Gly His Phe Ile Ser Gly Met Gln Gly Leu Ser Phe Thr Gln Asn Gly
            530                 535                 540

Val Pro Val Ser Ile Ser Pro Ile Thr Glu Gln Pro Asp Ser Tyr Thr
545                 550                 555                 560

Ala Thr Val Val Gly Asn Thr Ala Gly Asp Val Thr Ile Thr Pro Gln
            565                 570                 575

Val Asp Thr Leu Ile Leu Ser Thr Leu Gln Lys Lys Ile Ser Leu Phe
            580                 585                 590

Pro Val Pro Leu Thr Phe Ile Leu Val Asn Gly Gln Asn Phe Ala Thr
            595                 600                 605

Asp Lys Gly Phe Pro Lys Thr Ile Phe Lys Asn Ala Thr Phe Gln Leu
            610                 615                 620

Gln Met Asp Asn Asp Val Ala Asn Asn Thr Gln Tyr Glu Trp Ser Ser
625                 630                 635                 640

Ser Phe Thr Pro Asn Val Ser Val Asn Asp Gln Gly Gln Val Thr Ile
            645                 650                 655

Thr Tyr Gln Thr Tyr Ser Glu Val Ala Val Thr Ala Lys Ser Lys Lys
            660                 665                 670
```

-continued

```
Phe Pro Ser Tyr Ser Val Ser Tyr Arg Phe Tyr Pro Asn Arg Trp Ile
                675                 680                 685

Tyr Asp Gly Gly Thr Ser Ser Leu Val Ser Ser Leu Glu Ala Ser Arg
690                 695                 700

Gln Cys Gln Gly Ser Asp Met Ser Ala Val Leu Glu Ser Ser Arg Ala
705                 710                 715                 720

Thr Asn Gly Thr Arg Ala Pro Asp Gly Thr Leu Trp Gly Glu Trp Gly
                725                 730                 735

Ser Leu Thr Ala Tyr Ser Ser Asp Trp Gln Ser Gly Glu Tyr Trp Val
                740                 745                 750

Lys Lys Thr Ser Thr Asp Phe Glu Thr Met Asn Met Asp Thr Gly Ala
                755                 760                 765

Leu Val Gln Gly Pro Ala Tyr Leu Ala Phe Pro Leu Cys Ala Leu Ala
                770                 775                 780

Ile
785

<210> SEQ ID NO 11
<211> LENGTH: 542
<212> TYPE: PRT
<213> ORGANISM: Artificial sequence
<220> FEATURE:
<223> OTHER INFORMATION: Synthetic polypeptide

<400> SEQUENCE: 11

Met Phe Phe Asn Ile Ile Ser Arg Ile Ile Ile Leu Ile Gly
1               5                   10                  15

Ile Phe Gly Ser His Asn Ala Ala Glu Asn Asn Gly Gly Ile Arg Thr
                20                  25                  30

Asn Trp Leu Tyr Gly Asn Thr Phe Tyr Asp Asn Asp Leu Thr Gly His
                35                  40                  45

Asn His Arg Ile Gly Leu Gly Ala Glu Ala Trp Thr Asp Tyr Leu Gln
50                  55                  60

Leu Ala Ala Asn Gly Tyr Phe Arg Leu Asn Gly Trp His Ser Arg Asp
65                  70                  75                  80

Phe Ala Asp Tyr Glu Arg Pro Ala Ser Gly Gly Asp Ile Ala Tyr Leu
                85                  90                  95

Pro Ala Leu Pro Gln Leu Gly Gly Lys Leu Tyr Glu Gln Tyr Gly Glu
                100                 105                 110

Arg Val Ala Leu Phe Gly Lys Asp Asn Leu Gln Asn Pro Tyr Ala Val
                115                 120                 125

Thr Gly Ile Tyr Thr Pro Ile Pro Ile Thr Leu Gly Val Asp Gln Arg
130                 135                 140

Met Gly Lys Ser His Glu Gln Trp Asn Leu Gln Met Tyr Arg Leu Gly
145                 150                 155                 160

Glu Ser Phe Ser Gln Ser Pro Ala Val Ala Gly Thr Arg Leu Leu Ala
                165                 170                 175

Glu Ser Arg Tyr Asn Leu Val Asp Arg Asn Asn Ile Val Leu Glu Tyr
                180                 185                 190

Gln Lys Gln Asn Ile Lys Leu Ser Pro Ala Ile Ser Gly Leu Pro Gly
                195                 200                 205

Gln Val Tyr Val Ala Gln Ile Gln Ser Ala Leu Ile Leu Trp Asp Ala
                210                 215                 220

Ile Ala Ala Gly Gly Leu Pro Leu Ser Thr Phe Asn Leu Val Leu Pro
225                 230                 235                 240
```

-continued

```
Pro Tyr Lys Ala Ser Arg Asp Asn Tyr Ser Leu Ser Ala Ala Ile Asp
                245                 250                 255

Gly Asn Ser Asn Thr Leu Ser Val Val Gln Gln Pro Gln Ile Thr Ala
            260                 265                 270

Val Asp Gly Ala Ala Gly Lys Thr Ile Thr Val Phe Thr Val Asp Pro
        275                 280                 285

Leu Ala Gln Glu Val Ile Thr Thr Asn Gly Ala Leu Pro Lys Ile Thr
    290                 295                 300

Lys Thr Asp Ala Asn Gly Val Ile Ala Leu Thr Thr Gly Val Ser Val
305                 310                 315                 320

Val Thr Asp Ile Gly Gln Gln Ala Val Phe Pro Asp Ser Ser Phe Val
                325                 330                 335

Ser Asp Ile Leu Ala Asp Gly Ser Met Ser Leu Ser Phe Val Pro Lys
            340                 345                 350

Asn Phe Ile Ser Gln Ile Leu Phe Gln Gly Val Pro Val Ser Ile Ser
        355                 360                 365

Ile Thr Glu Asn Asp Tyr Thr Ala Ser Val Val Gly Asn Ser Gly Asp
    370                 375                 380

Val Ile Thr Pro Gln Val Leu Leu Gln Lys Lys Ile Ser Leu Phe Pro
385                 390                 395                 400

Val Pro Ile Thr Gly Ile Val Asn Gly Asn Phe Ala Thr Asp Lys Gly
                405                 410                 415

Phe Pro Lys Thr Phe Ala Thr Phe Gln Leu Met Asp Val Ala Asn Asn
            420                 425                 430

Thr Gln Tyr Asp Trp Ser Ser Ser Phe Val Gln Gly Val Ile Tyr Thr
        435                 440                 445

Tyr Ser Val Val Thr Ala Lys Ser Lys Lys Phe Pro Ser Tyr Ser Ser
    450                 455                 460

Tyr Phe Pro Asn Trp Ile Phe Gly Ser Ser Leu Ser Ser Leu Glu Ala
465                 470                 475                 480

Ser Arg Asn Cys Gln Ser Asp Ser Ala Leu Ile Glu Ser Ala Arg Ala
                485                 490                 495

Ser Asn Gly Ser Arg Ala Pro Asp Gly Thr Leu Trp Gly Glu Trp Gly
            500                 505                 510

Ser Leu Tyr Ala Asp Trp Ser Gly Tyr Trp Lys Lys Thr Ser Thr Asp
        515                 520                 525

Phe Thr Met Met Thr Gly Ile Ala Ala Phe Pro Leu Cys Ala
    530                 535                 540
```